US008440621B2

(12) United States Patent
Chandy et al.

(10) Patent No.: US 8,440,621 B2

(45) Date of Patent: May 14, 2013

(54) ANALOGS OF SHK TOXIN AND THEIR USES IN SELECTIVE INHIBITION OF KV1.3 POTASSIUM CHANNELS

(75) Inventors: George K. Chandy, Laguna Beach, CA (US); Christine Beeton, Irvine, CA (US); Michael William Pennington, New Jersey, CA (US)

(73) Assignees: The Regents of the University of California, Oakland, CA (US); Bachem Biosciences, Inc., King of Prussia, PA (US)

( * ) Notice: Subject to any disclaimer, the term of this patent is extended or adjusted under 35 U.S.C. 154(b) by 0 days.

(21) Appl. No.: 13/286,939

(22) Filed: Nov. 1, 2011

(65) Prior Publication Data

US 2012/0142600 A1 Jun. 7, 2012

Related U.S. Application Data

(63) Continuation of application No. 11/663,398, filed as application No. PCT/US2005/036234 on Oct. 7, 2005, now Pat. No. 8,080, 523.

(60) Provisional application No. 60/617,395, filed on Oct. 7, 2004.

(51) Int. Cl.

| | |
|---|---|
| ***A61K 38/00*** | (2006.01) |
| ***A61K 38/16*** | (2006.01) |
| ***A61P 3/04*** | (2006.01) |
| ***A61P 25/00*** | (2006.01) |

(52) U.S. Cl.
USPC ........................................ 514/17.4; 514/17.7

(58) Field of Classification Search ........................ None
See application file for complete search history.

(56) References Cited

U.S. PATENT DOCUMENTS

| | | | | |
|---|---|---|---|---|
| 6,077,680 | A | 6/2000 | Kem et al. | |
| 6,616,944 | B2 | 9/2003 | Kissel et al. | |
| 6,861,405 | B2 | 3/2005 | Desir et al. | |
| 8,080,523 | B2 * | 12/2011 | Beeton et al. | 514/17.4 |

FOREIGN PATENT DOCUMENTS

| | | |
|---|---|---|
| WO | 9823639 | 6/1998 |
| WO | 9913895 | 3/1999 |

OTHER PUBLICATIONS

Kalman, et al., ShK-Dap22, a Potent Kv1.3-specific Immunosuppressive Polypeptide, J. Biol Chem., 1998, vol. 273, No. 49, pp. 32697-32707.

Lanigan, M.D. et al., Designed Peptide Analogues of the Potassium Channel Blocker ShK Toxin; Biochemistry, 25; 40 (51):15528-37, Dec. 2001.

King D.S., et al, 1990, Int. J. Peptide Protein Res., 36, 255-266.

Pennington, et al., Int. J Peptide Protein Res., 46, 354-358, 1995.

Stewart, J.M., et al., Solid Phase Peptide Sythesis, 2nd Edition, Pierce Chemical Company, Rockford, Ill., 1984.

Wilken, J. et al., Chemical Protein Synthesis, Current Opin. Biotech., 9,412-426, 1998.

Albericio, F., et al., Convergent Peptide Synthesis; in Methods in Enzymol. Ed G. Fields, Academic Press, New York, NY, pp. 313-335, Available online Dec. 8, 2003.

Beeton, C. et al., Targeting Effector Memory T Cells with a Selection Peptide Inhibitor of Kv1.3 Channels for Therapy of Autoimmune Diseases, Molecular Pharmacology, vol. 67, No. 4, 1369-, 2005.

Beeton, C. et al., A Novel Fluorescent Toxin to Detect and Investigate Kv1.3 Channel Up-Regulation in Chronically Activated T Lymhocytes, J. Biol. Chem., vol. 278, No. 11, 9928-9937, Mar. 2003.

Beeton, C et al., Selective blockage of T lymphocyte K+ channels ameliorates experimental autoimmune encephalomyelitis experimental autoimmune encephalomyelitis, a model for multiple sclerosis, Proceedings of the National Academy of Sciences of USA, Nov. 20, 2001, pp. 13942-13947, vol. 98, No. 24, Washington, DC, US.

European Search Report in reference to PA 6031 PCT/EP, European Patent Office, Sep. 10, 2009, Munich.

Chandy, George K., et al.; K+ channels as targets for specific immunomodulation, Trends in Pharmacological Sciences, May 1, 2004, pp. 280-289, vol. 25, No. 5, Elsevier, Haywarth, GB.

Pennington et al. Structural Stabilization and Minimization of the Potassium Channel Blocker, ShK Toxin. Peptides 2000, pp. 155-156.

Hruby. Designing Peptide Receptor Agonists and Antagonists. Nature Reviews. Drug Discovery. Nov. 2002. vol. 1, pp. 847-858.

H.J.C. Berendsen. A Glimpse of the Holy Grail? Science (1998) 282, pp. 642-643.

Rudinger. In: Peptide Hormones, JA Parsons, Ed. (1976), pp. 1-7.

SIGMA. Designing Custom Peptides. http://www.sigma-genosys.com/peptide.sub.--design.asp (Accessed Dec. 16, 2004), 2 pages.

W.S. Messer, "Vasopressin and Oxytocin", web document updated Apr. 3, 2000; http://www.neurosci.pharm.utoledo.edu/MBC3320/vasopressin.htm; 5 pages.

D.E. Smilek, et al. Proc. Natl. Acad. Sci. USA (1991) 88, pp. 9633-9637.

D. Voet and J.G. Voet. Biochemistry, 2nd Edition.(1995), pp. 235-241.

* cited by examiner

*Primary Examiner* — Marcela M Cordero Garcia

(74) *Attorney, Agent, or Firm* — Robert D. Buyan; Stout, Uxa, Buyan & Mullins, LLP

(57) ABSTRACT

Analogs of ShK toxin and methods for using such ShK analogs. The ShK analogs generally comprise ShK toxin attached to a chemical entity (e.g. an atom, molecule, group, residue, compound, moiety, etc.) that has an anionic charge. The ShK analogs may be administered to human or non-human animal subjects to cause inhibition of potassium channels or to otherwise treat diseases or disorders. In some embodiments, the chemical entity to which the ShK toxin is attached may be chosen to provide selective inhibition of certain potassium channels (e.g., Kv1.3 channels) over other potassium channels (e.g., Kv1.1 channels). In come embodiments, the chemical entity to which the ShK toxin is attached may include a fluorophore and such fluorophore-tagged ShK analogs may be used in flow cytometry alone, or in conjunction with class II tetramers that can detect autoreactive cells.

20 Claims, 20 Drawing Sheets

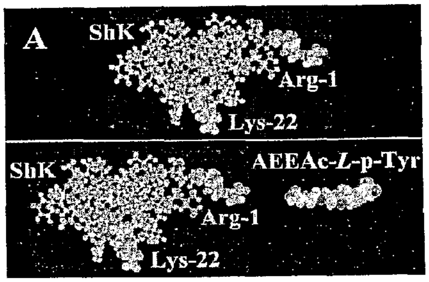

Fig. 2A

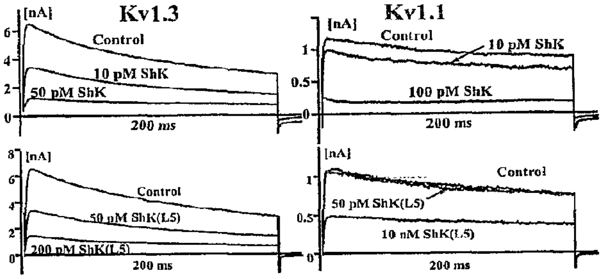

Fig. 2B

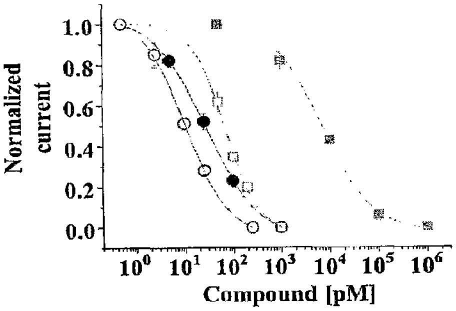

Fig. 2C

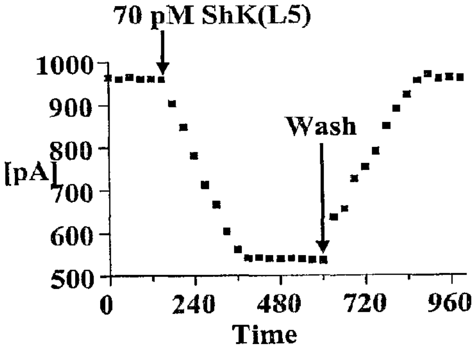

Fig. 2D

| Compound | Residue attached at position -2 | Net charge at position -2 | $K_d$ on Kv1.3 [pM] | $K_d$ on Kv1.1 [pM] | Ratio of $K_d$s |
|---|---|---|---|---|---|
| ShK | None | None | 10 ± 1 | 28 ± 6 | 2.8 |
| ShK(L5) | L-p-Tyr | -2 | 69 ± 5 | 7,400 ± 900 | 104.2 |
| ShK(D5) | D-p-Tyr | -2 | 1,100 ± 150 | 39,000 ± 650 | 35.4 |
| ShK(L6) | L-p-Tyr monomethyl | -1 | 10 ± 1 | 112 ± 9 | 11.2 |
| ShK(L7) | L-p-Tyr dimethyl | 0 | 24 ± 2 | 175 ± 30 | 7.3 |
| ShK(L4) | L-Tyr | 0 | 47 ± 6 | 159 ± 5 | 3.4 |
| ShK(L1) | L-Pmp | -2 | 293 ± 45 | 1,000 ± 100 | 3.4 |
| ShK(D1) | D-Pmp | -2 | 96 ± 12 | 1,400 ± 80 | 14.6 |
| ShK(D2) | D-Pmp monoethyl | -1 | 311 ± 16 | 1,100 ± 100 | 3.5 |
| ShK(L3) | L-Pmp diethyl | 0 | 71 ± 6 | 1,100 ± 200 | 15.5 |
| ShK(D3) | D-Pmp diethyl | 0 | 70 ± 9 | 166 ± 13 | 2.4 |
| ShK(L9) | L-p-COOH-Phe | -1 | 94 ± 7 | 319 ± 36 | 3.4 |
| ShK-L8 | L-p-amino-Phe | +1 | 65 ± 4 | 142 ± 13 | 2.2 |
| ShK-F6CA | F6CA | -1 | 48 ± 4 | 4,000 ± 300 | 83 |
| ShK-$Dap^{22}$ | None | None | 52 ± 3 | 1,800 ± 577 | 35 |

Fig. 2E

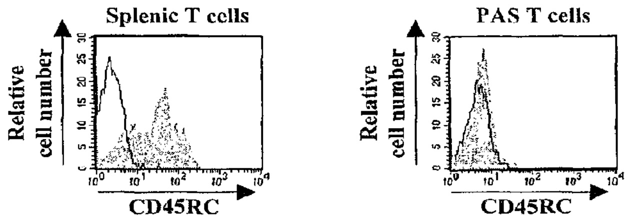
Fig. 4A
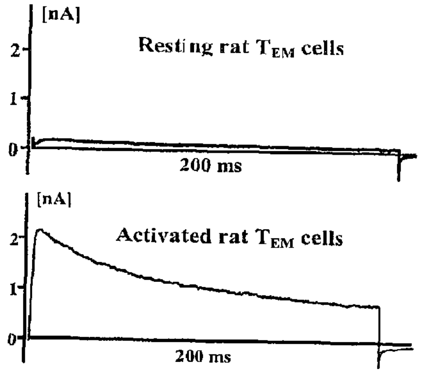
Fig. 4B
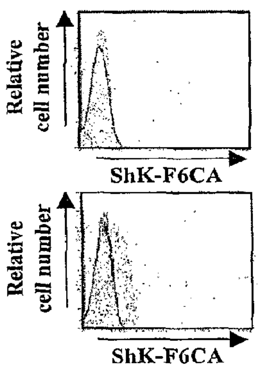
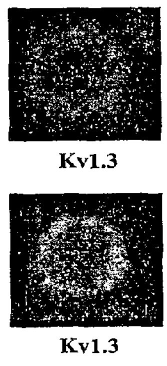
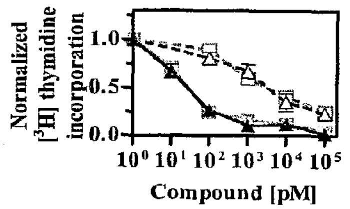
Fig. 4C Fig. 4D Fig. 4E
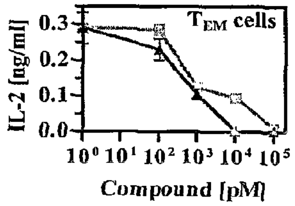
Fig. 4F
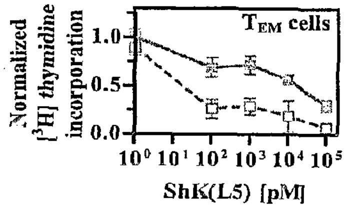
Fig. 4G APC loaded with GAD557I and DAPI APC loaded with GAD557I and DAPI
No contact between T and B cells APC loaded with MBP and DAPI APC loaded with GAD557I and DAPI
ShK(L5) does not prevent IS formation APC loaded with GAD557I and DAPI
ShK(L5) does not disrupt the IS

| | | |
|---|---|---|
| MS | GAD65/Insulin-specific T cells | MBP-specific T cells |
| T1DM | MBP-specific T cells | GAD65/Insulin-specific T cells |
| RA | Peripheral blood T cells | Synovial fluid T cells |

ANALOGS OF SHK TOXIN AND THEIR USES IN SELECTIVE INHIBITION OF KV1.3 POTASSIUM CHANNELS

RELATED APPLICATIONS

This patent application is a continuation of U.S. patent application Ser. No. 11/663,398 filed Aug. 16, 2007 which is a 35 U.S.C. §371 national stage application based on PCT International Patent Application No. PCT/US2005/036234 filed Oct. 7, 2005 which claims priority to U.S. Provisional Patent Application No. 60/617,395 filed on Oct. 7, 2004, the entire disclosure of each such application being expressly incorporated herein by reference.

SEQUENCE LISTING

The instant application contains a Sequence Listing which has been submitted in ASCII format via EFS-Web and is hereby incorporated by reference in its entirety. Said ASCII copy, created on Oct. 29, 2012, is named UCIVN66C.txt and is 5,311 bytes in size.

FIELD OF THE INVENTION

The present invention provides a) novel compositions of matter, b) methods and kits for in vivo and/or in vitro inhibition of the Kv1.3 channel in T- and B-lymphocytes and other cell types and c) methods for treating autoimmune and other disorders in human or animal subjects.

BACKGROUND OF THE INVENTION

Cell plasma membranes form the outer surfaces of eukaryotic cells. Various ions (e.g., sodium, potassium, calcium, etc.) move in and out of cells by passive diffusion through the cells' plasma membranes. Such diffusion of ions into and out of cells is facilitated by the presence of "ion channels" within the cell membranes. Ion channels are proteins embedded within the cell membrane that control the selective flux of ions across the membrane, thereby allowing for the formation of concentration gradients between the intracellular contents of the cell and the surrounding extracellular fluid. Because ion concentrations are directly involved in the electrical activity of excitable cells (e.g., neurons), the functioning (or malfunctioning) of ion channels can substantially control the electrical properties and behavior of such cells. Indeed, a variety of disorders, broadly termed "channelopathies," are believed to be linked to ion channel insufficiencies or dysfunctions.

Ion channels are referred to as "gated" if they can be opened or closed. The basic types of gated ion channels include a) ligand gated channels, b) mechanically gated channels and c) voltage gated channels. In particular, voltage gated channels are found in neurons, muscle cells and non-excitable cells such as lymphocytes. They open or close in response to changes in the charge across the plasma membrane.

Kv1.3 Channels and Autoimmune Diseases.

Autoimmune diseases such as multiple sclerosis (MS), type-1 diabetes mellitus (T1DM), rheumatoid arthritis (RA) and psoriasis affect several hundred million people worldwide. In these disorders specific autoreactive T cells—for instance myelin-specific T cells in MS patients—are believed to undergo repeated autoantigen stimulation during the course of disease and differentiate into chronically activated memory cells that contribute to pathogenesis by migrating to inflamed tissues and secreting cytokines (Viglietta et al., 2002; Vissers et al., 1002; Wulff et al., 2003b). Therapies that preferentially target chronically activated memory T cells would have significant value for autoimmune diseases.

Memory T cells are divided into two subsets—central memory ($T_{CM}$) and effector memory ($T_{EM}$)—based on the expression of the chemokine receptor CCR7 and the phosphatase CD45RA (Geginat et al., 2001; Sallusto et al., 1999). Naïve and $T_{CM}$ cells home to the lymph node before they migrate to sites of inflammation, whereas $T_{EM}$ cells home directly to sites of inflammation where they secrete copious amounts of IFN-β and TNF-α and exhibit immediate effector function. It has recently been shown that myelin-specific autoreactive T cells in MS patients are predominantly activated $T_{EM}$ cells (Wulff et al., 2003b), and adoptive transfer of myelin-specific activated rat $T_{EM}$ cells into naïve recipients induced severe EAE (Beeton et al., 2001a; Beeton et al., 2001b). An exciting new therapeutic target for immunomodulation of $T_{EM}$ cells is the voltage-gated Kv1.3 $K^+$ channel. $T_{EM}$ cells up-regulate Kv1.3 channels upon activation and their antigen-driven proliferation is exquisitely sensitive to Kv1.3 blockers (Wulff et al., 2003b). Naïve and $T_{CM}$ cells in contrast are significantly less sensitive to Kv1.3 blockers to begin with and rapidly become resistant to Kv1.3 blockade by up-regulating the calcium-activated $K^+$ channel IKCa1 (Ghanshani et al., 2000; Wulff et al., 2003b).

The dominance of Kv1.3 in $T_{EM}$ cells provides a powerful way to manipulate the activity of this subset with specific Kv1.3 inhibitors. The functionally restricted tissue distribution of the channel and the fact that in vivo Kv1.3 blockade ameliorates $T_{EM}$-mediated EAE, bone resorption in peridontal disease and delayed type hypersensitivity reactions in animal models without causing obvious side effects has enhanced the attractiveness of Kv1.3 as a therapeutic target (Beeton et al., 2001b; Koo et al., 1997; Valverde et al., 2004). Although Kv1.3 blockers would suppress all activated $T_{EM}$ cells (for example $T_{EM}$ cells specific for vaccine antigens), a Kv1.3-based therapy would be a significant improvement over current therapies that broadly and indiscriminately modulate the entire immune system. An additional advantage of Kv1.3 blockers is that they are reversible. Thus, one could titrate the therapeutic effect of Kv1.3 blockers when needed and stop therapy in the face of infection, unlike chemotherapeutic agents, which take months to subside.

Kv1.3 Channels and Obesity

The Kv1.3 channel was found to play a role in energy homeostasis and energy balance (*Hum Mol Genet.* 2003 12:551-9). Mice with the Kv1.3 channel genetically knocked out were able to eat fatty diets without gaining weight, while control mice given the same diet became over-weight. Pharmacological blockade of Kv1.3 channels recapitulated the effect of genetic knockout of Kv1.3 channels. Consequently, Kv1.3 blockers are likely to have use in the management of obesity.

Kv1.3 Channels and Type-2 Diabetes Mellitus.

Kv1.3 channels play a role in regulating insulin-sensitivity in peripheral target organs such as the liver and muscle (*Proc Natl Acad Sci USA.* 2004 101:3112-7). Genetic knockout of the Kv1.3 channel in mice enhanced the sensitivity of the liver and muscle to insulin. Consequently, Kv1.3 blockers may have use in the treatment of type-2 diabetes mellitus by enhancing insulin's peripheral actions and thereby decreasing blood glucose levels.

Naturally Occurring Polypeptides Known to Inhibit Kv1.3 Channels

The most potent Kv1.3 inhibitor is the peptide ShK from the Caribbean sea anemone *Stichodactyla helianthus*. ShK is a 35-residue polypeptide cross-linked by 3 disulfide bridges. ShK blocks Kv1.3 ($K_d$=11 pM) and suppresses proliferation of $T_{EM}$ cells at picomolar concentrations, and ameliorates experimental autoimmune encephalomyelitis (EAE) in rats induced by the adoptive transfer of myelin-specific $T_{EM}$ cells. A potential drawback of ShK is its low picomolar affinity for the neuronal Kv1.1 channel ($K_d$ 28 pM). Although no side effects were observed with ShK in EAE trials, ingress of high concentrations of ShK into the brain, as might happen when the blood-brain-barrier is compromised in MS, could lead to unwanted neurotoxicity. The development of highly specific Kv1.3 inhibitors is therefore necessary. An extensive effort by the pharmaceutical industry and academic groups has yielded several small molecules that inhibit Kv1.3 in the mid-nanomolar range, but these compounds do not have the selectivity or potency to make them viable drug candidates.

Several truncated peptidic analogs of ShK have previously been reported. In one of these ShK analogs, the native sequence was truncated and then stabilized by the introduction of additional covalent links (a non-native disulfide and two lactam bridges). In others, non-native structural scaffolds stabilized by disulfide and/or lactam bridges were modified to include key amino acid residues from the native toxin. These ShK analogs exhibited varying degrees of Kv1.3 inhibitory activity and specificity. Lanigan, M. D. et al.; *Designed Peptide Analogues of the Potassium Channel Blocker ShK Toxin*; Biochemistry, 25; 40(51):15528-37 (December 2001).

There remains a need in the art for the development of new analogs of ShK that selectively inhibit Kv1.3 channels in lymphocytes with minimal or no inhibitory effects on Kv1.1 channels or other potassium channels.

SUMMARY OF THE INVENTION

The present invention provides novel compositions (referred to herein as "ShK analogs") comprising ShK toxin attached (e.g., bound, linked by a linker or otherwise associated with) to an organic or inorganic chemical entity (e.g. an atom, molecule, group, residue, compound, moiety, etc.) that has an anionic charge.

Further in accordance with the present invention, there are provided methods for inhibiting potassium channels and/or treating diseases or disorders in human or animal subjects by administering to the subject an effective amount of an ShK analog of the present invention. In some embodiments, the chemical entity to which the ShK toxin is attached may be chosen to provide selective inhibition of certain potassium channels (e.g., Kv1.3 channels) over other potassium channels (e.g., Kv1.1 channels).

Still further in accordance with the present invention, ShK analogs of the foregoing character may include a fluorophore tag and such fluorophore tagged ShK analogs of the present invention may be used in flow cytometry alone, or in conjunction with class II tetramers that can detect autoreactive cells.

The known amino acid sequence of SHK toxin is Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys (SEQ ID NO:1). Compositions of the present invention include those having the following sequences:

p-phospho-Tyr-AEEAc-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys (SEQ ID NO:2);

p-phospho-Tyr-AEEAc-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys-amide (SEQ ID NO:3);

Tyr-AEEAc-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys-amide (SEQ ID NO:4);

Phosphono(difluoro-methyl)-Phenylalanine-AEEAc-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys (SEQ ID NO: 5);

Phosphono(difluoro-methyl)-Phenylalanine-AEEAc-Arg-Ser-Cys-Ile-Asp-Thr-Ile-Pro-Lys-Ser-Arg-Cys-Thr-Ala-Phe-Gln-Cys-Lys-His-Ser-Nle-Lys-Tyr-Arg-Leu-Ser-Phe-Cys-Arg-Lys-Thr-Cys-Gly-Thr-Cys-amide (SEQ ID NO: 6);

Phosphono-methylketo-Phenylalanine-AEEAc-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys (SEQ ID NO: 7);

Phosphono-methylketo-Phenylalanine-AEEAc-Arg-Ser-Cys-Ile-Asp-Thr-Ile-Pro-Lys-Ser-Arg-Cys-Thr-Ala-Phe-Gln-Cys-Lys-His-Ser-Nle-Lys-Tyr-Arg-Leu-Ser-Phe-Cys-Arg-Lys-Thr-Cys-Gly-Thr-Cys-amide (SEQ ID NO: 8).

Further aspects, elements and details of the present invention will be apparent to those of skill in the art upon reading the detailed description and examples set forth herebelow.

BRIEF DESCRIPTION OF THE DRAWINGS

FIG. 2A shows a molecular model of ShK based on the published NMR structure wherein the $Lys^{22}$, critical for channel blockade, is highlighted in one shade of grey. L-pTyr was attached to the α-amino group of $Arg^1$ of ShK (highlighted in a second shade of grey) through an Aeea linker (right). The structures of the linker and L-pTyr were modeled with AM1 in Hyperchem.

FIG. 2B shows the effect of ShK (top) and ShK(L5) (bottom) on Kv1.3 and Kv1.1 currents in stably transfected cells.

FIG. 2C shows dose-dependent inhibition of Kv1.3 (open symbols) and Kv1.1 (closed symbols) by ShK (dark) and ShK(L5) (light). $K_d$s on Kv1.3=10±1 pM (ShK) and 69±5 pM (ShK(L5)); $K_d$s on Kv1.1=28±6 pM (ShK) and 7.4±0.8 nM (ShK(L5)).

FIG. 2D shows the time course of wash-in and wash-out of ShK(L5) on Kv1.3 wherein cells were held at a holding potential of 80 mV and depolarized for 200 msec to 40 mV every 30 secs.

FIG. 2E shows $K_d$ values for inhibition of Kv1.3 and Kv1.1 by ShK analogs. $K_d$s for ShK-F6CA and ShK-$Dap^{22}$ based on published sources.

FIG. 4A is a graph showing CD45RC staining of rat splenic T cells (left) and PAS T cells (right) detected by flow cytometry.

FIG. 4B is a graphic showing of Kv1.3 currents exhibited by quiescent (top) and myelin antigen-activated (bottom) PAS T cells.

FIG. 4C provides a graphic representation of flow cytometry profiles of ShK-F6CA-staining in quiescent (top) and myelin antigen-activated (bottom) PAS T cells. Unstained cells (black lines) and cells stained with ShK-F6CA (area filled in light grey). Competition of ShK-F6CA staining by unlabeled ShK(L5) is represented by the area filled in dark grey.

FIG. 4D shows confocal images of Kv1.3 immunostaining in quiescent (top) and myelin antigen-activated (bottom) PAS T cells. Statistical analysis was carried out using the Mann-Whitney U-test.

FIG. 4E shows dose-dependent inhibition by ShK (dark lines) and ShK(L5) (light lines) of [$^3$H] thymidine incorporation by rat (left) naïve/$T_{CM}$ (open symbols) and $T_{EM}$ (closed symbols) cells activated with Con A (1 μg/ml).

FIG. 4F shows dose-dependent inhibition by ShK (dark lines) and ShK(L5) (light lines) of IL2 secretion by PAS T cells 7 hours after stimulation with MBP.

FIG. 4G is a graph showing that ShK(L5)-induced inhibition of myelin-antigen triggered [$^3$H] thymidine incorporation by PAS T cells (open symbols) is reversed by the addition of 20 u/ml IL2 (closed symbols).

DETAILED DESCRIPTION

The following detailed description and the accompanying drawings are intended to describe some, but not necessarily all, examples or embodiments of the invention only. This detailed description and the accompanying drawings do not limit the scope of the invention in any way.

The present invention provides novel analogs of ShK, methods for making such compositions and methods for using such compositions to inhibit Kv1.3 channels (or other ion channels) in human or animal cells and for treatment or prevention of diseases and disorders, such as T cell mediated autoimmune disorders. The compositions of the present invention comprise ShK toxin attached (e.g., bound, linked by a linker or otherwise associated with) to an organic or inorganic, anionic-charged chemical entity (e.g. an atom, molecule, group, residue, compound, moiety, etc.). In at least some embodiments of the invention, the organic or inorganic, anionic-charged chemical entity may be selected to increase or optimize the affinity of the composition for inhibition of Kv1.3 channels over Kv1.1 channels. Examples of organic or inorganic, anionic-charged molecules or groups that may be linked or bound to ShK in accordance with the present invention include but are not necessarily limited to:

amino acids;
polypeptides;
amino acid residues;
unnatural amino acid residues;
threonine;
threonine derivatives;
phospho-threonine;
serine;
serine derivatives;
phospho-serine;
glutamic acid;
glutamic acid derivatives;
gammacarboxy-glutamic acid;
aspartic acid;
aspartic acid derivatives;
inorganic compounds or groups;
organic compounds or groups;
succinic anhydride; and
phthalic anhydride.

Figure 1:
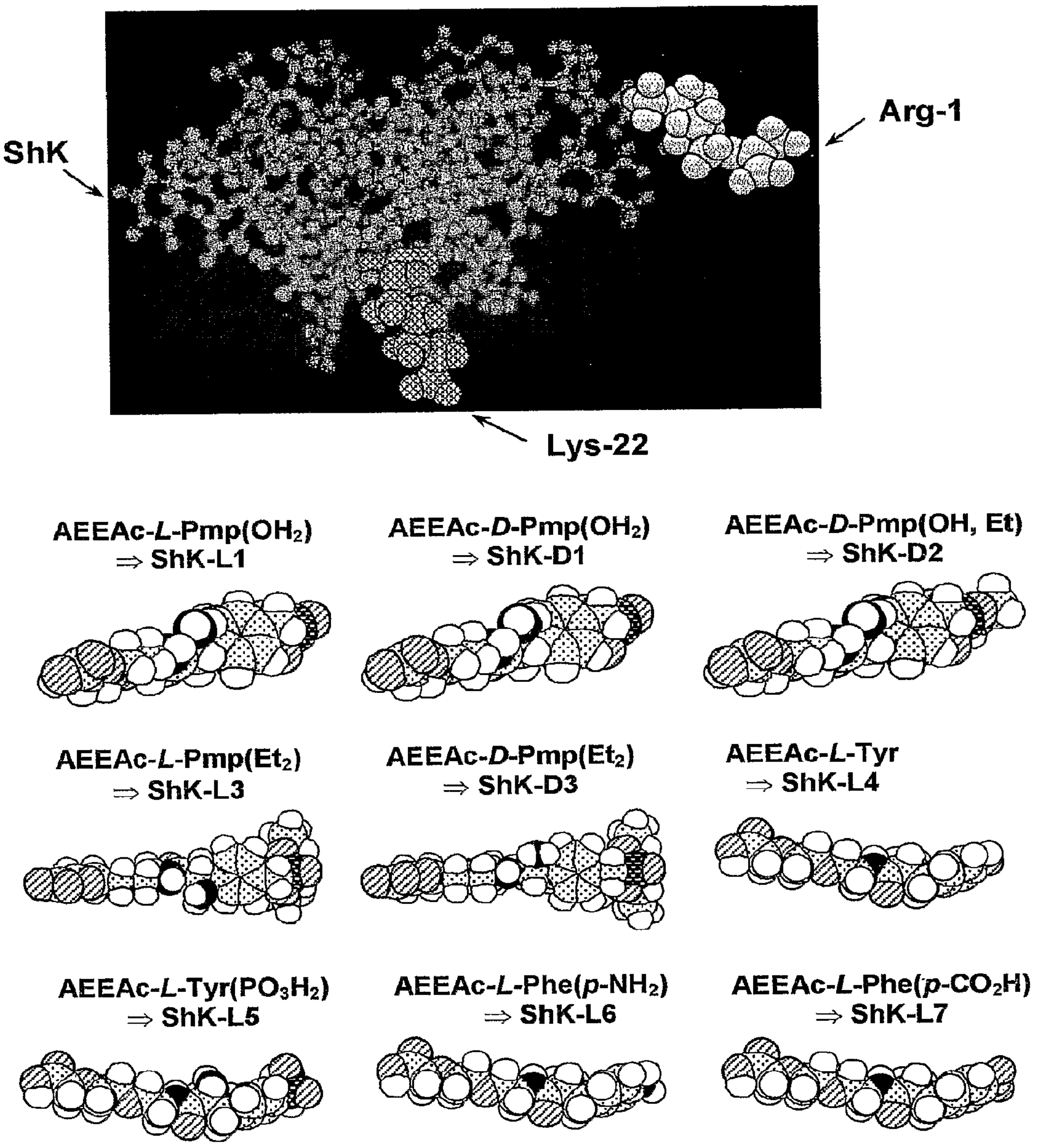
FIG. 1 shows the chemical structures of a number of ShK analogs of the present invention.

In accordance with the present invention, some non-limiting examples of compositions of the present invention, wherein the anionic-charged chemical entity comprises an amino acid residue, are shown in FIGS. 1 and 2C and referred to herein by alphanumeric designations, as shown in Table 1 below:

TABLE 1

| DESIGNATION | AMINO ACID RESIDUE BOUND TO ShK AT POSITION 2 |
|---|---|
| ShK-L1 | AEEAc-L-Pmp($OH_2$) |
| ShK-D1 | AEEAc-D-Pmp($O_2$) |
| ShK-D2 | AEEAc-D-Pmp(OH, Et) |
| ShK-L3 | AEEAc-L-Pmp($Et_2$) |
| ShK-D3 | AEEAc-D-Pmp($Et_2$) |
| ShK-L4 | AEEAc-L-Tyr |
| ShK-L5 | AEEAc-L-Tyr($PO_3H_2$) |
| ShK-L6 | AEEAc-L-Phe(p-$NH_2$) |
| ShK-L7 | AEEAc-L-Phe(p-$CO_2H$) |

With specific reference to FIG. 1, tyrosine or phenylalanine or their charged non-natural derivatives were conjugated to ShK (top left) through a linker attached on its N terminus (residue Arg1 shown in shaded grey). The Lys22, required for channel blockade, is shown in a darker shade of grey. The molecular model of ShK is based on the published NMR structure and the structures of the linker and the new residues were modeled. These embodiments of compositions of the present invention generally comprise the ShK toxin, which is a polypeptide, bound to (e.g., chemically bound, linked or otherwise associated with) at least one anionic-charged amino acid residue. In embodiments where the amino acid residue has a chiral center, the D and/or L enantiomer of such amino acid residue may be used. The anionic-charged amino acid residue may be an unnatural residue and may be attached or linked to an N-terminus of the ShK polypeptide. In some embodiments, the anionic-charged amino acid residue may be linked to an N terminus of ShK through a linker, such as an aminoethyloxyethyloxy-acetyl linker. These analogs of ShK inhibit the Kv1.3 channel more specifically than ShK because they have reduced affinity for other potassium channels (e.g., Kv1.1). The ShK may be isolated from natural sources as known in the art, or it may be synthesized.

Synthesis of ShK Toxin

ShK Toxin may be synthesized by any suitable method. In one such method, Fmoc-amino acids (Bachem Feinchemikalien) including Arg(Pmc), Asp(OtBu), Cys(Trt), Gln(Trt), His(Trt), Lys(Boc), Ser(tBu) and Thr(tBu) are obtained commercially and assembled to form ShK Toxin. Stepwise assembly of the amino acids may be carried out on an Applied Biosystems 431A peptide synthesizer at the 0.25 mmol scale starting with Fmoc-Cys(Trt)-R. Residues 34 through 22 are single coupled. Thereafter, an aliquot (e.g., half) of the resin is removed to effect better mixing. The remainder of the peptide sequence is then double coupled to the remaining resin aliquot. All couplings are mediated by dicyclohexylcarbodiimide in the presence of 2 eq of 1-hydroxybenzotriazole. The final two residues are also coupled via HBTU/DIEA chemistry. These residues are Aeea (Fmoc-aminoethyloxyethyloxyacetic acid) and as the N-terminal residue Fmoc-Tyr (PO4) monobenzyl ester. Following final removal of the Fmoc-group, the peptide resin (2.42 g) is cleaved from the resin and simultaneously deprotected using reagent K for 2 h at room temperature. Reagent K is known in the art and has been described in the literature. See, King, D. S., Fields, C. G. and Fields, G. B. (1990) *Int. J. Peptide Protein Res.* 36, 255-266. Following cleavage, the peptide is filtered to remove the spent resin beads and precipitated with ice cold diethyl ether. The peptide is then collected on a fine filter funnel, washed with ice cold ether and finally extracted with 20% AcOH in $H_2O$. The peptide extract is subsequently diluted into 2 liters of $H_2O$, the pH is adjusted to 8.0 with $NH_4OH$ and allowed to air oxidize at room temperature for 36 hours. Following oxidation of the disulfide bonds with a 2:1 ratio of reduced to oxidized glutathione, the peptide solution is acidified to pH 2.5 and pumped onto a Rainin Dynamax $C_{18}$ column (5.0×30 cm). The sample is eluted with a linear gradient from 5-30% acetonitrile into $H_2O$ containing 0.1% TFA. The resulting fractions are analyzed using two analytical RP-HPLC systems: TFA and TEAP. Pure fractions are pooled and lyophilized. (See, Pennington, M. W., Byrnes, M. E., Zaydenberg, I., Khaytin, I., de Chastonay, J., Krafte, D., Hill, R., Mahnir, V., Volberg, W. A., Gorczyca, W. and Kem, W. R. (1995) *Int. J. Peptide Protein Res.* 46, 354-358.)

Alternatively, solid-phase peptide synthesis employing a Boc-Bzl protecting group strategy may be utilized to assemble the primary structure as well as analogs of the peptide. The peptide could then be cleaved from the solid-phase by anhydrous HF, yielding the linear peptide ready for folding as described above for the Fmoc synthesized peptide. (See, Stewart, J. M. and Young J. D. (1984) Solid Phase Peptide Synthesis. $2^{nd}$ Edition. Pierce Chemical Company. Rockford, II.)

Alternatively, other synthetic methods to assemble the primary structure of ShK or analogs could include chemical ligation technology where the peptide is prepared as a series of designed fragments with C-terminal thioester peptides. The thioester peptide can react with another peptide containing an N-terminal Cys residue to form a peptide containing a native peptide bond. By using this technology, one could effectively assemble the primary structure of ShK. (See, (4) Wilken, J. and Kent S. B. H. (1998) Chemical protein synthesis. *Current Opin. Biotech.* 9, 412-426.)

Alternatively, another synthetic method that may be employed to assemble the primary structure of ShK would utilize a protected peptide fragment convergent approach as described in Albericio, F., Lloyd-Williams, P., and Giralt, E. (1997) Convergent peptide synthesis; in Methods in Enzymol. Ed G. Fields, Academic Press, New York, N.Y. pp 313-335. In this method, linear protected fragments are assembled as fully side chain protected fragments. These fragments can then be coupled together in a convergent manner to assemble the primary sequence of ShK or one of its analogs. Assembly of the fragments could also utilize a solid-phase resin to facilitate coupling and wash steps.

Alternatively, recombinant methods may be used wherein the cDNA coding sequence for ShK could be generated for expression in either a prokaryotic or eucaryotic expression system. Recombinant ShK analogs containing unnatural amino acids are also possible by utilizing preload tRNA molecules which utilize non-standard condons. The cCNA construct can be engineered to use one of these unused codons to add the phosphotyrosine residue as well as the Aeea residue. Folding of the recombinantly produced ShK analog could then be accomplished in a similar method to that used for the synthetic peptides. (See, Pennington, M. W., Byrnes, M. E., Zaydenberg, I., Khaytin, I., de Chastonay, J., Krafte, D., Hill, R., Mahnir, V., Volberg, W. A., Gorczyca, W. and Kem, W. R. (1995) *Int. J. Peptide Protein Res.* 46, 354-358.)

Attaching Anionic Amino Acid Residues to ShK and Optional Modifications to ShK

Anionic amino acid residues may be attached to the N terminus of natural or synthetic ShK Toxin by way of a linker, such as an aminoethyloxyethyloxy-acetyl linker, or bay any other suitable means. In this example, the nine (9) ShK analogs shown in FIG. 1 are prepared. Initially, Fmoc-Aeea-OH is coupled to the N-terminus of synthetic ShK Toxin assembled as described above. The resin is then divided into 9 aliquots. Either Fmoc-Tyr($PO_4Bzl$)-OH, Fmoc-d-Tyr ($PO_4Bzl$)-OH, Fmoc-Tyr($PO_4Me_2$)—OH, Fmoc-Pmp-OH, Fmoc-d-Pmp-OH, Fmoc-Pmp(Et)-OH, Fmoc-Pmp$(Et)_2$-OH, Fmoc-Tyr(tBu)-OH, or Fmoc-Amp(Boc)-OH is then coupled using DIC and HOBT to one of the resin aliquots. The deblocked peptide resin is then cleaved and deprotected with reagent K (King et al., 1990) containing 5% triisopropylsilane for 2 h at RT. Met(O) is reduced by addition of solid $NH_4I$ to the cleavage cocktail at t-15 min. (Nicolas et al., 1995). For the peptide containing Tyr($PO_4Me_2$)—OH, a cleavage cocktail containing 1 M TMSBr in TFA containing thioanisole as a scavenger for 18 hr at 4° C. was used (Tian et al., 1993). Incomplete removal of the methyl protecting groups is common when using this method and two of the species (Tyr($PO_4$) and Tyr($PO_4$Me)) are easily purified by RP-HPLC. The Tyr($PO_4Me_2$) containing analog is cleaved via standard Reagent K cleavage keeping both Me groups intact. In each case, the cleavage mixture is filtered and the crude peptide is precipitated into ice-cold diethyl ether. The precipitate is collected, yielding approximately 75 mg of peptide from 200 mg of resin. The crude product is dissolved in 20 ml of 50% aqueous AcOH and diluted into 0.75 l of $H_2O$. The pH of the solution is adjusted with $NH_4OH$ to 8.2, and it was allowed to fold overnight with the addition of glutathione (2 mM:1 mM) (reduced:oxidized). All analogs are purified using RP-HPLC as described previously (Pennington et al., 1995; Pennington et al., 1996a; Pennington et al., 1996b). Pure fractions are pooled and lyophilized. Each sample is confirmed by RP-HPLC, AAA and MALDI-TOF MS and adjusted to account for peptide content prior to bioassay.

In some embodiments of the invention, to improve the PK/PD properties of the ShK structure, residues which are sensitive to degradation properties may be replaced or substituted. Thus, substitution of the Met residue at position 21 may be carried out to impart a stabilizing effect to oxidation. Additionally, substitution of the C-terminal acid function with an amide will impart stability to C-terminal corboxypeptidase enzymes. These two substitutions to the primary structure of ShK combined with the anionic moiety at the N-terminus have been synthesized to generate the most stable and selective Kv1.3 blocker. Nonhydrolyzable phosphate substitutions will also impart a stabilizing effect versus acid and basic hydrolysis of the phosphate as well as stability against phosphatase enzymes. The substitutions are summarized below. The acronyms used are defined as follows: Pmp=p-phosphonomethyl-Phenylalanine; Ppa=p-Phosphatityl-Phenylalanine and Nle=Norleucine.

Substitutions:
p-phospho-Tyr-Aeea-ShK-Nle21-Cys35-amide
p-Phosphono-methyl-Phenylalanine-Aeea-ShK-Nle21-Cys35amide (Pmp)
p-Phosphatityl-Phe-Aeea-ShK-Nle21-Cys35-amide (Ppa)
p-phospho-Tyr-Aeea-ShK-Nle21-Cys35-acid
p-Phosphono-methyl-Phenylalanine-Aeea-ShK-Nle21-Cys35acid (Pmp)
p-Phosphatityl-Phe-Aeea-ShK-Nle21-Cys35-acid (Ppa)

In addition to the nonhydrolyzable Pmp and Ppa, substitution of p-Phosphono(difluoro-methyl)-Phenylalanine (Pfp) and p-Phosphono-methylketo-Phenylalanine (Pkp) are also anionic substitutions, providing the following:
Pfp-Aeea-Shk-Nle21 Cys35 amide
Pkp-Aeea-ShK-Nle21-Cys35 amide
Pfp-Aeea-Shk-Nle21 Cys35 acid
Pkp-Aeea-ShK-Nle21-Cys35 acid.

Structures of the N-terminal substitutions are set forth in Appendix B. Other structures that are within the scope of the present invention are published in Beeton, C. et al., *Targeting Effector Memory T Cells with a Selective Peptide Inhibitor of Kv*1.3 *Channels for Therapy of Autoimmune Diseases*, Molecular Pharmacology, Vol. 67, No. 4, 1369-(2005), the entirety of which is expressly incorporated herein by reference and a complete copy of which is appended hereto as Appendix C.

Therapeutic Uses of ShK Analogs of the Present Invention

The present invention provides methods for treating or preventing certain disorders or diseases, such as T cell mediated disorders (e.g., autoimmune disorders, graft vs. host disease, prevention of rejection of organ transplants etc.), other inflammatory disorders, obesity and Type 2 diabetes, in human or animal subjects by administering to the subject a therapeutically effective (e.g., preventative or effective to reduce or eliminate symptoms or disease progression) amount of a pharmaceutically acceptable preparation consisting or comprising an ShK analog of the present invention (e.g., including but not limited to those listed in Table 1 hereabove). Any suitable route of administration (e.g., oral, rectal, intravenous, intramuscular, subcutaneous, intradermal, intranasal, topical, transmucosal, transdermal, by drug delivery implant, etc.) may be used. When used to prevent or treat a T cell mediated disorder, the dosage(s) will be sufficient to inhibit Kv1.3 channels on T cell membranes. In this regard, the ShK analogs of the present invention have the potential to be used to prevent or treat a wide variety of a T cell mediated autoimmune disorders. The following are some examples of some T cell mediated autoimmune diseases that may be prevented or treated by the methods of the present invention, categorized with respect to the target organ that is principally affected by each such disease:

| Nervous System: |
|---|
| Multiple sclerosis |
| Myasthenia gravis |
| Autoimmune neuropathies such as Guillain-Barré |
| Autoimmune uveitis |

-continued

| Blood: |
|---|
| Autoimmune hemolytic anemia |
| Pernicious anemia |
| Autoimmune |
| Thrombocytopenia |
| **Vascular:** |
| Temporal arteritis |
| Anti-phospholipid syndrome |
| Vasculitides such as Wegener's granulomatosis |
| Behcet's disease |
| **Skin:** |
| Psoriasis |
| Dermatitis herpetiformis |
| Pemphigus vulgaris |
| Vitiligo |
| **Gastrointestinal Tract:** |
| Crohn's Disease |
| Ulcerative colitis |
| Primary biliary cirrhosis |
| Autoimmune hepatitis |
| Bone resorption associated with periodontal disease |
| **Endocrine:** |
| Type 1 diabetes mellitus |
| Addison's Disease |
| Grave's Disease |
| Hashimoto's thyroiditis |
| Autoimmune oophoritis and |
| Orchitis |
| **Multiple Organs and/or Musculoskeletal System:** |
| Rheumatoid arthritis (RA) |
| Osteoarthritis (OA) |
| Systemic lupus erythematosus |
| Scleroderma |
| Polymyositis, dermatomyositis |
| Spondyloarthropathies such as |
| ankylosing spondylitis |
| Sjogren's syndrome |

Irrespective of the particular organ(s) affected, T-lymphocytes are believed to contribute to the development of autoimmune diseases. The currently available therapies for these diseases are largely unsatisfactory and typically involve the use of glucocorticoids (e.g. methylprednisolone, prednisone), non-steroidal anti-inflammatory agents, gold salts, methotrexate, antimalarials, and other immunosuppressants such as cyclosporin and FK-506. Also, another T cell mediated disorder that may be prevented or treated by the methods of the present invention is graft vs. host disease and/or rejection of transplanted organs. Indeed, the outcomes of organ transplant procedures have progressively improved with the development of refinements in tissue typing, surgical techniques, and more effective immunosuppressive treatments. However, rejection of transplanted organs remains a major problem. T-lymphocytes play a central role in the immune response and they are responsible, in large measure, for the rejection of many transplanted organs. They are also responsible for the so-called graft-versus host disease in which transplanted bone marrow cells recognize and destroy MHC-mismatched host tissues. Accordingly, drugs such as cyclosporin and FK506 that suppress T-cell immunity are used to prevent transplant rejection and graft-versus-host disease. Unfortunately, these T cell inhibiting drugs are toxic, with liver and renal toxicities limiting their use. Thus, the methods of the present invention may provide less toxic alternatives for the treatment or prevention of graft vs. host disease or transplant rejection. Also, inhibitors of the voltage gated Kv1.3 potassium channel have been shown to be especially effective in suppressing effector memory T cells and, thus, the methods of present invention may be particularly effective in preventing or treating diseases that are associated with effector memory T cells, such as; bone resorption and periodontal disease, psoriasis, rheumatoid arthritis, diabetes mellitus and multiple sclerosis. In addition to T cell mediated diseases, the Kv1.3 channel has been determined to regulate energy homeostasis, body weight and peripheral insulin sensitivity. Thus, the methods of the present invention may be used to treat other diseases and disorders that involve abnormal homeostasis, body weight and peripheral insulin sensitivity by inhibiting Kv1.3 channels on cell membranes, such other diseases and disorders include but are not necessarily limited to bone resorption in periodontal disease, Type 2 diabetes, metabolic syndrome and obesity.

Use of ShK Analogs of the Present Invention in Flow Cytometry

Further in accordance with the present invention there are provided methods for diagnosing T cell mediated disorders or otherwise sorting or distinguishing between various cell types in vitro using fluorophore tagged versions of ShK(L5) for use in flow cytometry alone, or in conjunction with class II tetramers that can detect autoreactive cells. Flow Cytometry is a flexible method for characterizing cells in suspension wherein fluorescence activated cell sorting is used to select living cells on the basis of characteristics measured by flow cytometry. The types of cellular features and functions that may be detected by flow cytometry include the expression of proteins outside and within cells, type of DNA content, viability and apoptosis, multiple drug resistance pump activity, enzyme activity, T-cell activation, T-cell receptor specificity, cytokine expression, phagocytosis and oxidative burst activity. Thus, in this method of the present invention, the amino acid residue attached to the ShK may incorporate a fluorophore tag for use in flow cytometry alone, or in conjunction with class II tetramers loaded with specific autoantigens that can detect autoreactive cells. Specific descriptions of the methods by which such flow cytometry may be carried out are described in Beeton, C., et al., *A Novel Fluorescent Toxin to Detect and Investigate Kv1.3 Channel Up-Regulation in Chronically Activated T Lymhocytes*; J. Biol. Chem., Vol. 278, No. 11, 9928-9937 (March 2003). In general, a flow cytometer uses focused laser light to illuminate cells as they pass the laser beam in a fluid stream. Light scattered by the cells and light emitted by fluorescent dyes attached to cells of interest are analyzed by several detectors and processed by a computer. Cells may be distinguished and selected on the basis of size and shape as well as by the presence of many different molecules inside and on the surface of the cells.

Examples of Potassium Channel Inhibiting Effects and Therapeutic Utility of ShK Analogs of the Present Invention ShK blocks the neuronal Kv1.1 channel and the Kv1.3 channel with roughly equivalent potency. Neurotoxicity is therefore a concern under circumstances that compromise the blood-brain-barrier and allow the entry of sufficient amounts of ShK to block Kv1.1 channels. Our strategy to design a Kv1.3-specific inhibitor was guided by our finding that ShK-F6CA containing fluorescein-6-carboxylate (F6CA) attached through a 20 Å-long Aeea linker to the N-terminus of ShK exhibited 80-fold selectivity for Kv1.3 over Kv1.1 (Beeton et al., 2003). Since F6CA can exist as a restricted carboxylate or also as a cyclized lactone, it was not clear whether ShK-F6CA's Kv1.3 specificity was due to the negative charge of F6CA, the hydrophobicity created by this large bulky fluorescein nucleus, potential planar-p electronic stacking or a combination of all of these potential contributions. To distinguish between these possibilities and with the intention of developing a non-fluorescent Kv1.3-selective inhibitor, we generated a series of 12 novel N-terminally-substituted ShK analogs to probe some of these interactions. By attaching tyrosine, phenylalanine or their derivatives (varying in charge, size and hydrophobicity) through an Aeea linker to the N-terminus of ShK, we could probe the effects of charge and hydrophobicity to gain insight into our selectivity enhancement seen with F6CA substitution.

Selective KV\v1.3 Inhibition over Kv1.1 Inhibition:

In the example shown in FIGS. 2A-2D, L-phosphotyrosine (L-pTyr) a negatively charged (net charge 2) post-translationally modified aromatic amino acid, was attached via the AEEA linker to ShK-Arg[1] to generate the novel analog ShK (L5). The ShK toxin and ShK(L5) were tested on Kv1.3 and Kv1.1 channels stably expressed in L929 cells. FIG. 2B shows the effects of ShK and ShK(L5) on Kv1.3 and Kv1.1 currents elicited by 200 ms depolarizing pulses from a holding potential of 80 mV to 40 mV. Both peptides reversibly blocked Kv1.3 and Kv1.1 in a dose-dependent manner with Hill coefficients of 1. $K_d$s were determined from the dose-response curves shown using Microcal Origin software. ShK blocked Kv1.3 ($K_d$=10±1 pM) and Kv1.1 ($K_d$=28±6 pM) with roughly equivalent potency as expected (FIG. 1C). In contrast, ShK(L5) was 100-fold selective for Kv1.3 ($K_d$=69±5 pM) over Kv1.1 ($K_d$=7.4±0.8 nM) (FIGS. 1B, 1C). The time course of Kv1.3 current block by ShK(L5) and its washout is shown in FIG. 1D. The time constant ($T_{ON}$) of ShK(L5) wash-in was 131±21 sec (n=7) while the time constant ($T_{OFF}$) for peptide wash-out was 150±28 sec (n=4). The $K_d$ (57±7 pM) calculated from the $K_{ON}$ ($15\times10^6 \pm 0.5\times10^6$ $M^{-1}$ $sec^{-1}$) and $K_{OFF}$ (0.0059±0.0013 $sec^{-1}$) values is consistent with the $K_d$ (69±5 pM) determined with Microcal Origin software.

Other ShK analogs were also tested on Kv1.3 and Kv1.1 channels. ShK(D5) containing D-phosphotyrosine (D-pTyr) was 35-fold selective for Kv1.3 over Kv1.1 but was an order of magnitude less potent than ShK(L5). ShK(L6) containing L-pTyr-monomethyl showed modest (11-fold) Kv1.3 specificity, while ShK analogs containing L-pTyr-dimethyl or L-Tyr were not selective for Kv1.3 over Kv1.1. Analogs that contained phenylalanine or its derivatives (varying in bulk, p electron density and charge) were modestly specific or not specific for Kv1.3 over Kv1.1. ShK(L5)'s 100-fold specificity for Kv1.3 over Kv1.1 is greater than that of ShK-F6CA (80-fold), ShK(D5) (35-fold), ShK-Dap[22] (33-fold) or any other ShK analog tested.

Applicants also assessed ShK(L5)'s specificity on a panel of 20 ion channels and these data are summarized in the following Table 2:

| Channels | $K_d$ of ShK(L5) [pM] |
|---|---|
| Kv1.1 | 7,000 ± 1,000 |
| Kv1.2 | 48,000 ± 7,000 |
| Kv1.3 (cloned) | 69 ± 5 |
| Kv1.3 (native) | 76 ± 8 |
| Kv1.4 | 137,000 ± 3,000 |
| Kv1.5 | 100,000 no effect |
| Kv1.6 | 18,000 ± 3,000 |
| Kv1.7 | 100,000 no effect |
| Kv2.1 | 100,000 no effect |
| Kv3.1 | 100,000 no effect |
| Kv3.2 | 20,000 ± 2,000 |
| Kir2.1 | 100,000 no effect |
| Kv11.1 (HERG) | 100,000 no effect |
| $K_{Ca}1.1$ | 100,000 no effect |
| $K_{Ca}2.1$ | 100,000 no effect |
| $K_{Ca}2.3$ | 100,000 no effect |
| $K_{Ca}3.1$ | 115,000 ± 5,000 |
| Nav1.2 | 100,000 no effect |
| Nav1.4 | 100,000 no effect |
| Swelling-activated T cell $Cl^-$ channel | 100,000 no effect |
| Cav1.2 | 100,000 no effect |

As may be appreciated from the data of Table 2 above, ShK(L5) blocked the Kv1.3 channel in T cells with a $K_d$ (76 pM) equivalent to its $K_d$ on the cloned channel (69 pM). It was 100-fold selective for Kv1.3 over Kv1.1, 260-fold selective over Kv1.6, 280-fold selective over Kv3.2, 680-fold selective over Kv1.2 and >1000-fold selective over all other channels tested. Importantly, it was 1600-fold Kv1.3-selective over KCa3.1, the calcium-activated $K^+$ channel that regulates activation of human naïve and $T_{CM}$ cells (Wulff et al., 2003). Native ShK was less selective than ShK(L5). ShK was 2.8-fold selective for Kv1.3 ($K_d$=10±1 pM) over Kv1.1 ($K_d$ 28±6 pM), 20-fold selective over Kv1.6 (200±20 pM), 500-fold selective over Kv3.2 ($K_d$=5,000±1,000 pM), and >1000-fold selective-over Kv1.2 (10±1 nM) and KCa3.1 ($K_d$=28±3 nM). Margatoxin, a peptide from scorpion venom that has been touted as a specific Kv1.3 inhibitor (Koo et al., 1997; Lin et al., 1993; Middleton et al., 2003) was also not specific. It was 5-fold selective for Kv1.3 (110±12 pM) over Kv1.2 ($K_d$=520±1 pM), 9-fold selective over Kv1.1 (10±1 nM) and >1000-fold selective over Kv1.6 and Kv3.2 ($K_d$>100 nM). Luteolin, a nutriceutical sold for autoimmune diseases (www.lutimax.com) on the basis of it being a Kv1.3 inhibitor (Lahey and Rajadhyaksha, 2004), blocked Kv1.3 weakly ($K_d$=65±5 mM) and exhibited no selectivity over Kv1.1 ($K_d$=77±5 mM), Kv1.2 ($K_d$=63±4 mM) or Kv1.5 ($K_d$=41±3 mM). ShK(L5)'s exquisite specificity for Kv1.3 together with its picomolar affinity for the channel makes it a potentially attractive immunosuppressant.

Preferential Suppression of Human $T_{EM}$ Cell Proliferation

Figure 3A:
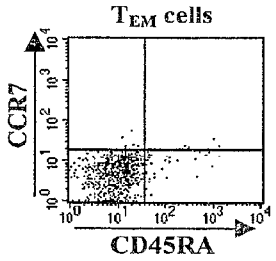
FIG. 3A is a graph showing staining intensities of CD45RA and CCR7 as determined by flow cytometry in the $CD3^+$-gated population of human PBMCs stained with antibodies against CD3, CD45RA and CCR7.
Figure 3B:
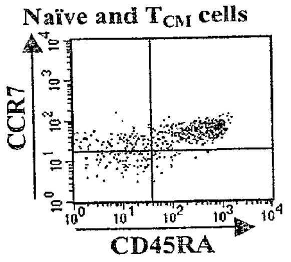
FIG. 3B is a graph showing staining intensities of CD45RA and CCR7 as determined by flow cytometry in the $CD3^+$-gated population in cells of a human $T_{EM}$ line stained with antibodies against CD3, CD45RA and CCR7.
Figure 3C:
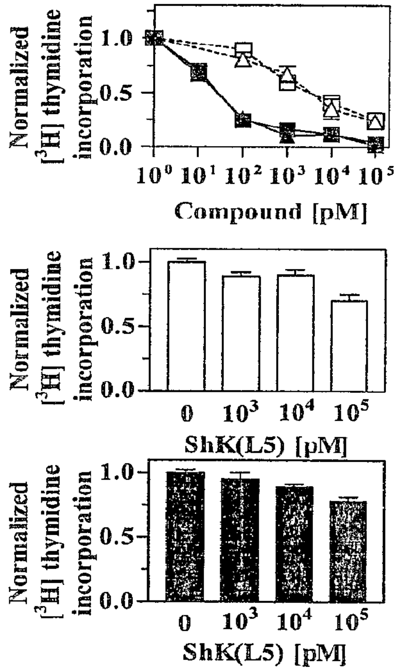
FIG. 3C is a graph showing the inhibitory effects of ShK (dark grey) and ShK(L5) (light grey) of [$^3$H] thymidine incorporation by PBMCs (open symbols, a mixture of naïve/$T_{CM}$ cells) and $T_{EM}$ cells (closed symbols) stimulated for 48 hours with anti-CD3 antibody.
Figure 3D:
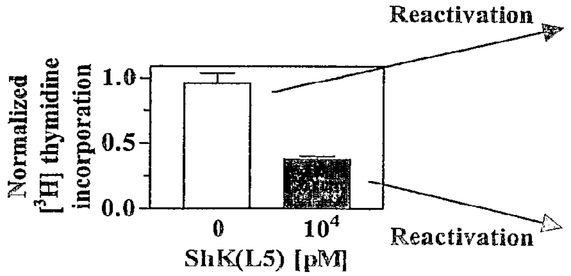
FIG. 3D is a graphic showing of pre-activated human PBMCs (naïve/$T_{CM}$ cells) that up-regulate KCa3.1 expression become resistant to ShK(L5) inhibition when reactivated with anti-CD3 antibody. These cells have previously been reported to become sensitive to the $K_{Ca}$3.1-specific inhibitor TRAM-34.

With reference to FIGS. 3A-3D, in order to assess ShK(L5)'s in vitro immunosuppressive activity, Applicants compared its ability to suppress anti-CD3 antibody-stimulated proliferation of human $T_{EM}$ cell lines versus human PBMCs that contain a mixture of naïve and $T_{CM}$ cells. Flow cytometry confirmed the cell surface phenotypes of the two populations studied. As seen in FIG. 3A, the $T_{EM}$ lines were >90% $CCR7^-$ CD45RA, while as shown in FIG. 3B the PBMCs contained 65% $CCR7^+CD45RA^+$(naïve) and 18% $CCR7^+CD45RA^-$ ($T_{CM}$) cells. FIG. 3C shows that ShK(L5) and ShK were 60-fold more effective in suppressing the proliferation of $T_{EM}$ cells ($IC_{50}$=~80 pM) compared with PBMCs ($IC_{50}$=5 nM, p<0.05). The lower sensitivity of PBMCs might be explained by a rapid up-regulation of KCa3.1 channels in naïve and $T_{CM}$ cells upon stimulation as has been reported previously (Ghanshani et al., 2000; Wulff et al., 2003). In keeping with this interpretation, PBMCs activated for 48 hours to up-regulate KCa3.1 expression, then rested for 12 hours, and re-activated with anti-CD3 antibody were completely resistant to ShK (L5) block, as shown in the upper row of FIG. 3D. PBMCs that had been suppressed by ShK(L5) during the first round of stimulation exhibited identical resistance to ShK(L5) when the cells were washed, rested and re-challenged with anti-CD3 antibody. These results corroborate earlier studies indicating that naïve and $T_{CM}$ cells escape Kv1.3 inhibitors by up-regulating KCa3.1 channels. Thus, ShK(L5) preferentially and persistently suppresses the proliferation of $T_{EM}$ cells.

Preferential Suppression of Rat $T_{EM}$ Cells Proliferation

As a preamble to evaluating ShK(L5)'s therapeutic effectiveness we examined its ability to suppress proliferation of a memory T cell line, PAS, that causes an MS-like disease in rats. As a control, Applicants used rat splenic T cells. To confirm the differentiation status of the two cell populations we assessed the expression of CD45RC, a marker of naïve T cells (Bunce and Bell, 1997). Rat splenic T cells were 76% $CD45RC^+$ (i.e. mainly naïve cells) whereas PAS cells were $CD45RC^-$ suggesting that they are memory cells, as shown in FIG. 4A. To determine whether PAS cells are in the $T_{EM}$- or the $T_{CM}$-state we examined Kv1.3 expression before and 48 hours after activation. $T_{EM}$ but not $T_{CM}$ cells are expected to significantly up-regulate Kv1.3 levels upon stimulation. With reference to FIG. 4B, patch-clamp experiments revealed a striking increase in Kv1.3 current amplitude after MBP-stimulation of PAS cells consistent with their being $T_{EM}$ cells.

As an independent measure of the number of Kv1.3 channels on PAS cells, we used ShK-F6CA, a fluorescently labeled ShK analog that has previously been reported to bind specifically to Kv1.3. The intensity of ShK-F6CA staining determined by flow cytometry reflects the number of Kv1.3 tetramers expressed on the cell surface. As seen in FIG. 4C, ShK-F6CA (10 nM) staining intensity increased with MBP-activation of PAS cells and an excess of unlabeled ShK(L5) (100 nM) competitively inhibited ShK-F6CA staining. As a final test, Applicants performed confocal microscopy on quiescent and MBP-stimulated PAS cells that had been fixed and stained with a Kv1.3-specific antibody. In keeping with data in FIGS. 4B and 4C, resting PAS T cells had a Kv1.3 staining intensity of 4.4±0.6 and this value increased to 10.6±2.3 ($p<0.005$) after antigen-induced activation (See FIG. 4D) showing augmentation in Kv1.3 protein expression following activation. Thus, MBP-activated PAS cells are $CD45RC^-$ $Kv1.3^{high}$ $T_{EM}$ cells whereas rat splenic T cells used in our experiments are predominantly in the naïve state.

MBP-triggered proliferation of PAS cells was suppressed ~1000-fold more effectively by ShK(L5) and ShK ($IC_{50}$=~80 pM) than mitogen-induced proliferation of rat splenic T cells (See FIG. 4E, $IC_{50}$~100 nM; $p<0.05$). These results corroborate the findings with human T cells described above. As seen in FIG. 4G ShK(L5) inhibited MBP-induced IL2 production by PAS cells (FIG. 4F), and exogenous IL2 partially overrode ShK(L5) suppression of PAS cell proliferation (FIG. 4G). Earlier studies reported similar findings with less specific Kv1.3 inhibitors on human, rat and mini-pig T cells. In summary, ShK(L5) is a powerful and selective inhibitor of human and rat $T_{EM}$ cells, and may therefore have therapeutic use in autoimmune diseases by preferentially targeting $T_{EM}$ cells that contribute to the pathogenesis of these disorders.

Circulating Half-Life and Stability

A patch-clamp bioassay was used to ascertain whether circulating levels of ShK(L5) following subcutaneous injection were sufficient to inhibit $T_{EM}$ cells. The results of these experiments are shown in FIGS. 5A-5F.

Serum samples from ShK(L5)-treated and control rats were tested for blocking activity on Kv1.3 channels. Control serum did not exhibit detectable blocking activity indicating an absence of endogenous channel blockers. To standardize the assay, known amounts of ShK(L5) were added to rat serum and these samples were tested on Kv1.3 channels. The spiked serum samples blocked Kv1.3 currents in a dose-dependent fashion ($K_d$ 77±9 pM) that was indistinguishable from ShK(L5)'s effect in the absence of serum (FIG. 4A). Levels of ShK(L5) in treated animals were determined by comparison with the standard curve. ShK(L5) was detectable in serum 5 minutes after a single subcutaneous injection of 200 mg/kg. Peak levels (12 nM) were reached in 30 minutes and the level then fell to a baseline of about 300 pM over 420 minutes. The disappearance of ShK(L5) from the blood could be fitted by a single exponential. The circulating half-life was estimated to be ~50 min.

Since the peak serum level after 200 mg/kg (12 nM) significantly exceeds the requirement for selective blockade of Kv1.3 channels and $T_{EM}$ cell function, we tested lower doses. After a single injection of 10 mg/kg the peak serum concentration of ShK(L5) reached ¯500 pM within 30 min (data not shown), a concentration sufficient to block >90% Kv1.3 but not affect Kv1.1. Repeated daily administration of this dose (10 mg/kg/day) resulted in steady-state levels of ~300 pM (measured 24 hours after injection, FIG. 5D), which is sufficient to cause 60-70% suppression of $T_{EM}$ cells with little effect on naïve/$T_{CM}$ cells. The "steady-state" level is unexpected given the estimated circulating half-life of ~50 min and indicates that ShK(L5) "accumulates" on repeated administration. To determine whether the "depot" was in the skin or elsewhere in the body, we measured blood levels of ShK(L5) 10 hours after rats received single intravenous or subcutaneous injections of 10 mg/kg ShK(L5). The peptide disappeared with the same time course following administration by either route (FIG. 5E) indicating that the skin is not responsible for the steady-state level of 300 pM ShK(L5) reached after a single 10 mg/kg daily injection (FIG. 5D), and the depot(s) resides elsewhere.

Figure 5A:
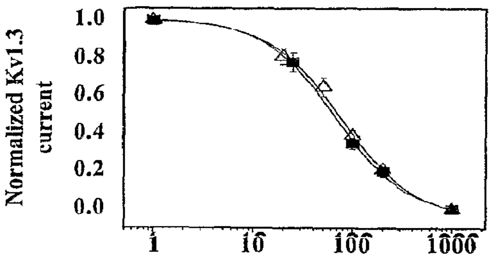
FIG. 5A is a graph showing Kv1.3 blocking activity of ShK(L5) as determined on Kv1.3 channels stably expressed in L929 cells.
Figure 5B:
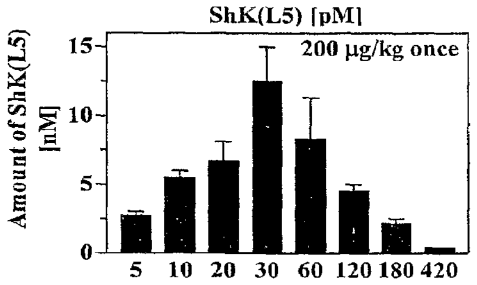
FIG. 5B is a graph showing blood levels of ShK(L5) at various times after a single subcutaneous injection of 200 mg/kg of ShK(L5) in four rats. Blood was drawn at the indicated times and serum was tested by patch-clamp to determine the amount of ShK(L5).
Figure 5C:
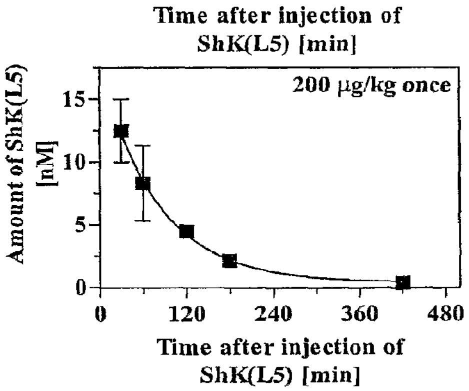
FIG. 5C is a graph of the data of FIG. 5B fitted to a single exponential decay indicating a half-life of approximately 50 minutes.
Figure 5D:
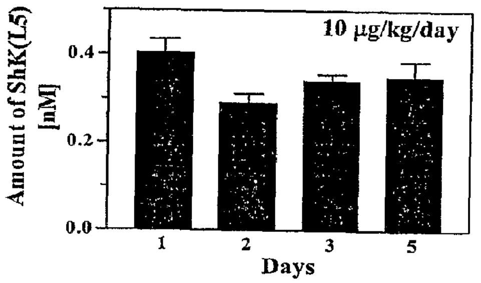
FIG. 5D is a graph showing blood levels of ShK(L5) in five Lewis rats receiving single daily subcutaneous injections of 10 μg/kg/day ShK(L5) for 5 days. Blood was drawn each morning (24 hours after the previous injection) and tested for blocking activity on Kv1.3 channels by patch-clamp.
Figure 5E:
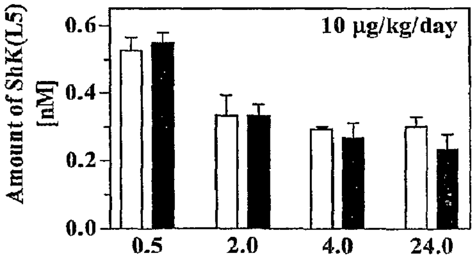
FIG. 5E is a graph showing serum levels of ShK(L5) in rats at various times following a single dose of 10 mg/kg ShK(L5) either subcutaneously (open bars; n=4) or intravenously (closed bars; n=4). Blood was drawn at the indicated times and serum was tested by patch-clamp to determine the amount of ShK(L5) in blood. ShK(L5) maintained a steady-state level of 300 pM in the blood almost 24 hours after a single subcutaneous injection. This concentration is sufficient to selectively inhibit the function of $T_{EM}$ cells.
Figure 5F:
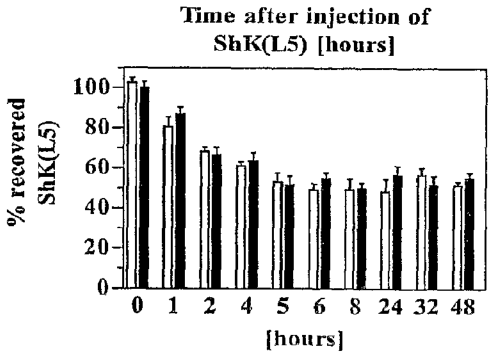
FIG. 5F is a graph showing the % recovery of ShK(L5) after a half-blocking dose of ShK(L5) was added to rat plasma or PBS containing 2% rat plasma and incubated at 37° C. for varying duration. Aliquots were taken at the indicated times and blocking activity determined on Kv1.3 channels. ShK (L5) is extremely stable in plasma.

The successful achievement of a steady-state level of 300 pM ShK(L5) following daily single injections of 10 mg/kg/day suggests that the peptide may be stable in vivo. To directly examine its stability we incubated ShK(L5) in rat plasma or in PBS containing 2% rat plasma at 37° C. for varying durations and then measured Kv1.3 blocking activity. In both sets of spiked samples (plasma and PBS) we observed a 50% reduction in Kv1.3-blocking activity in about 5 hours, presumably due to peptide binding to the plastic surface of the tube, and the level then remained steady for the next 2-days (FIG. 5F). As an added test of stability we compared the Kv1.3-versus Kv1.1-blocking activities of sera from ShK(L5)-treated rats. If ShK(L5) is modified in vivo, either by dephosphorylation of pTyr or cleavage of the Aeea-pTyr side-chain, it would yield ShK(L4) and ShK respectively, neither of which is selective for Kv1.3 over Kv1.1. Serum samples from ShK(L5)-treated animals exhibited the same selectivity for Kv1.3 over Kv1.1 as ShK(L5), indicating that the peptide does not undergo the modifications stated above. Taken together, these results indicate that ShK(L5) is remarkably stable in plasma and attains pharmacologically relevant serum concentrations after single daily subcutaneous injections of 10 mg/kg.

Nontoxicity

Applicants conducted several in vitro and in vivo tests to determine if ShK(L5) exhibits any toxicity. The results of these studies are summarized in Appendix A. Human and rat lymphoid cells incubated for 48 hours with a concentration (100 nM) of ShK(L5)>1200 times greater than the Kv1.3 half-blocking dose or the $IC_{50}$ for $T_{EM}$ suppression (70-80 pM), exhibited minimal cytotoxicity. The same high concentration of ShK(L5) was negative in the Ames test on tester strain TA97A suggesting that it is not a mutagen. Both in vitro tests failed to detect any significant toxicity.

Drug-induced blockade of Kv11.1 (HERG) channels has contributed to major cardiac toxicity and the withdrawal of several medications from the market. ShK(L5) has no effect on Kv11.1 channels at 100 nM (>1430-fold the $K_d$ for Kv1.3), and Applicants' chosen therapeutic regimen (10 mg/kg/day, 300 pM steady-state circulating level) should therefore not cause cardiotoxicity. As a further test, Applicants performed heart rate variability analysis in conscious rats administered vehicle (PBS+2% rat serum) on day-1, followed by 10 mg/kg/day ShK(L5) on day-2. ShK(L5) had no effect on heart rate or the standard HRV (heart rate variability) parameters in both time and frequency domains (Task force of the European Society of Cardiology and the North American Society of Pacing Electrophysiology, 1996).

Encouraged by the acute toxicity experiments, Applicants performed a sub-chronic toxicity study in which rats were administered daily subcutaneous injections of 10 mg/kg ShK(L5) or vehicle for 2 weeks (n=6 in each group). ShK(L5)-treated animals gained weight to the same degree as rats receiving vehicle (Appendix A). Hematological and blood chemistry analysis showed no difference between ShK(L5)- and vehicle-treated rats, and flow cytometric analysis revealed no differences in the proportions of thymocyte or lymphocyte subsets (Appendix A). Collectively, these studies suggest that ShK(L5) is safe.

To determine the therapeutic safety index, we administered a 60-fold higher dose (600 mg/kg/day) of ShK(L5) to healthy rats for 5 days and observed no clinical signs of toxicity, and no toxicity was seen when healthy rats received a single injection of 1000 mg/kg ShK(L5). The situation is less sanguine when the blood-brain-barrier is compromised as happens in EAE and MS. Rats with EAE that received ShK(L5) 10 mg/kg/day for 10 days showed no signs of toxicity. In contrast, forty percent of rats (5/12) administered 600 mg/kg/day for five days died on the fifth day when they developed clinical signs of EAE (extrapolated $LD_{50}$=750 mg/kg/day). Since the peak concentration of ShK(L5) in the serum (12 nM) after administration of a single injection of 200 mg/kg is sufficient to block >50% of Kv1.1 channels, toxicity observed in EAE rats administered 600 mg/kg/day ShK(L5) is likely due to the ingress into the brain of sufficient amounts of ShK(L5) to block Kv1.1. Thus, the effective therapeutic safety index of ShK(L5) is well in excess of 100 in situations where the blood-brain barrier is not compromised (as seen in autoimmune diseases that do NOT affect the central nervous system (CNS)), whereas the therapeutic safety index is 75 when the blood-brain barrier is breached.

Prevention of DTH and Acute Adoptive EAE

Figure 6A:
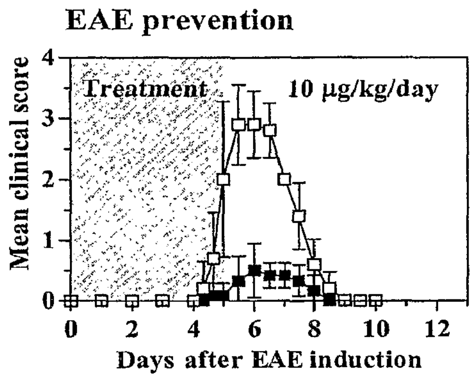
FIG. 6A is a graph showing scored prevention of EAE. PAS T cells were activated in vitro, washed, and injected intraperitoneally on day 0. Clinical scoring of EAE: 0=no clinical signs, 0.5=distal limps tail, 1=limp tail, 2=mild paraparesis or ataxia, 3=moderate paraparesis, 4=complete hind limb paralysis, 5=4+incontinence, 6=death. Rats (n=6/group) were injected subcutaneous with vehicle alone (n=6) or ShK (L5) (n=6; 10 mg/kg/day) from day 0 to day 5.
Figure 6B:
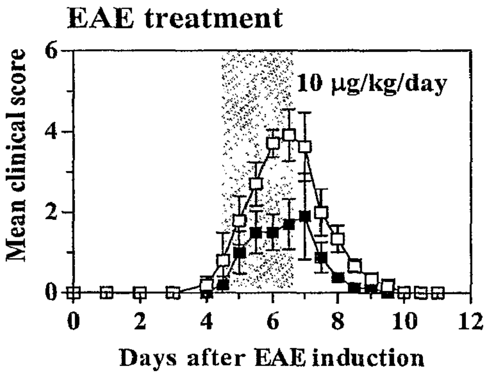
FIG. 6B is a graph showing scored treatment of EAE. PAS T cells were activated in vitro, washed, and injected intraperitoneally on day 0. Treatment with ShK(L5) at 10 mg/kg/day was started when rats developed clinical signs of EAE and was continued for 3 days.
Figure 6C:
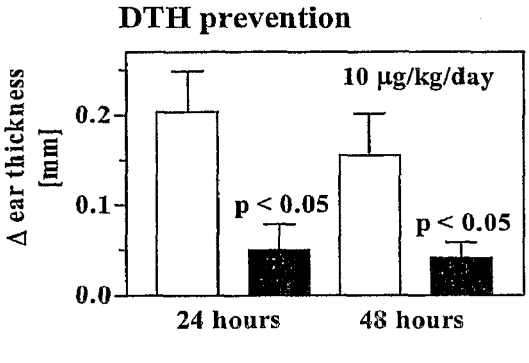
FIG. 6C is a graph showing ear thickness as an indicator of DTH reaction elicited against ovalbumin in rats. Animals (n=6/group) were treated with ShK(L5) 10 mg/kg/day for 2 days, after which ear swelling was measured. Statistical analysis was carried out using the Mann-Whitney U-test.

With reference to FIGS. 6A-6C, ShK(L5) was evaluated for immunosuppressive activity in vivo in two animal models. Applicants tested its ability to prevent and treat acute EAE induced by the transfer of MBP-activated PAS $T_{EM}$ cells into Lewis rats, as well as to suppress the DTH reaction mediated by $T_{EM}$ cells. PAS cells were activated with MBP for 48 hours in vitro and then adoptively transferred (6–8×$10^6$ viable cells) into Lewis rats. For the prevention trial, rats then received subcutaneous injections of saline (controls) or ShK(L5) (10 μg/kg/day) for 5 days. In the first prevention trial control rats developed mild EAE (mean maximum clinical score 2.0±1.2) with an average onset of 5.6±0.6 days (not shown). ShK(L5) reduced disease severity (mean maximum clinical score 0.7±0.6, $p<0.05$). In the second prevention trial, control rats developed more severe EAE (mean maximum clinical score 3.2±0.4) with a mean onset of 4.8±0.4 days (FIG. 6A). ShK (L5) significantly reduced disease severity (mean maximum clinical score 0.6±0.4, $p<0.007$) but did not significantly delay disease onset (5.5±0.7 days; $p=0.07$). No signs of toxicity were noted in these studies.

In the treatment trial (FIG. 6B) rats were injected with MBP-activated PAS cells, administered saline or 10 μg/kg/day ShK(L5) when they initially developed signs of EAE (limp tail, hunched posture and loss of 6% or more of their weight over 24 hours) and therapy was continued for three days. Clinical signs of EAE peaked on day 6 in the control group (score=3.9±0.7) and on day 7 in the treated group (score=1.9±0.9; $p<0.05$).

As an independent assessment of ShK(L5)'s immunosuppressive activity in vivo, Applicants also examined its effectiveness in inhibiting the DTH reaction that is mediated predominantly by skin-homing $T_{EM}$ cells. Lewis rats immunized with ovalbumin and adjuvant were challenged 7 days later with ovalbumin in one ear and saline in the other ear. Rats then received injections of saline (controls) or ShK(L5) (10 μg/kg/day) and ear thickness was measured as an indication of DTH. All control rats developed ear swelling 24 and 48 hours after ovalbumin challenge while the DTH reaction was substantially milder in ShK(L5)-treated animals (FIG. 6C). Thus, ShK(L5) inhibits the $T_{EM}$-mediated DTH response, and prevents and ameliorates severe adoptive EAE induced by myelin-activated $T_{EM}$ cells.

Figure 7A:
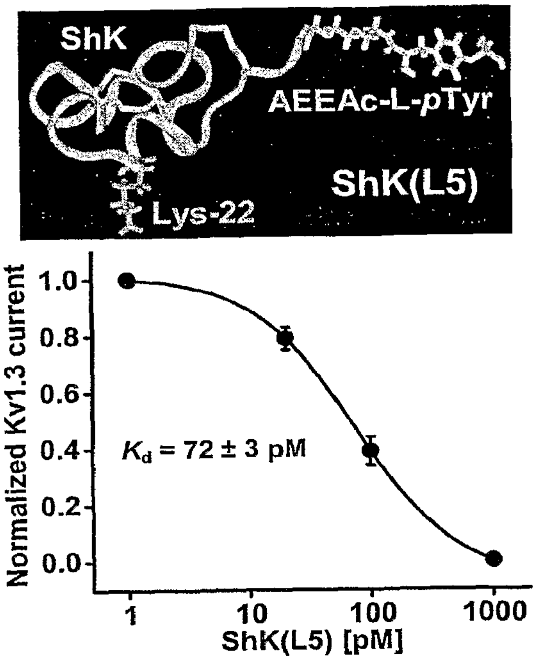
FIG. 7A shows the ShK(L5) structure and a graph showing inhibition of Kv1.3 channels in $T_{EM}$ cells as a function of ShK(L5) concentration. Each data-point represents mean of three determinations.
Figure 7B:
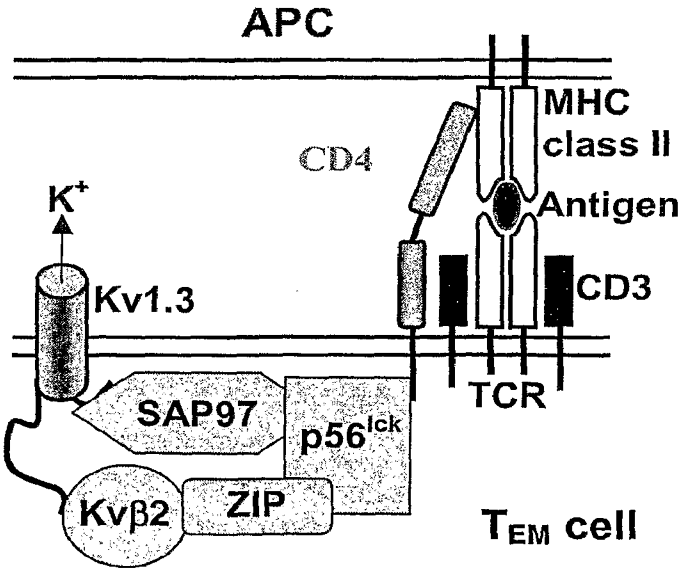
FIG. 7B is a diagram of Kv1.3-containing signaling complex.
Figure 7C:
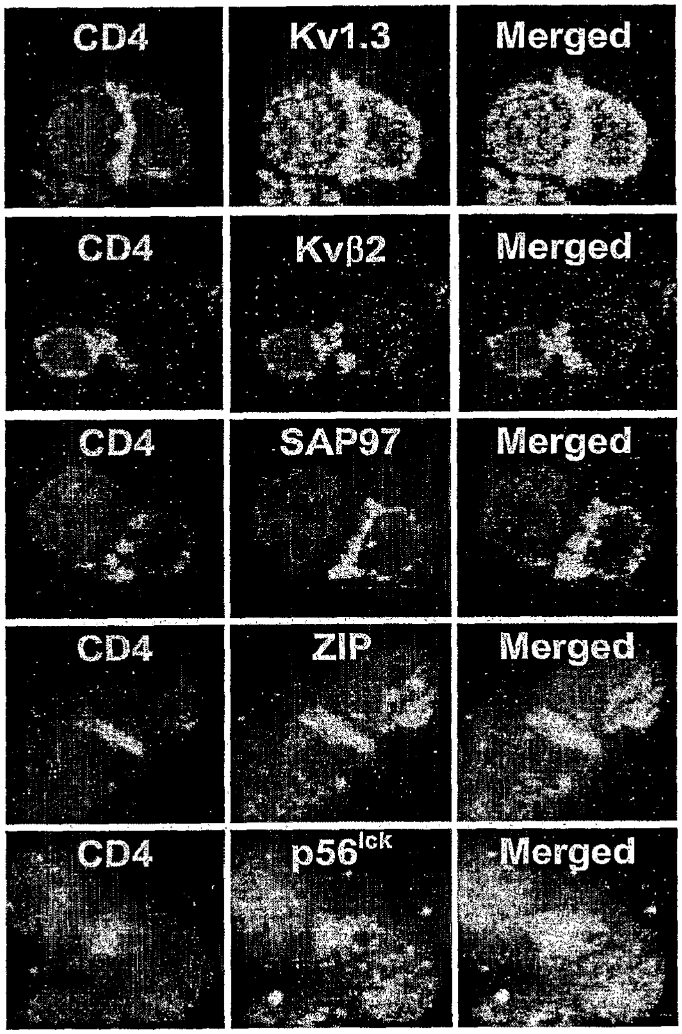
FIG. 7C shows co-localization of CD4, Kv1.3, Kvβ2, SAP97, ZIP and p56$^{lck}$ at IS.
Figure 7D:
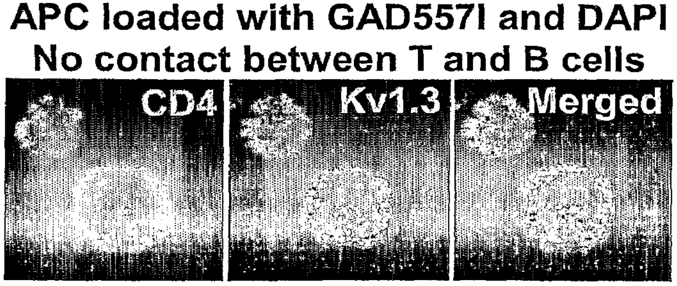
FIG. 7D shows CD4 and Kv1.3 staining in absence of visible $T_{EM}$-APC contact.
Figure 7E:
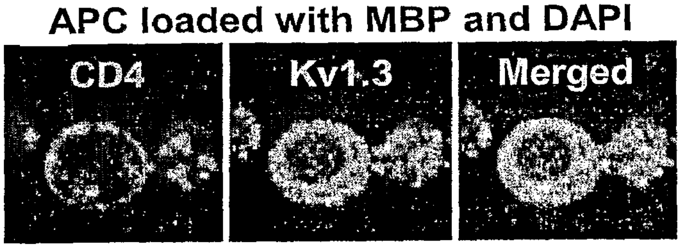
FIG. 7E shows CD4 and Kv1.3 staining in GAD65-specific $T_{EM}$ cells exposed to MBP-loaded APCs.
Figure 7F:
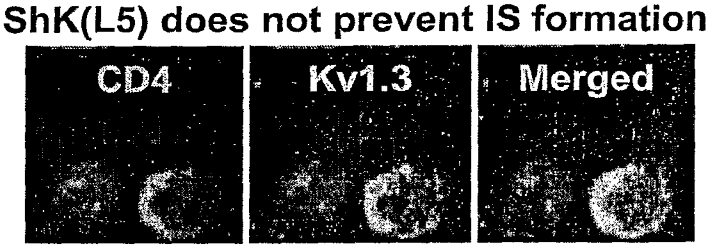
FIG. 7F shows that ShK(L5) 100 nM does not prevent IS formation.
Figure 7G:
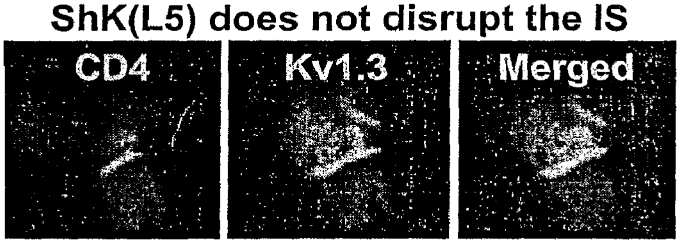
FIG. 7G shows that ShK(L5) 100 nM does not disrupt the IS.

Kv1.3 Clusters at the is During Antigen Presentation but $K^+$ Efflux Through Kv1.3 is not Required for IS Formation or Stability Referring to FIGS. 7A-7G, ShK(L5), a highly selective Kv1.3 inhibitor (21), blocked Kv1.3 currents in GAD65-specific $T_{EM}$ cells with a $K_d$ of 72±3 pM. We used ShK(L5) as a pharmacological probe to define those steps in $T_{EM}$ cell activation that require Kv1.3 function. Biochemical studies have shown that Kv1.3 and Kvb2 belong to a signaling complex that includes SAP97 (Synapse-Associated-Protein-97), ZIP(PKC-zeta-interacting-protein, $p56^{lck}$-associated-p62-protein, A170), $p56^{lck}$ and CD4 (FIG. 7B). The existence of this complex in human $T_{EM}$ cells is supported by Applicants' results showing co-capping of Kv1.3, Kvb2, SAP97, ZIP and $p56^{lck}$ with CD4. Furthermore, FRET (fluorescence energy transfer) studies show Kv1.3 in close proximity to CD3 in Kv1.3-transfected human T cells, and the channel preferentially localizes at the point of contact between Kv1.3-transfected human cytotoxic T cells and their targets. Since CD4 traffics to the IS, the zone of contact between T cells and antigen presenting cells (APC), it is possible that Kv1.3 and other proteins in the signaling complex also localize at the IS during antigen-presentation. To test this idea, GAD65-specific $Kv1.3^{high}$ $T_{EM}$ clones from a T1DM patient were incubated with HLA-matched APCs that had been loaded with GAD65 557I peptide and stained with DAPI to aid visualization. After 20 min, APC-$T_{EM}$ conjugates were immunostained for proteins in the signaling complex. CD4 co-localized at the IS with Kv1.3, Kvb2, SAP97, ZIP and $p56^{lck}$. In the absence of APC-$T_{EM}$ contact, CD4 and Kv1.3 were distributed throughout the cell. Furthermore, CD4 and Kv1.3 failed to localize at points of contact when GAD65-specific $T_{EM}$ cells were exposed to APCs loaded with MBP (an irrelevant antigen), verifying that IS-clustering is antigen-specific. Thus in GAD65-specific $T_{EM}$ cells, a Kv1.3-containing signaling complex traffics together with CD4 to the IS during antigen-presentation, suggesting that Kv1.3 is an integral component of the machinery that transduces signals in $T_{EM}$ cells. Based on these studies, ShK(L5) at a concentration that blocks approximately 99% of Kv1.3 channels (100 nM) did not prevent IS-clustering and did not disrupt the IS once formed, indicating that $K^+$ efflux through Kv1.3 channels is unnecessary for IS formation or stability.

Suppression of Human $T_{EM}$ Cells

Figure 8A:
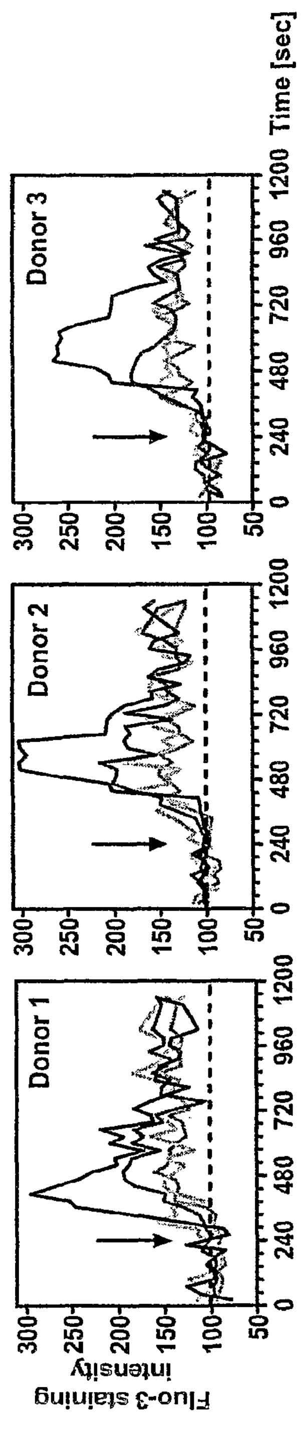
FIG. 8A is a graphic showing of calcium signaling in GAD-specific $T_{EM}$ cells from three T1DM patients triggered by anti-CD3+cross-linking secondary antibodies (arrow) in the absence (black) or presence of ShK(L5) 0.1 nM (dark grey), 1 nM (medium grey) or 100 nM (light grey).
Figure 8B:
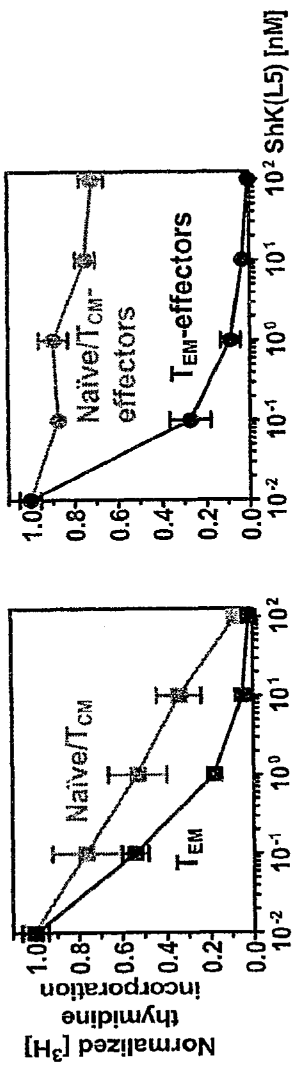
FIG. 8B is a graph showing [$^3$H]-thymidine incorporation by naïve/$T_{CM}$ and $T_{EM}$ cells (left) and naïve/$T_{CM}$-effectors and $T_{EM}$-effectors from patients with T1DM and RA (right). $T_{EM}$ cells: GAD65-activated $T_{EM}$ clones from three T1DM patients and anti-CD3 antibody activated SF-$T_{EM}$ cells from three RA patients. Naïve/$T_{CM}$ cells: anti-CD3 antibody-activated PB-naïve/$T_{CM}$ cells from the same three RA patients.
Figure 8C:
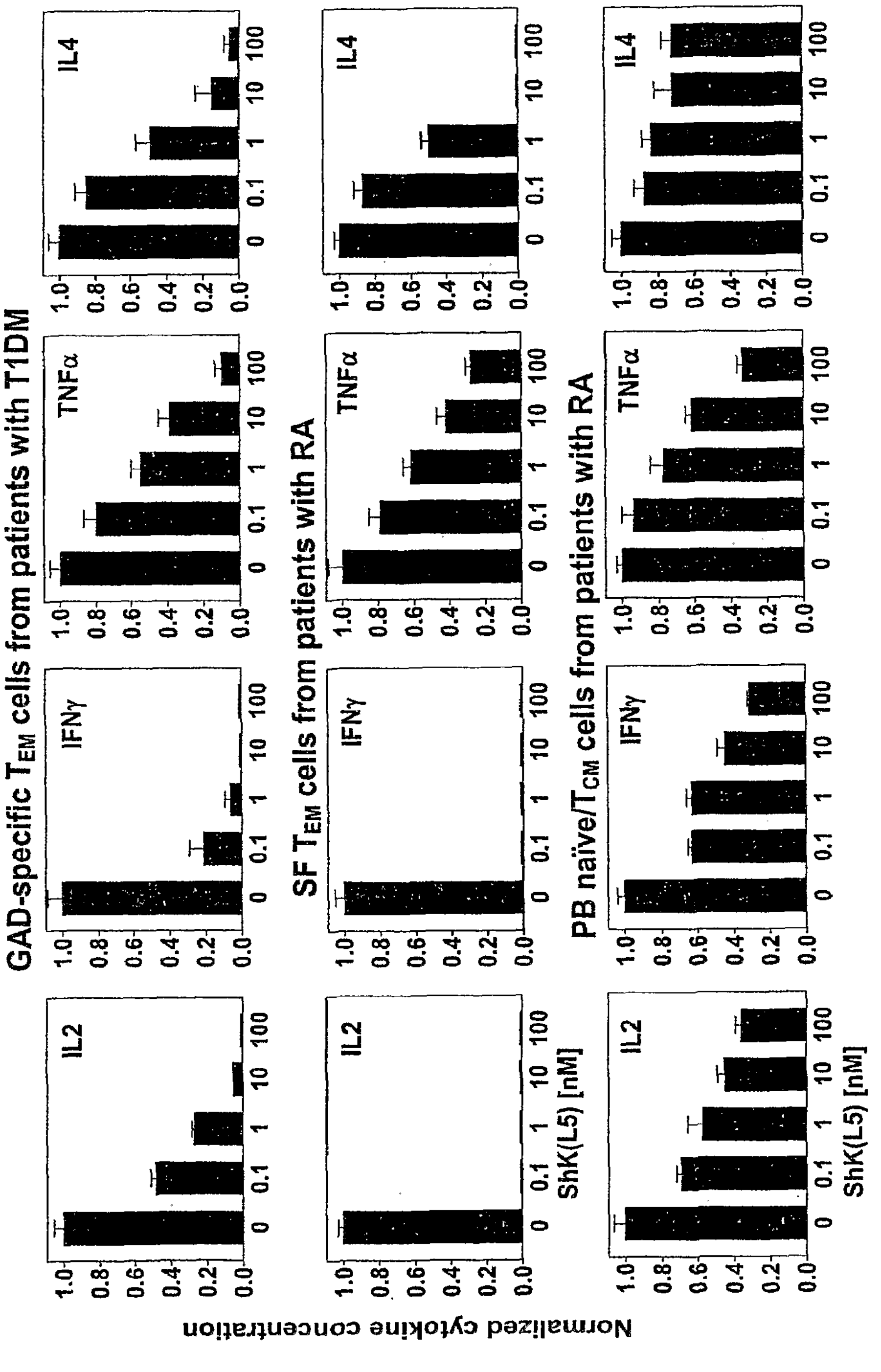
FIG. 8C is a series of bar graphs showing Cytokine production by the $T_{EM}$ and naïve/$T_{CM}$ cells used in FIG. 8B.
Figure 8D:
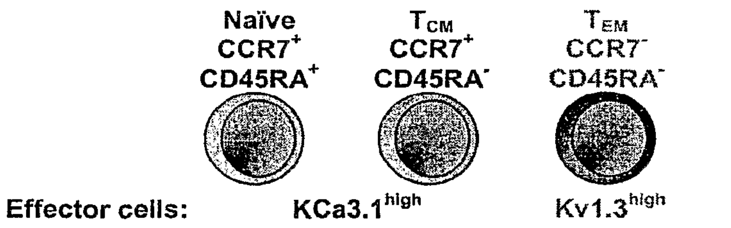
FIG. 8D shows the phenotype of disease-relevant and disease-irrelevant autoreactive T cells in MS, T1DM and RA.
Figure 8E:
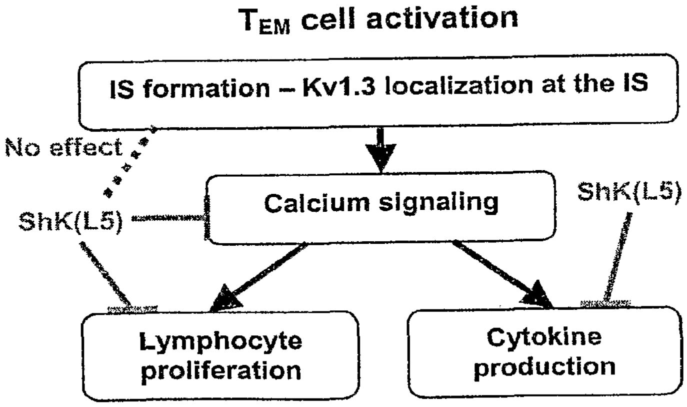
FIG. 8E is a diagram showing the manner in which ShK (L5) inhibits calcium signaling, lymphocyte proliferation and cytokine production but not IS formation.

With reference to FIGS. 8A-8E, ShK(L5) inhibited calcium signaling in $T_{EM}$ cells, an early and essential step in T cell activation. GAD65-specific $T_{EM}$ clones from T1DM patients were loaded with the calcium indicator dye Fluo3, pre-incubated in medium alone or with increasing concentrations of ShK(L5) and imaged by flow cytometry before and after the addition of an activating anti-CD3 antibody and a cross-linking secondary antibody. Peak calcium rise occurred in 242±35 seconds after stimulation and was blocked by ShK(L5) with an $IC_{50}$ of ~200 pM (FIG. 8A). ShK(L5) was 10-fold more effective in suppressing [$^3$H]-thymidine-incorporation by autoreactive $T_{EM}$ cells from T1DM and RA patients compared with naïve/$T_{CM}$ cells from these patients (FIG. 8B, left). In a second set of experiments (FIG. 8B, right), RA-SF and RA-PB T cells were activated with anti-CD3 antibody for 48 hours to generate "$T_{EM}$-effectors" and "naïve/$T_{CM}$-effectors" respectively. Cells were rested overnight in medium, re-stimulated with anti-CD3 antibody in the presence or absence of ShK(L5) for a further 48 hours and [$^3$H]-thymidine incorporation was measured. RA-SF-$T_{EM}$-effectors retained their sensitivity to ShK(L5) inhibition, whereas RA-PB-naïve/$T_{CM}$-effectors were resistant to Kv1.3 blockade (FIG. 8B, right), most likely because they up-regulate the calcium-activated KCa3.1/IKCa1 channel, which substitutes for Kv1.3 in promoting calcium entry. ShK(L5) profoundly suppressed the production of interleukin 2 (IL2) and interferon-g (IFN-g) by $T_{EM}$ cells from T1DM and RA patients, whereas IL2 and IFN-g production by naïve/$T_{CM}$ cells from these patients was less affected (FIG. 8C). The production of tumor necrosis factor-a and interleukin 4 by both $T_{EM}$ cells and naïve/$T_{CM}$ cells was less sensitive to ShK (L5) (FIG. 8C).

Verification of Rat Model of Delayed Type Hypersensitivity (DTH) Caused by Effector Memory T Cells.

Figure 9:
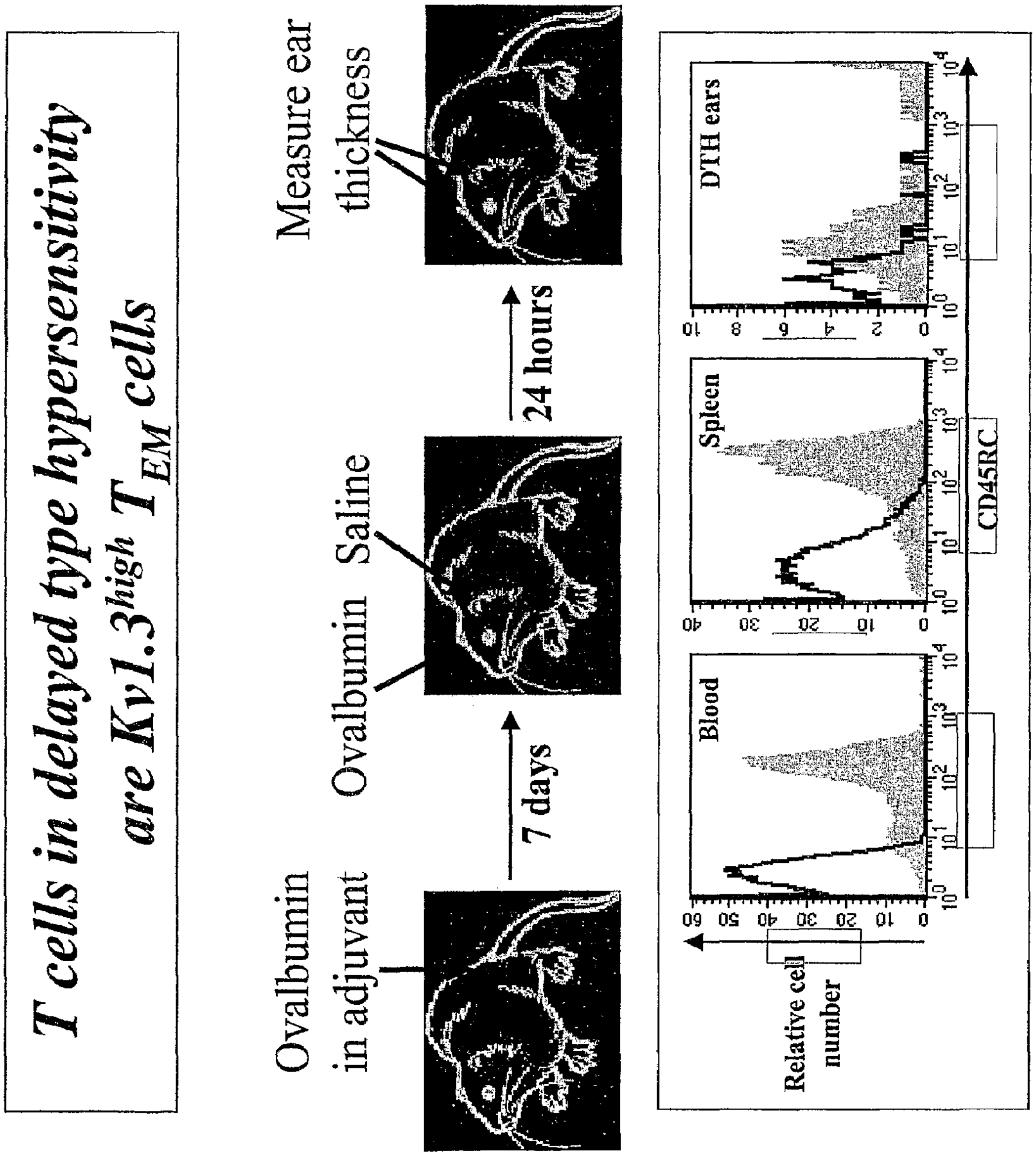
FIG. 9 is a diagram representing a rat model of delayed type hypersensitivity (DTH) caused by effector memory T cells.

As shown in FIG. 9, rats were immunized with ovalbumin (OVA) in adjuvant. They were challenged in one ear 7 days later with OVA and in the other ear with saline. Ear swelling was measured 24 h later as a sign of delayed type hypersensitivity (DTH). The FACS histograms shown in FIG. 9 indicate that T cells in the ears challenged with OVA are CD45RC-negative memory cells while T cells in the blood and spleen of the same rats are mostly naive T cells.

Figure 10:
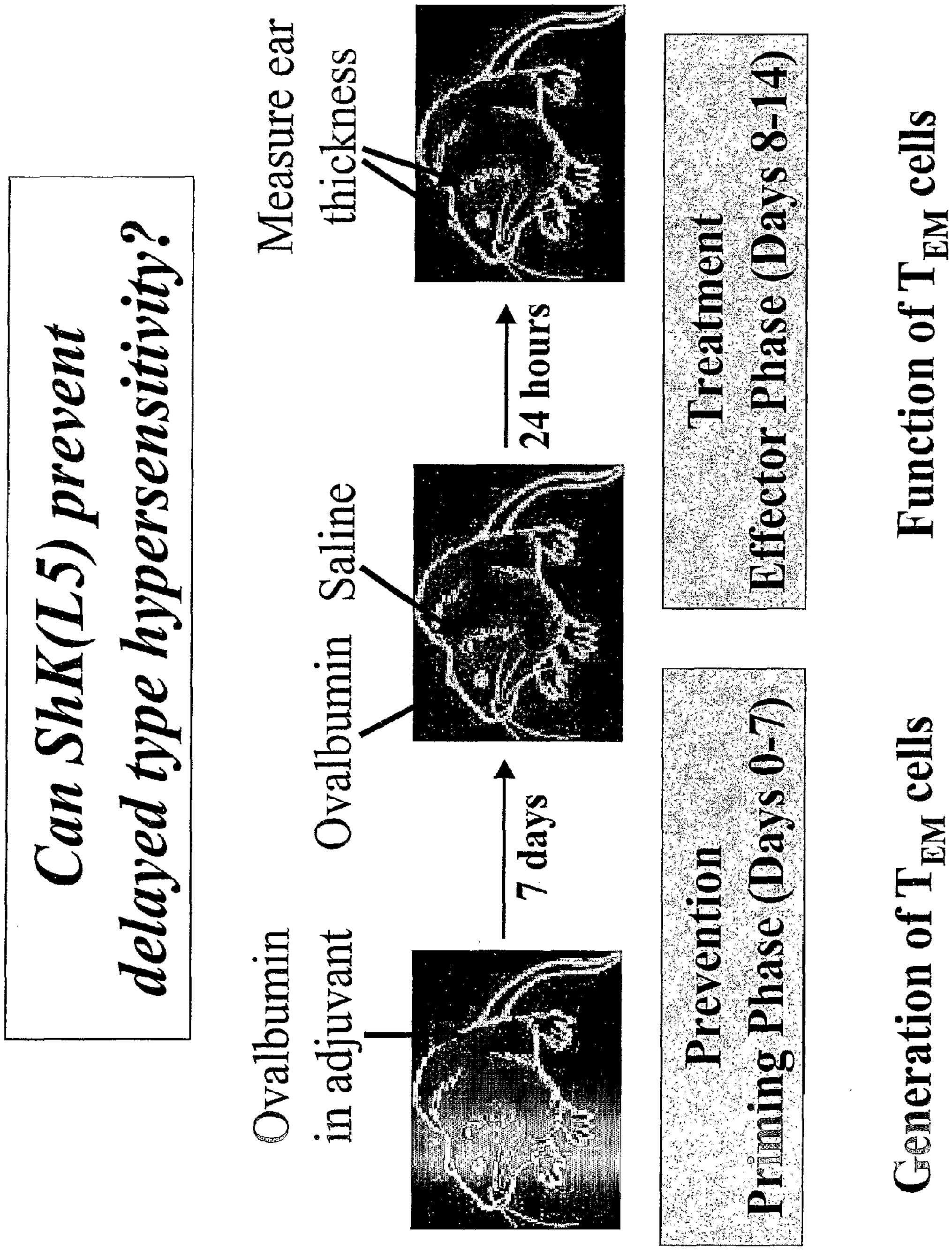
FIG. 10 is a diagram showing a treatment protocol for ShK(L5) in a rat model of delayed type hypersensitivity (DTH) caused by effector memory T cells

Treatment Protocol for Shk(L5) in a Rat Model of Delayed Type Hypersensitivity (DTH) Caused by Effector Memory T Cells As shown in FIG. 10, rats received ShK(L5) 10 μg/kg/day as a subcutaneous injection either from day 0 to day 7 (during the priming phase) to prevent the differentiation of naiv cells to effector memory TEM cells, or during the effector phase after challenge to the ear with ovalbumin to prevent the function of the TEM cells.

Figure 11:
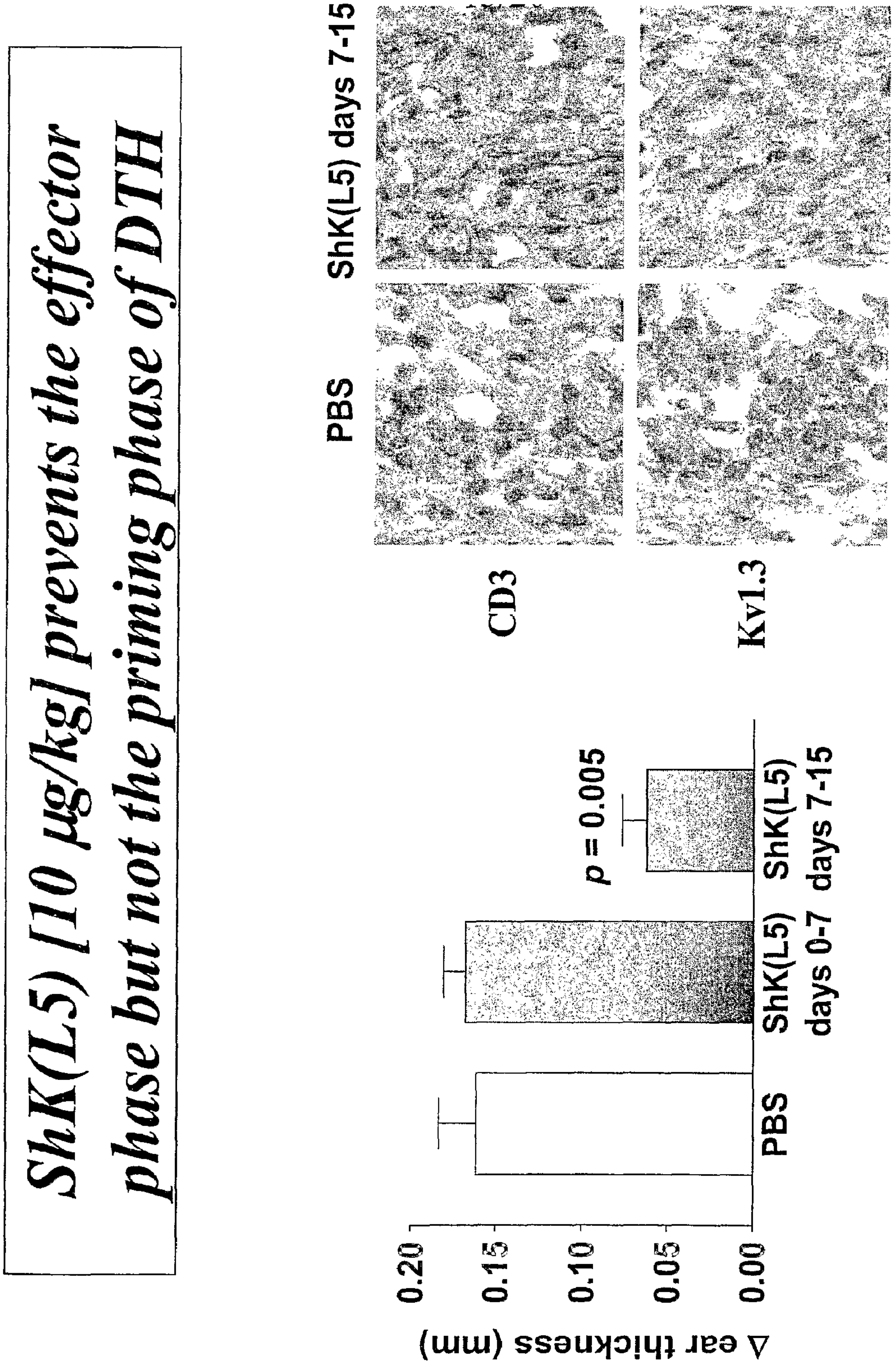
FIG. 11 is a diagram representing specific suppression of effector memory responses in vivo in rats by ShK(L5) without impairing the function of naive and central memory T cells or B cells.

Shk(L5) Specifically Suppresses Effector Memory Responses in Vivo in Rats without Impairing the Function of Naive and Central Memory T Cells or B Cells As shown in FIG. 11, control rats developed ear swelling i.e. a positive DTH response. ShK(L5) was NOT effective in suppressing DTH when administered during the priming phase, indicating that it did not suppress the differentiation of naive and central memory T cells into effector memory cells. ShK(L5) suppressed DTH when administered during the effector phase indicating that it either prevented the ability of effector memory T cells to reach the ear and/or suppressed the activation of effector memory T cells. The first possibility was excluded because the number of T cells in the ears of ShK (L5)-treated rats was the same as in the ears of rats given the vehicle. ShK(L5) suppressed effector memory T cell activation in the ear because these T cells were Kv1.3-negative, while the memory T cells in the ears of vehicle-treated animals were Kv1.3 positive. IgM and IgG B-cell responses in these animals was also not affected.

Figures 12A, 12B:
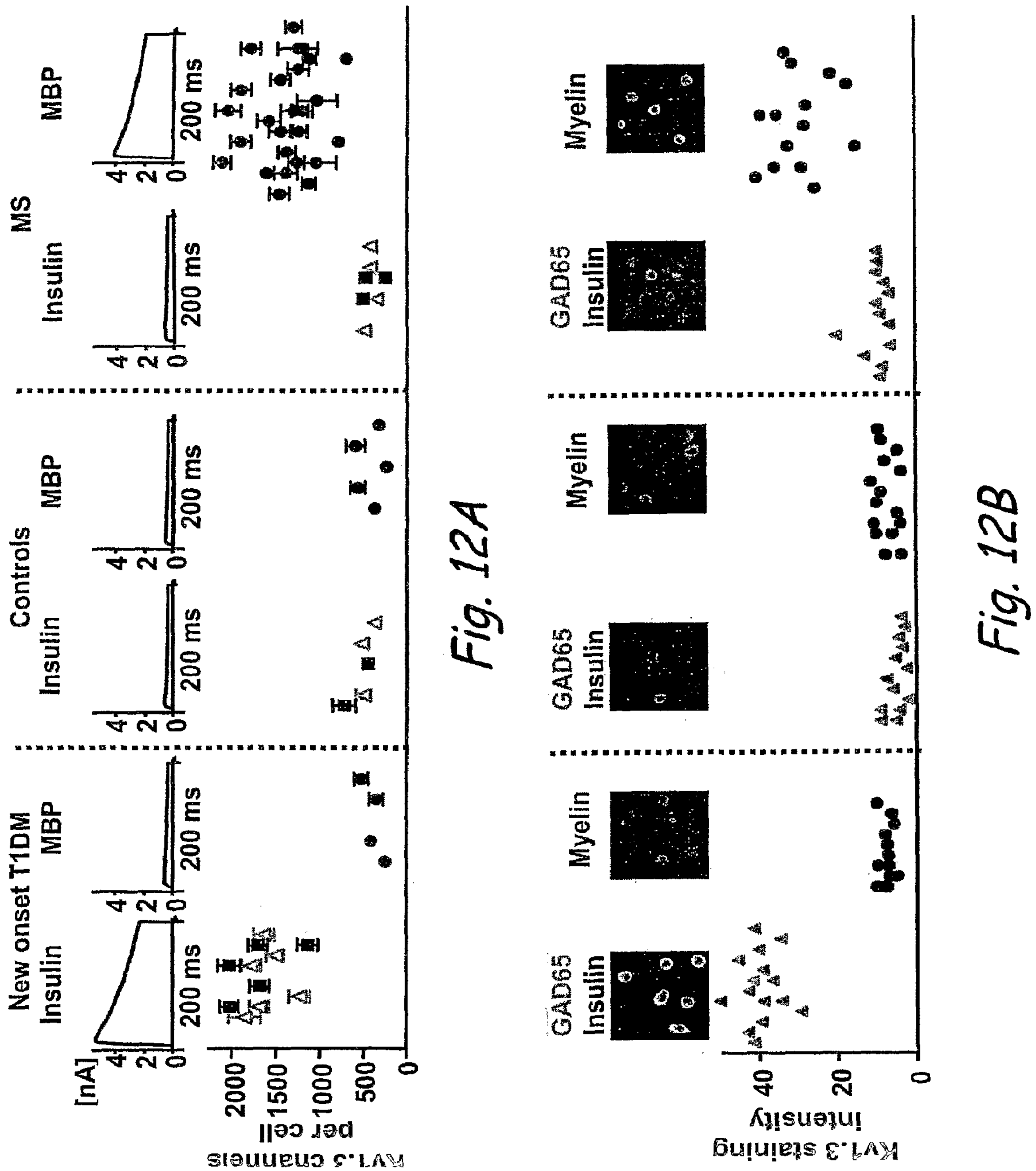
FIG. 12A shows Kv1.3 currents (top) and channel number/cell (bottom) in GAD65-, insulin and myelin-specific T cells from patients with new onset type-1 diabetes mellitus (T1DM), health controls and patients with multiple sclerosis.
FIG. 12B shows Kv1.3 staining (top) and fluorescence intensities of individual T cells (bottom) from these patients.
Figure 12C:
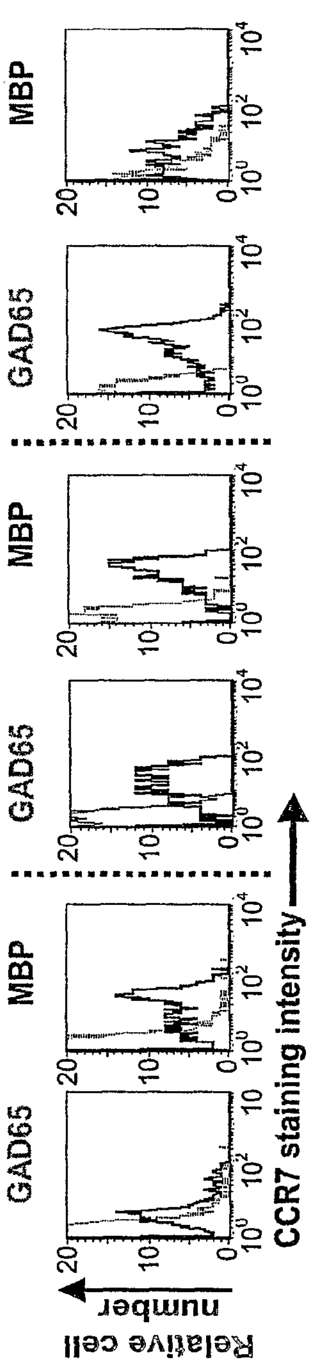
FIG. 12C shows graphs of relative cell number vs. CCR7 staining intensity. Cells expressing high levels of Kv1.3 are CCR7-negative i.e. they are $T_{EM}$-effectors. Cells expressing low levels of Kv1.3 are CCR&-positive i.e. they are either naïve or $T_{CM}$ cells

Kv1.3 Expression in T Cells Specific for GAD65/555-567, Insulin/9-23- and Myelin Antigens from Patients with T1DM or MS and Healthy Controls FIG. 12A shows Kv1.3 currents (top) and channel number/cell (bottom) from antigen-specific T cells from patients with new onset type-1 diabetes mellitus, health controls and patients with multiple sclerosis. Each data-point represents the mean±SEM from 20-50 cells from 2-4 T cell lines from a single donor measured 48 hours after the third antigen stimulation. Due to the low frequency of T cells specific for insulin and GAD65 in the blood of T1DM patients and controls, we amplified these populations by generating short-term autoantigen-specific $CD4^+$ T cell lines using the split-well method. As controls, we generated T cell lines specific for the irrelevant autoantigen myelin basic protein (MBP) that is implicated in MS but not T1DM. Following the third antigenic stimulation, Kv1.3 currents were measured by whole-cell patch-clamp in activated cells with a membrane capacitance greater than 4 pF (cell diameter≧11 μm). Representative Kv1.3 currents and Kv1.3 channel-numbers/T cell are shown in FIG. 12A. The currents displayed biophysical and pharmacological properties characteristic of Kv1.3. T cells specific for insulin (9-23) or GAD65 (555-567) from patients with new onset T1DM displayed large Kv1.3 currents and expressed high numbers of Kv1.3 channels, whereas disease-irrelevant MBP-specific T cells from these patients were $Kv1.3^{low}$ (p=0.001). For comparison we have plotted our published Kv1.3 data on MS patients in whom the opposite pattern was observed. In MS patients, T cells specific for MBP or myelin oligodendrocyte glycoprotein (peptide 35-55) or proteolipid protein (peptide 139-151) were $Kv1.3^{high}$, while insulin- and GAD65-specific T cells were $Kv1.3^{low}$ (p=0.0001). Autoreactive T cells isolated from healthy controls were $Kv1.3^{low}$ regardless of specificity. In one individual with both MS and T1DM, T cells specific for all three autoantigens were $Kv1.3^{high}$. GAD65-specific and insulin-specific T cells from patients with longstanding T1DM were $Kv1.3^{high}$ reflecting the persistence of autoreactive $T_{EM}$ cells, whereas a $Kv1.3^{low}$ pattern was found in GAD65- and insulin-specific T cells from patients with non-autoimmune type-2 DM. As seen in FIG. 12B, Kv1.3 staining (top) and fluorescence intensities of individual cells (bottom). Applicants confirmed the patch-clamp data by immunostaining for Kv1.3. Insulin- and GAD65-specific T cells from T1DM patients and MBP-specific T cells from MS patients stained brightly whereas cells specific for irrelevant autoantigens stained dimly. FIG. 12C shows CCR7 expression. Flow cytometry revealed that $Kv1.3^{high}$ T cells were $CCR7^-$ $T_{EM}$ cells, while $Kv1.3^{low}$ cells were $CCR7^+$ naïve or $T_{CM}$ cells.

Figure 12D:
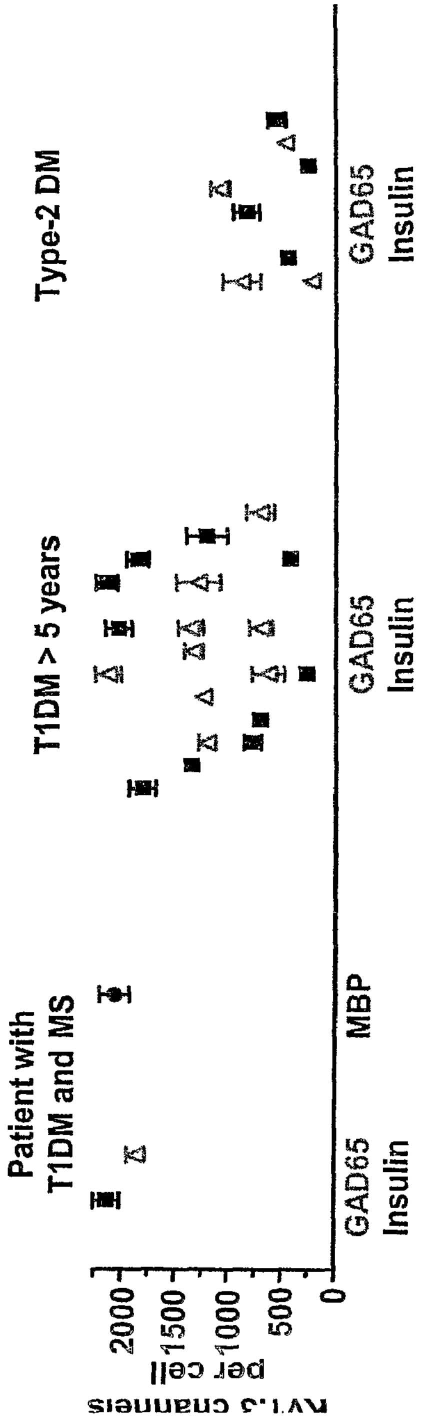
FIG. 12D shows Kv1.3 number/cell in autoreactive T cells from a patient having T1DM and MS (left), patients having T1DM for greater than 5 years duration (middle) and patients having non-autoimmune type-2 DM.
Figure 12E:
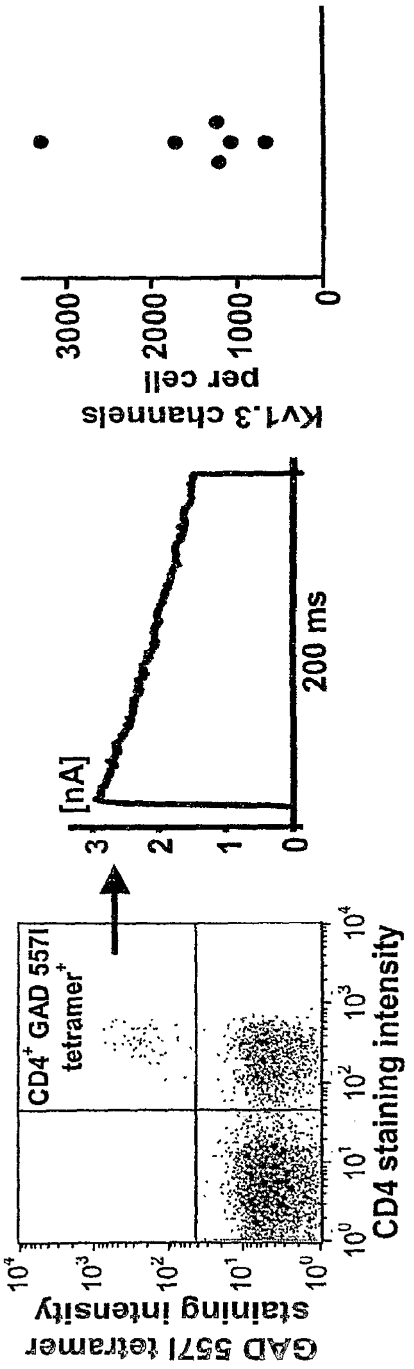
FIG. 12E shows Kv1.3 numbers in CD4$^+$GAD65-tetramer$^+$ T cells from a patient with new-onset T1DM.

FIG. 12D shows Kv1.3 number/cell in autoreactive T cells from a patient with both T1DM and MS, and from patients having T1DM or type-2 DM for greater than 5 years and 2 years, respectively. FIG. 12E shows Kv1.3 numbers in $CD4^+$ $GAD65\text{-tetramer}^+$ T cells from patient with new-onset T1DM. As a further control, we used fluorescent MHC class II tetramers containing the GAD65 557I peptide, to isolate GAD65-specific $CD4^+$ T cells from a DR-0401-positive patient with new onset T1DM. Tetramer-sorted GAD65-activated T cells displayed the same $Kv1.3^{high}$ pattern observed in GAD65-specific T cell lines from T1DM patients. In summary, disease-relevant, autoantigen-activated T cells in both T1DM and MS are $Kv1.3^{high}$ $CCR7^-$ $T_{EM}$-effectors, while disease-irrelevant autoreactive cells in these patients are $Kv1.3^{low}CCR7^+$ naïve/$T_{CM}$ cells.

Kv1.3 Expression in Rheumatoid Arthritis and Osteoarthritis

Figure 13A:
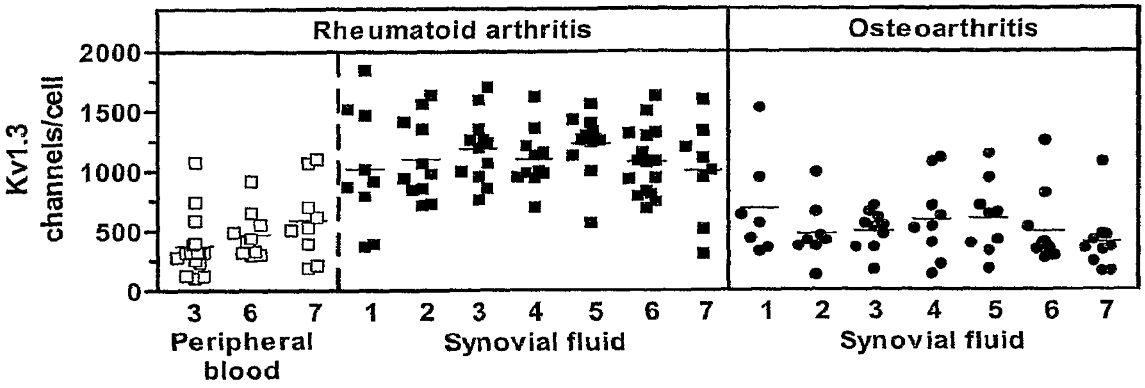
FIG. 13A shows Kv1.3 channel numbers per cell in peripheral T cells blood and synovial fluid T cells of RA patients and synovial fluid T cells of OA patients.
Figure 13B:
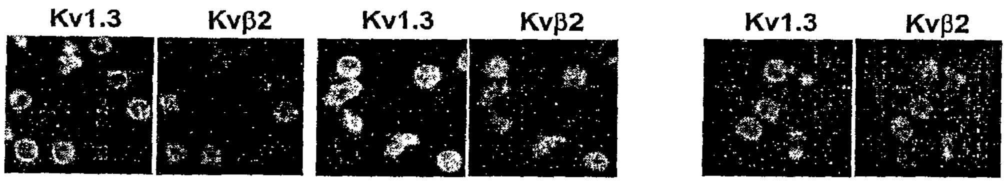
FIG. 13B shows confocal images of Kv1.3 (light grey) and Kv32 (darker grey) staining in the cells shown in FIG. 13A.
Figure 13C:
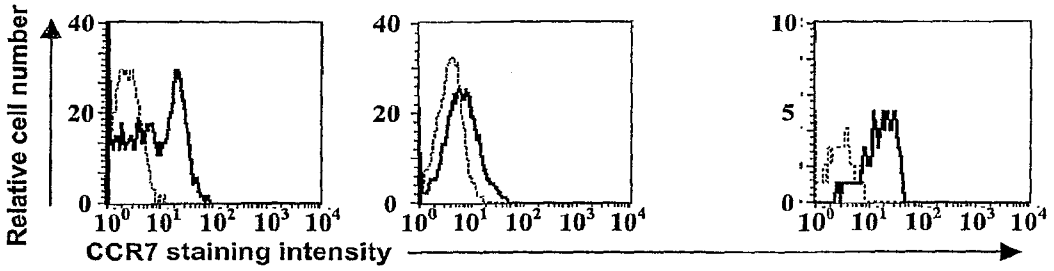
FIG. 13C shows graphs of relative cell number vs. CCR7 staining intensity.
Figure 13D:
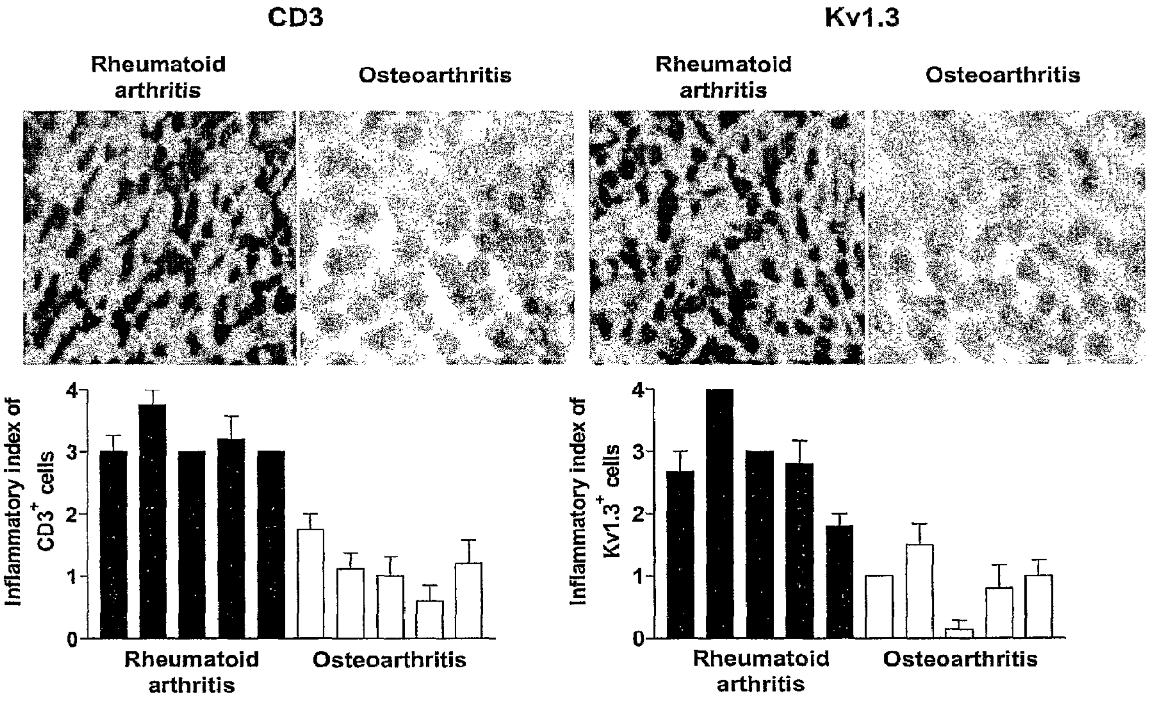
FIG. 13D shows micrographs (top) and bar graphs of inflammatory index (bottom) of synovium from RA and OA patients stained with anti-CD3 or anti-Kv1.3 antibodies and counter-stained with hematoxylin/eosin (40×).

In RA, disease-relevant T cells can be isolated from affected joints. Applicants patch-clamped T cells from the synovial fluid (SF) of 7 RA patients 48 hours after stimulation with anti-CD3 antibody. As seen in FIG. 13A, as controls Applicants analyzed SF-T cells from 7 patients with degenerative, non-autoimmune osteoarthritis (OA) (which had been activated with the same protocol. RA-SF T cells were $Kv1.3^{high}$ whereas OA-SF T cells were $Kv1.3^{low}$ (p<0.0001). Applicants found the $Kv1.3^{low}$ pattern in anti-CD3-activated T cells from the peripheral blood (PB) of RA patients (p<0.0001) because autoreactive $Kv1.3^{high}$ $T_{EM}$ cells are infrequent in the blood. Immunostaining for Kv1.3 and its associated Kvβ2 subunit corroborated the patch-clamp data. FIG. 13B shows confocal images of Kv1.3 (light grey as seen in the figure) and Kvβ2 (darker grey as seen in the figure) staining. RA-SF T cells stained brightly for both Kv1.3 and Kvβ2, while OA-SF and RA-PB T cells displayed weak staining. FIG. 13C illustrates CCR7 expression. Flow cytometry verified that $Kv1.3^{high}$ RA-SF T cells were $CCR7^-$ $T_{EM}$ cells, while $Kv1.3^{low}$ OA-SF and RA-PB T cells were $CCR7^+$ naïve/$T_{CM}$ cells. FIG. 13D (top) shows micrographs of synovium from RA and OA patients stained with anti-CD3 or anti-Kv1.3 antibodies and counter-stained with hematoxylin/eosin (40×). As a further test, we immunostained paraffin-embedded synovial tissues (ST) from 5 RA and 5 OA patients for CD3, Kv1.3 and CCR7. We have previously shown that our staining method does not detect Kv1.3 in naïve/$T_{CM}$ cells because of their low numbers of Kv1.3 channels. In RA-ST, a preponderance of $CD3^+Kv1.3^+CCR7^-$ $T_{EM}$ cells was seen, whereas $CD3^+$ cells were sparse in OA-synovium and these were mainly $Kv1.3^-CCR7^+$ naïve/$T_{CM}$ cells. Degree of infiltration by $CD3^+$, $Kv1.3^+$ and $CCR7^+$ cells assessed by grading system in Figure S2A. $CD3^+$-inflammatory-index: RA=3.2±0.1; OA=1.1±0.2 (p<0.01); $Kv1.3^+$-inflammatory-index: RA=2.8±0.3; OA=0.6±0.3 (p<0.01). Thus, in three different autoimmune disorders, our results are consistent with disease-associated autoreactive T cells being $Kv1.3^{high}CCR7$ $T_{EM}$-effectors.

It is to be appreciated that the invention has been described herein with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or procedure are listed or stated in a particular order, the order of those steps may be changed unless otherwise specified or unless such change in the order of the steps would render the invention unpatentable or unsuitable for its intended use. All reasonable additions, deletions, modifications and alterations are to be considered equivalents of the described examples and embodiments and are to be included within the scope of the following claims.

Appendix A: Toxicity study of ShK(L5)

| *In vitro* tests | 100 nM ShK(L5) |
|---|---|
| **Cytotoxicity (% dead cells)** | |
| Human PBMCs | 7.5 ± 4.3 |
| PAS T cells | 8.1 ± 0.8 |
| Jurkat cells | 5.5 ± 3.3 |
| Burkitt lymphoma | 3.1 ± 0.9 |
| RPMI 8226 myeloma | 6.5 ± 2.1 |
| **Ames Test** | Negative |

| Acute *in vivo* tests | Saline | ShK(L5) 10 μg/kg |
|---|---|---|
| **Electrocardiogram*** | | |
| Heart rate | 302 ± 13 | 311 ± 20 |
| SDNN | 13.3 ± 3.0 | 17.8 ± 4.4 |
| CV% | 6.7 ± 1.4 | 9.2 ± 2.2 |
| $SDANN_{5min}$ | 5.0 ± 2.0 | 6.9 ± 2.3 |
| rMSSD | 6.8 ± 2.2 | 9.8 ± 3.5 |
| HF (n.u.) | 71 ± 21 | 79 ± 37 |
| HF (%) | 50 ± 8 | 53 ± 10 |
| LF (n.u.) | 68 ± 4 | 64 ± 10 |
| LF (%) | 50 ± 8 | 47 ± 10 |
| LF/HF | 1.1 ±0.4 | 1.3 ± 0.7 |

| Sub-chronic *in vivo* tests | Saline | ShK(L5) 10 μg/kg/day for 2 weeks |
|---|---|---|
| **Weight gain (%)** | 7.2 ± 1.8 | 6.2 ± 1.7 |
| **Complete blood count** | | |
| Hematocrit (%) | 40.3 ± 1.4 | 39.0 ± 4.9 |
| Hemoglobin (g/dl) | 15.3 ± 0.5 | 15.0 ± 1.5 |
| MCV (fl) | 48.5 ± 0.2 | 48.3 ± 0.3 |
| MCH (pg) | 18.5 ± 0.8 | 18.5 ± 0.6 |
| MCHC (g/dl) | 38.0 ± 1.8 | 38.4 ± 1.3 |
| Total white cells ($x10^3mm^{-3}$) | 7.1 ± 2.1 | 7.1 ± 2.5 |
| Total red cells ($x10^6mm^{-3}$) | 8.3 ± 0.3 | 8.1 ± 1.0 |
| Total platelets ($x10^3mm^{-3}$) | 656 ± 214 | 606 ± 106 |
| **Blood chemistry** | | |
| Alkaline phosphatase (U/l) | 170 ± 26 | 150 ± 18 |
| Glucose (mg/dl) | 139 ± 21 | 150 ± 18 |
| Blood urea nitrogen (mg/dl) | 17.1 ± 2.6 | 15.0 ± 1.7 |
| Creatinine (mg/dl) | 0.6 ± 0 | 0.6 ± 0.1 |
| Albumin (g/dl) | 5.0 ± 0.3 | 4.5 ± 0.4 |
| **Thymic cell populations (%)** | | |
| $CD4^-CD8^-$ | 3.6 ± 1.1 | 4.3 ± 0.7 |
| $CD4^+CD8^+$ | 77.8 ± 6.1 | 76.8 ± 4.1 |
| $CD4^+CD8^-$ | 8.5 ± 1.7 | 11.2 ± 2.0 |
| $CD4^-CD8^+$ | 10.0 ± 3.3 | 7.6 ± 1.3 |
| $CD3^+$ | 89.5 ± 1.6 | 93.2 ± 3.5 |
| **Splenic populations (%)** | | |
| $CD3^+$ | 72.4 ± 4.4 | 65.4 ± 0.1 |
| $CD3^+CD45RC^+$ | 35.6 ± 2.6 | 39.8 ± 1.1 |
| $CD3^+CD45RC^-$ | 23.6 ± 2.3 | 26.5 ± 1.3 |
| $CD3^+CD4^+$ | 62.7 ± 0.1 | 66.6 ± 1.2 |
| $CD3^+CD8^+$ | 26.9 ± 0.1 | 25.0 ± 0.2 |
| $IgM^+$ | 38.8 ± 1.5 | 33.3 ± 0.3 |

Data expressed as mean ± SD. *Tested with t-tests, $p<0.05$ on all parameters; SDNN: Standard deviation of all normal-to-normal RR intervals; CV%: 100 x SDNN/average RR interval; $SDANN_{5min}$: Standard deviation of the mean of normal RR intervals for each 5 min period; rMSSD: Root mean square of successive difference; HF (n.u.): High frequency (0.75 – 2.5 Hz) power in normalized unit; LF (n.u.): Low frequency (0.2 – 0.75 Hz) power in normalized unit.

APPENDIX B
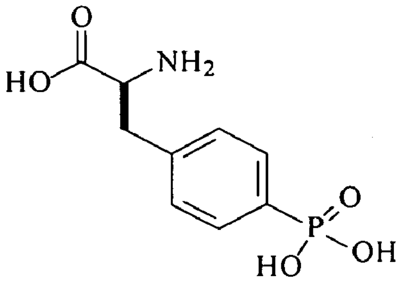
*L-p*-Phosphonophenylalanine (PPA)
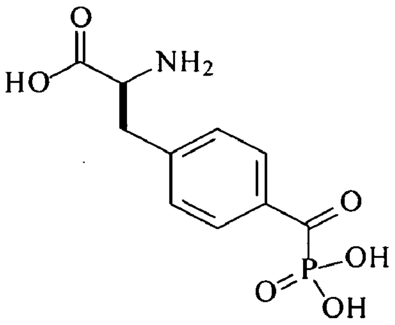
*L-p*-Phosphonomethanonephenylalanine (PM(=O)PA)
(*L-p*-Ketophosphonophenylalanine (KPP)
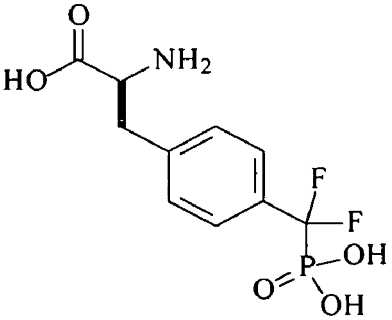
*L-p*-Phosphonodifluromethyl-phenylalanine (PM(f2)PA)
(*L-p*-Difluoromethylphosphonophenylalanine)

0026-895X/05/6704-1369–1381$20.00
MOLECULAR PHARMACOLOGY
Copyright © 2005 The American Society for Pharmacology and Experimental Therapeutics
Mol Pharmacol 67:1369–1381, 2005

Vol. 67, No. 4
8193/1198130
Printed in U.S.A.

Targeting Effector Memory T Cells with a Selective Peptide Inhibitor of Kv1.3 Channels for Therapy of Autoimmune Diseases Christine Beeton, Michael W. Pennington, Heike Wulff, Satendra Singh, Daniel Nugent, George Crossley, Ilya Khaytin, Peter A. Calabresi, Chao-Yin Chen, George A. Gutman, and K. George Chandy

*Department of Physiology and Biophysics, University of California Irvine, Irvine, California (C.B., G.A.G., K.G.C.); Bachem Bioscience Inc., King of Prussia, Pennsylvania (M.W.P., S.S., D.N., G.C., I.K.); Department of Medical Pharmacology and Toxicology, University of California, Davis, California (H.W., C.Y.C.); and Department of Pathology, Johns Hopkins Hospital, Baltimore, Maryland (P.A.C.)*

Received October 13, 2004; accepted January 21, 2005

ABSTRACT

The voltage-gated Kv1.3 $K^+$ channel is a novel target for immunomodulation of autoreactive effector memory T ($T_{EM}$) cells that play a major role in the pathogenesis of autoimmune diseases. We describe the characterization of the novel peptide ShK(L5) that contains L-phosphotyrosine linked via a nine-atom hydrophilic linker to the N terminus of the ShK peptide from the sea anemone *Stichodactyla helianthus*. ShK(L5) is a highly specific Kv1.3 blocker that exhibits 100-fold selectivity for Kv1.3 ($K_d$ = 69 pM) over Kv1.1 and greater than 250-fold selectivity over all other channels tested. ShK(L5) suppresses the proliferation of human and rat $T_{EM}$ cells and inhibits interleukin-2 production at picomolar concentrations. Naive and central memory human T cells are initially 60-fold less sensitive than $T_{EM}$ cells to ShK(L5) and then become resistant to the peptide during activation by up-regulating the calcium-activated $K_{Ca}3.1$ channel. ShK(L5) does not exhibit in vitro cytotoxicity on mammalian cell lines and is negative in the Ames test. It is stable in plasma and when administered once daily by subcutaneous injection (10 μg/kg) attains "steady state" blood levels of ~300 pM. This regimen does not cause cardiac toxicity assessed by continuous EKG monitoring and does not alter clinical chemistry and hematological parameters after 2-week therapy. ShK(L5) prevents and treats experimental autoimmune encephalomyelitis and suppresses delayed type hypersensitivity in rats. ShK(L5) might prove useful for therapy of autoimmune disorders.

Autoimmune diseases afflict millions worldwide and may have a common pathogenic mechanism. Pathogenesis may involve the "awakening" of dormant disease-specific autoreactive T cells—for instance myelin-specific T cells in patients with multiple sclerosis (MS)—by molecular mimicry or other undetermined mechanisms. Once awakened, autoreactive T cells might differentiate from a naive state into continuously activated memory T cells as a consequence of repeated autoantigen stimulation and contribute to inflammatory damage by migrating rapidly into tissues, secreting inflammatory cytokines, and exhibiting immediate effector function (Sallusto et al., 1999). Several lines of evidence support this scheme. First, a majority of myelin-specific T cells from patients with MS are costimulation-independent activated effector memory T ($T_{EM}$) cells (Lovett-Racke et al., 1998; Scholz et al., 1998; Markovic-Plese et al., 2001; Wulff et al., 2003). Second, transfer of myelin-specific $T_{EM}$ cells into naive rat This work was supported by grants from the National Multiple Sclerosis Society (to H.W., K.G.C., P.A.C., M.W.P.), the National Institutes of Health (grant NS048252 to K.G.C.), the Arthritis National Research Foundation (to C.B.), and a Postdoctoral Fellowship from the National Multiple Sclerosis Society (to C.B.).
C.B. and M.P. contributed equally to this work.
Article, publication date, and citation information can be found at http://molpharm.aspetjournals.org.
doi:10.1124/mol.104.008193.

ABBREVIATIONS: MS, multiple sclerosis; $T_{EM}$, effector memory T cell subset; $T_{CM}$, central memory T cell subset; EAE, experimental autoimmune encephalomyelitis; DTH, delayed type hypersensitivity; $K_{Ca}3.1$, intermediate-conductance $Ca^{2+}$-activated $K^+$ channel; $K_V$, voltage-gated $K^+$ channel; ShK, *Stichodactyla helianthus* toxin; Fmoc, 9-fluorenylmethoxycarbonyl; Pmp, *p*-phosphonomethyl-phenylalanine; Aeea, amino-ethyl-oxy-ethyloxy-acetic acid; HEK, human embryonic kidney; HERG, human *ether-a-go-go*-related gene; PBMC, peripheral blood mononuclear cell; IL2, interleukin 2; PBS, phosphate-buffered saline; MBP, myelin basic protein; F6CA, fluorescein-6-carboxyl; L-*p*Tyr, L-phosphotyrosine; CP-339818, 1-benzyl-4-pentylimino-1,4-dihydroquinoline; UK-78282, 4-[diphenylmethoxy)methyl]-1-[3-(4-methoxyphenyl)propyl]-piperidine; WIN-17317, 1-benzyl-7-chloro-4-*n*-propylimino-1,4-dihydroquinoline hydrochloride.

recipients induces experimental autoimmune encephalomyelitis (EAE), a model for MS (Beeton et al., 2001b). Third, T cells from patients with diabetes mellitus type 1 that are specific for the disease-associated autoantigen glutamic acid decarboxylase 65 are continuously activated memory cells (Viglietta et al., 2002). Last, a majority of T cells in the synovium of patients with rheumatoid arthritis and in skin lesions of patients with psoriasis are $T_{EM}$ cells, as are T cells that cause delayed type hypersensitivity (DTH) (Ezawa et al., 1997; Friedrich et al., 2000; Soler et al., 2003). Memory B cells, especially those belonging to the class-switched $CD27^+IgD^-$ subset, also probably contribute to the pathogenesis of many autoimmune diseases (Iglesias et al., 2001; O'Connor et al., 2001; Corcione et al., 2004). Therapies that target $T_{EM}$ and class-switched memory B cells without impairing the activity of other lymphocyte subsets would therefore target the pathogenic cells in patients with autoimmune diseases but without compromising acute immune responses.

An exciting new therapeutic target for immunomodulation of $T_{EM}$ and class-switched memory B cells is the voltage-gated Kv1.3 $K^+$ channel. $T_{EM}$ cells up-regulate Kv1.3 upon activation and their antigen-driven proliferation is exquisitely sensitive to Kv1.3 blockers (Wulff et al., 2003). Naive and $T_{CM}$ cells in contrast are significantly less sensitive to Kv1.3 blockers to begin with and rapidly become resistant to Kv1.3 blockade by up-regulating the calcium-activated $K^+$ channel $K_{Ca}3.1$ (Wulff et al., 2003; Chandy et al., 2004). B cells, like T cells, change their potassium channel dependence from $K_{Ca}3.1$ to Kv1.3 as they differentiate from naive into class-switched $CD27^+IgD^-$ memory B cells (Wulff et al., 2004). Kv1.3 blockers inhibit the proliferation of these cells without affecting naive and $CD27^+IgD^+$ memory B cells. By targeting $T_{EM}$ cells and class-switched memory B cells with Kv1.3 blockers, it might be possible to ameliorate autoimmune diseases without compromising the bulk of the immune response. The functionally restricted tissue distribution of Kv1.3 and the fact that, in vivo, Kv1.3 blockade ameliorates EAE, bone resorption in periodontal disease, and DTH in animal models without causing obvious side effects has enhanced the attractiveness of Kv1.3 as a therapeutic target (Koo et al., 1997; Beeton et al., 2001b; Valverde et al., 2004). Although Kv1.3 blockers would suppress all activated $T_{EM}$ (for example, $T_{EM}$ cells specific for vaccine antigens) and class-switched memory B cells, a Kv1.3-based therapy would be a significant improvement over current therapies that broadly and indiscriminately suppress the entire immune system. An additional advantage of Kv1.3 blockers is that they are reversible. Thus, one could titrate the therapeutic effect of Kv1.3 blockers when needed and stop therapy in the face of infection, unlike chemotherapeutic agents or targeted monoclonal antibody therapies, which take months to subside.

Despite extensive efforts, selective and potent inhibitors of the Kv1.3 channel have not been developed (Chandy et al., 2004). The most potent Kv1.3 inhibitor is the peptide ShK from the Caribbean sea anemone *Stichodactyla helianthus* (Pennington et al., 1995). ShK blocks Kv1.3 ($K_d$, ~10 pM), suppresses proliferation of $T_{EM}$ cells at picomolar concentrations (Wulff et al., 2003), and ameliorates EAE (Beeton et al., 2001b). A potential drawback of ShK is its affinity ($K_d$, 28 pM) for the neuronal Kv1.1 channel (Kalman et al., 1998). Although no side effects were observed with ShK in EAE trials (Beeton et al., 2001b), ingress of high concentrations of ShK into the brain could lead to unwanted neurotoxicity. Other inhibitors including correolide, *trans*-PAC, CP-339818, UK-78282, Psora-4, margatoxin, and luteolin are less selective for Kv1.3 (Chandy et al., 2004). The development of a more selective ShK derivative is therefore necessary.

We have developed ShK(L5), a synthetic analog of ShK that blocked Kv1.3 with picomolar affinity and exhibited greater than 100-fold selectivity for Kv1.3 over Kv1.1 and other channels. Selectivity was achieved by attaching a negatively charged L-phosphotyrosine (L-*p*Tyr) via a hydrophilic linker to ShK-Arg[1]. ShK(L5) suppressed $T_{EM}$ cell proliferation in vitro at picomolar concentrations without compromising the function of naive and $T_{CM}$ cells. In proof-of-concept in vivo studies, ShK(L5) ameliorated EAE caused by the transfer of myelin-specific $T_{EM}$ cells into naive rat recipients and suppressed the DTH response also caused by $T_{EM}$ cells. ShK(L5) may have use as a therapy for multiple sclerosis and other T and B cell-mediated autoimmune diseases.

Materials and Methods

Synthesis of ShK Analogs. For the Fmoc-Pmp analogs, the ethyl protecting groups were removed by treating the Fmoc-Pmp-$(Ethyl)_2$-OH with aqueous 6 N HCl at reflux. After 16 h, a white solid precipitated out that was then isolated by filtration and washed with water until the washings were neutral (Hammerschmidt and Hanbauer, 2000). Partial removal of the ethyl protecting groups from Pmp-phosphonate resulted in either Pmp, Pmp-Et, or $Pmp(Ethyl)_2$. All Fmoc-amino acid derivatives were obtained from Bachem AG (Bubendorf, Switzerland), except for Fmoc-D-$TyrPO_3$(benzyl)-OH, which was obtained from Nova Biochem (San Diego, CA), and Fmoc-Pmp(Ethyl)-OH and Fmoc-D-$Pmp(Ethyl)_2$-OH, which were obtained from Chem Impex (Wood Dale, IL). Solid-phase assembly was initiated with Fmoc-Cys(Trt)-2-chlorotrityl resin to minimize potential racemization of the C-terminal Cys residue (Fujiwara et al., 1994). Automated assembly was carried out on an ABI-431A peptide synthesizer (Applied Biosystems, Foster City, CA). Fmoc-Aeea-OH was coupled to the N terminus after the assembly of ShK. The resin was divided into nine aliquots. Either Fmoc-$Tyr(PO_3Bzl)$-OH, Fmoc-D-$Tyr(PO_3Bzl)$-OH, Fmoc-$Tyr(PO_3Me_2)$-OH, Fmoc-Pmp-OH, Fmoc-D-Pmp-OH, Fmoc-Pmp(Ethyl)-OH, Fmoc-$Pmp(Et)_2$-OH, Fmoc-Tyr(*tert*-butyl)-OH, or Fmoc-*p*-amino-L-phenylalanine(*tert*-butyloxycarbonyl)-OH was coupled, using diisopropylcarbodiimide and 1-hydroxybenzotriazole, to one of the resin aliquots. The deblocked peptide resin was cleaved and deprotected with reagent K (King et al., 1990) containing 5% triisopropylsilane for 2 h at RT. Met(O) was reduced by addition of solid $NH_4I$ to the cleavage cocktail at t − 15 min. (Nicolas et al., 1995). For the peptides containing $Tyr(PO_3Me_2)$-OH, a cleavage cocktail containing 1 M trimethylsilyl bromide in TFA (trifluoroacetic acid) containing thioanisole as a scavenger for 18 h at 4°C was used (Tian et al., 1993). Incomplete removal of the methyl protecting groups is common when using this method, and two of the species [*p*-phosphotyrosine) and $Tyr(PO_3HMe)$] are easily purified by RP-HPLC. The $Tyr(PO_4Me_2)$ containing analog was cleaved via standard Reagent K cleavage keeping both methyl groups intact. In each case, the cleavage mixture was filtered and the crude peptide was precipitated into ice-cold diethyl ether. The precipitate was collected, yielding approximately 75 mg of peptide from 200 mg of resin. The crude product was dissolved in 20 ml of 50% aqueous AcOH and diluted into 0.75 l of $H_2O$. The pH of the solution was adjusted with $NH_4OH$ to 8.2, and it was allowed to fold overnight with the addition of glutathione (2 mM:1 mM) (reduced:oxidized). All analogs were purified using RP-HPLC using a linear gradient of water versus acetonitrile buffered with trifluoroacetic acid as described previously (Pennington et al., 1995, 1996a,b). Pure fractions were pooled and lyophilized, resulting in a trifluoroacetate salt of each peptide. Purity of the peptides was greater than 95%. Each sample was confirmed by reversed-phase high-performance liquid chromatography, amino acid analysis, and matrix-assisted laser desorption ionization/time of flight mass spectrometry and adjusted to account for peptide content before bioassay. ShK and margatoxin were obtained from Bachem Biosciences (King of Prussia, PA). Luteolin was purchased from Sigma-Aldrich (St Louis, MO).

Ion Channels. We used the IUPHAR nomenclature for the ion channels described in this article (Gutman et al., 2003). Cells stably expressing *mKv1.1*, *rKv1.2*, *mKv1.3*, *hKv1.5*, and *mKv3.1* have been described previously (Grissmer et al., 1994). Cell lines stably expressing other mammalian ion channels were gifts from several sources: *mKv1.7* in CHL cells and *hKCa2.3* in COS-7 cells from Aurora Biosciences Corp. (San Diego, CA); *hKv1.4* in LTK cells from Michael Tamkun (University of Colorado, Boulder, CO); *hKv2.1* in HEK293 cells from Jim Trimmer (University of California, Davis, CA); *Kv11.1* (HERG) in HEK293 cells from Craig January (University of Wisconsin, Madison, WI); HEK293 cells expressing *hKCa1.1* or *rKCa2.1* or *hKCa3.1* from Khaled Houamed (University of Chicago, Chicago, IL); *hNav1.4* in HEK-293 cells from Frank Lehmann-Horn (University of Ulm, Germany), and *Cav1.2* in HEK-293 cells from Franz Hofmann (Munich, Germany). RBL-2H3 (expressing *Kir2.1*) and N1E-115 neuroblastoma cells (expressing *Nav1.2*) were obtained from the American Type Culture Collection (Manassas, VA). *hKv1.6* and *rKv3.2* (both in pcDNA3) were obtained from Protinac GmbH (Hamburg, Germany) and transiently-transfected into COS-7 cells with Fugene-6 (Roche, Mannheim, Germany) according to the manufacturers' protocol.

Lymphoid Cells and Cell Lines. Histopaque-1077 gradients (Sigma-Aldrich) were used to isolate splenocytes from Lewis rats and human peripheral blood mononuclear cells (PBMCs) from the blood of healthy volunteers. Human myelin oligodendrocyte glycoprotein- or tetanus toxoid-specific $T_{EM}$ cells were generated as described previously (Wulff et al., 2003). The encephalitogenic CD4$^+$ Lewis rat T cell line PAS (Beraud et al., 1993) was a gift from Evelyne Béraud (University of Marseille, Marseille, France), and RPMI 8226 plasmacytoma cells were a gift from Shastri Gollapudi (University of California, Irvine, CA). Jurkat and Burkitt cells were purchased from the American Type Culture Collection.

Electrophysiological Analysis. Experiments were conducted in the whole-cell configuration of the patch-clamp technique. $K_V$ currents were elicited by 200-ms depolarizing pulses from a holding potential of −80 to 40 mV as described previously (Zhou et al., 1998; Wulff et al., 2000; Bardien-Kruger et al., 2002; Kolski-Andreaco et al., 2004; Vennekamp et al., 2004). Each channel blocker was tested at multiple concentrations. The measured reduction in peak current at 40 mV for each concentration was used to generate a dose-response curve, and the $K_d$ and Hill coefficient were determined with Origin software (OriginLab Corp., Northampton, MA) as described previously (Zhou et al., 1998; Wulff et al., 2000; Bardien-Kruger et al., 2002; Kolski-Andreaco et al., 2004; Vennekamp et al., 2004). The $K_d$ was also determined from the on ($T_{ON}$) and off ($T_{OFF}$) rates for channel block. After stabilization of peak Kv1.3 current amplitude, 70 pM ShK(L5) was perfused onto the cell, and peak current values plotted as a function of time were fitted to a single exponential function to determine $T_{ON}$. After reaching equilibrium block, perfusion was switched back to blocker-free bath solution. Peak currents were plotted as described above to determine $T_{OFF}$. $K_{ON}$, $K_{OFF}$, and $K_d$ were calculated assuming a simple bimolecular reaction between ShK(L5) and Kv1.3: $K_{ON} = 1 - T_{ON} \times K_{OFF}$ / [$T_{ON}$ × ShK(L5) concentration]; $K_{OFF} = 1 / T_{OFF}$; $K_d = K_{OFF} / K_{ON}$ (Peter et al., 2001). For Kv11.1 channels, current block was measured both at 20 and −50 mV (tail current). For $K_{Ca}$ channels, $K_{ir}$2.1, and swelling-activated chloride currents, we measured the change in slope conductance by the ShK analogs and, for $Na^+$ and $Ca^{2+}$ currents, the reduction of minimum current.

Staining for Flow Cytometry and Fluorescence Microscopy. The T cell phenotypes of human PBMCs, rat splenocytes, and PAS T cells were determined by flow cytometry. PBMCs were triple-stained with anti-CD3 antibody conjugated to Cy-chrome (BD Pharmingen, San Diego, CA), anti-CD45RA antibody conjugated to phycoerythrin (BD Pharmingen), and anti-CCR7 antibody conjugated to fluorescein isothiocyanate (R&D Systems, Minneapolis, MN). Rat splenocytes and PAS-stained T cells were double-stained with anti-CD3 antibody conjugated to Cy-chrome and anti-CD45RC antibody conjugated to fluorescein isothiocyanate (BD Pharmingen). The stained cells were analyzed with a FACScan (BD Biosciences, San Jose, CA).

Two approaches were used to evaluate Kv1.3 protein expression in PAS T cells. First, PAS cells were stained with ShK-F6CA (10 nM; Bachem Bioscience Inc.), a fluorophore-tagged ShK analog, and analyzed by flow cytometry as described previously (Beeton et al., 2003). For competition experiments, PAS cells were preincubated with excess unlabeled ShK(L5) (100 nM) before addition of 10 nM ShK-F6CA. Second, PAS cells were permeabilized and stained with anti-Kv1.3 antibody (Koch et al., 1997) (gift from Hans-Gunther Knaus, Innsbruck, Austria) followed by a secondary antibody conjugated to Alexa-488 (Molecular Probes, Eugene, OR). Stained cells were visualized with a Zeiss LSM-510 META confocal microscope (Carl Zeiss GmbH, Jena, Germany), fluorescence intensities were measured for individual cells ($n$ = 10–15), and statistical analysis carried out using the Mann-Whitney $U$ test.

Functional Studies. Proliferation of human and rat T cells was determined with [$^3$H]thymidine incorporation assays as described previously (Beeton et al., 2001a,b; Wulff et al., 2003). For measurements of IL2 production, PAS T cells were activated with MBP in the presence or the absence of ShK or ShK(L5) for 8 h, and the culture supernatants were collected as described previously (Beeton et al., 2001a). IL2 was detected in supernatants using the rat IL2 Quantikine kit (R&D Systems) according to manufacturer's instructions. Effect of exogenous IL2 (20 units/ml; Sigma-Aldrich, St Louis, MO) on proliferation of PAS T cells was determined as described previously (Beeton et al., 2001a).

Circulating Half-Life Determination and Plasma Stability. Known amounts of ShK(L5) were added to Lewis rat serum, and the blocking activity on Kv1.3 channels was tested by patch-clamp to establish a standard dose-response curve. Serum samples from Lewis rats obtained at various times after single subcutaneous or intravenous injections of ShK(L5) were tested for Kv1.3 blocking activity by patch-clamp and the levels of ShK(L5) determined from the standard curve as described previously (Beeton et al., 2001b). In other experiments, Lewis rats received single daily injections of 10 μg/kg ShK(L5) and serum levels of ShK(L5) were determined 24 h after each injection on days 1 to 5. To determine plasma stability of ShK(L5), rat plasma spiked with a known amount of ShK(L5) was incubated at 37°C for varying durations and then tested for Kv1.3 blocking activity; the amount of residual ShK(L5) in these samples was determined from the standard curve.

Cytotoxicity Assays and Ames Test. Human PBMCs, PAS, Jurkat, RPMI 8226, and Burkitt cells were grown for 48 h in the presence or the absence of 100 nM ShK(L5). Cells were then stained with the LIVE/DEAD viability/cytotoxicity kit (Molecular Probes) according to the manufacturer's instructions, and the percentage of live and dead cells was determined using a fluorescence microplate reader (CytoFluor; Applied Biosystems, Foster City, CA). Triton X-100 (0.1%) was used as a positive control for cell death. For the Ames test, the mutagenic activity of ShK(L5) was determined on the *Salmonella typhimurium* tester strain TA97a by Nelson Laboratories (Salt Lake City, UT).

EKG Studies to Evaluate Cardiac Toxicity. Electrocardiographic studies with implanted EKG transmitters (Data Sciences International, Arden Hills, MN) were used for heart rate variability analysis in animals that received ShK(L5) or vehicle. Experimental protocols were reviewed and approved by the Institutional Animal Care and Use Committee of UC Davis. Six Lewis rats (9–11 weeks old; weight = 219 ± 9 g) were anesthetized with a mixture of ketamine (80 mg/kg) and xylazine (7.5 mg/kg) administered by intramuscular injection. EKG transmitters were placed in the peritoneal cavity of each rat and two EKG leads were tunneled subcutaneously to the right shoulder and to the xiphoid space caudal to the ribcage. An analgesic, carprofen (5 mg/kg, subcutaneous), was administered at the end of surgery. Two weeks after surgery, we performed baseline EKG recording on the rats for 2 h (day 1). We then injected the vehicle (PBS + 2% rat serum) subcutaneously and continued recording for another 8 h. The animals were then returned to their rooms. On day 2, we performed baseline EKG recording for 2 h after which ShK(L5) (10 μg/kg dissolved in vehicle) was injected subcutaneously and EKG recording continued for another 8 h. Data recorded from 1.5 to 3.5 h after the injections were used for standard heart rate variability parameters-analysis in both time and frequency domains using Nevokard software (Bio-Impedance Technology, Inc., Chapel Hill, NC).

Subchronic Toxicity Studies. Lewis rats (9–11 weeks old; weight, 199 ± 7 g) received subcutaneous injections of ShK(L5) 10 μg/kg/day ($n$ = 6) or saline ($n$ = 6) for 2 weeks. Rats were weighed daily. The Comparative Biology Laboratory at University of California, Davis performed chemical (COBAS MIRA Plus; Roche Diagnostic Systems, Branchburg, NJ) and hematological (HEMAVET® 850 Multispecies Hematology Analyzer; CDC Technologies, Oxford, CT) analysis on blood samples drawn at the end of 2 weeks. Single-cell suspensions prepared from thymuses and spleens removed from six animals given ShK(L5) and six given saline were stained with antibodies specific for various T and B cell markers (BD Pharmingen) and analyzed by flow cytometry.

Prevention and Treatment of Acute Adoptive EAE and Prevention of DTH in Lewis Rats. Female inbred Lewis rats 9 to 11 weeks old were purchased from Harlan-Sprague-Dawley (Indianapolis, IN) and housed under barrier conditions with irradiated rodent chow and acidified water ad libitum. All experiments were in accordance with National Institutes of Health guidelines and approved by the Institutional Animal Care and Use Committee at the University of California, Irvine. ShK(L5) was dissolved in PBS + 2% Lewis rat serum (saline) for subcutaneous injection. Acute adoptive EAE was induced as described previously (Beeton et al., 2001a,b) with 6 to 8 × $10^6$ myelin basic protein (MBP)-activated PAS cells. MBP was extracted from frozen guinea pig spinal cords (Harlan Bioproducts, Indianapolis, IN) as described previously (Deibler et al., 1972). Rats were weighed daily and observed twice daily for clinical signs of EAE. For prevention trials, rats received 10 μg/kg/day ShK(L5) from days 0 to 5, whereas control rats received saline. For treatment trials, administration of ShK(L5) (10 μg/kg/day) or saline was begun after the onset of disease (rats had a limp tail, were hunched, and had lost ≥6% of their weight over 24 h) and continued for 3 days.

For DTH trials, Lewis rats were immunized with an emulsion of ovalbumin in complete Freund's adjuvant (Difco, Detroit, MI). Seven days later, they received an injection of ovalbumin dissolved in saline in the pinna of one ear and saline in the other ear. Rats then received subcutaneous injections of ShK(L5) (10 μg/kg/day) or vehicle (PBS + 2% Lewis rat serum). Ear swelling was measured 24 and 48 h later using a spring-loaded micrometer (Mitutoyo, Spokane, WA).

Results

ShK(L5), a Novel ShK Analog that Exhibits 100-fold Selectivity for Kv1.3 Over Kv1.1. ShK blocks the neuronal Kv1.1 channel and the Kv1.3 channel with roughly equivalent potency. Neurotoxicity is therefore a concern under circumstances that compromise the blood-brain barrier and allow the entry of sufficient amounts of ShK to block Kv1.1 channels. Our strategy to design a Kv1.3-specific inhibitor was guided by our finding that ShK-F6CA containing fluorescein-6-carboxylate (F6CA), attached through a 20-Å Aeea linker to the N terminus of ShK exhibited 80-fold selectivity for Kv1.3 over Kv1.1 (Beeton et al., 2003). Because F6CA can exist as a restricted carboxylate or also as a cyclized lactone, it was not clear whether the Kv1.3 specificity of ShK-F6CA was a result of the negative charge of F6CA, the hydrophobicity created by this large bulky fluorescein nucleus, potential planar π-π electronic stacking, or a combination of all of these potential contributions. To distinguish between these possibilities and with the intention of developing a nonfluorescent Kv1.3-selective inhibitor, we generated a series of 12 novel N-terminally-substituted ShK analogs to probe some of these interactions. By attaching tyrosine, phenylalanine, or their derivatives (varying in charge, size, and hydrophobicity) through an Aeea linker to the N terminus of ShK, we could probe the effects of charge and hydrophobicity to gain insight into our selectivity enhancement seen with F6CA substitution.

In the example shown in Fig. 1A, L-phosphotyrosine (L-$p$Tyr) a negatively charged (net charge −2) post-translationally modified aromatic amino acid, was attached via the AEEA linker to ShK-$Arg^1$ to generate a novel analog called ShK(L5). ShK and ShK(L5) were tested on Kv1.3 and Kv1.1 channels stably expressed in L929 cells. Figure 1B shows the effects of ShK and ShK(L5) on Kv1.3 and Kv1.1 currents elicited by 200-ms depolarizing pulses from a holding potential of −80 to 40 mV. Both peptides reversibly blocked Kv1.3 and Kv1.1 in a dose-dependent manner with Hill coefficients of 1 (Fig. 1, B–D). $K_d$ values were determined from the dose-response curves shown in Fig. 1C using Origin software. ShK blocked Kv1.3 ($K_d$ = 10 ± 1 pM) and Kv1.1 ($K_d$ = 28 ± 6 pM) with roughly equivalent potency, as expected (Fig. 1C). In contrast, ShK(L5) was 100-fold selective for Kv1.3 ($K_d$ = 69 ± 5 pM) over Kv1.1 ($K_d$ = 7.4 ± 0.8 nM) (Fig. 1, B and C). The time course of Kv1.3 current block by ShK(L5) and its washout is shown in Fig. 1D. The time constant ($T_{ON}$) of ShK(L5) wash-in was 131 ± 21 s ($n$ = 7), whereas the time constant ($T_{OFF}$) for peptide wash-out was 150 ± 28 s ($n$ = 4). The $K_d$ (57 ± 7 pM) calculated from the $K_{ON}$ (15 × $10^6$± 0.5 × $10^6$ $M^{-1}s^{-1}$) and $K_{OFF}$ (0.0059 ± 0.0013 $s^{-1}$) values is consistent with the $K_d$ (69 ± 5 pM) determined with the use of Origin software.

Other ShK analogs were tested on Kv1.3 and Kv1.1 channels (Fig. 1E). ShK(D5) containing D-phosphotyrosine was 35-fold selective for Kv1.3 over Kv1.1 but was an order of magnitude less potent than ShK(L5). ShK(L6) containing L-$p$Tyr-monomethyl showed modest (11-fold) Kv1.3 specificity, whereas ShK analogs containing L-$p$Tyr-dimethyl or L-Tyr were not selective for Kv1.3 over Kv1.1 (Fig. 1E). Analogs that contained phenylalanine or its derivatives (varying in bulk, π electron density, and charge) were modestly specific or not specific for Kv1.3 over Kv1.1 (Fig. 1E). The 100-fold specificity of ShK(L5) for Kv1.3 over Kv1.1 is greater than that of ShK-F6CA (80-fold), ShK(D5) (35-fold), ShK-$Dap^{22}$ (33-fold), or any other ShK analog tested (Fig. 1C).

ShK(L5) Is a Highly Specific Kv1.3 Inhibitor. We assessed the specificity of ShK(L5) on a panel of 20 ion channels (Table 1). ShK(L5) blocked the Kv1.3 channel in T cells with a $K_d$ (76 pM) equivalent to its $K_d$ on the cloned channel (69 pM). It was 100-fold selective for Kv1.3 over Kv1.1, 260-fold selective over Kv1.6, 280-fold selective over Kv3.2, 680-fold selective over Kv1.2, and >1000-fold selective over all other channels tested. It is noteworthy that it was 1600-fold Kv1.3-selective over KCa3.1, the calcium-activated $K^+$ channel that regulates activation of human naive and $T_{CM}$ cells (Wulff et al., 2003). Native ShK was less selective than ShK(L5). ShK was 2.8-fold selective for Kv1.3 ($K_d$ = 10 ± 1 pM) over Kv1.1 ($K_d$ 28 ± 6 pM), 20-fold selective over Kv1.6 (200 ± 20 pM), 500-fold selective over Kv3.2 ($K_d$ = 5000 ± 1000 pM), and >1000-fold selective-over Kv1.2 (10 ± 1 nM) and KCa3.1 ($K_d$ = 28 ± 3 nM). Margatoxin, a peptide from scorpion venom that has been touted as a specific Kv1.3 inhibitor (Lin et al., 1993; Koo et al., 1997; Middleton et al., 2003) was also not specific. It was 5-fold selective for Kv1.3 (110 ± 12 pM) over Kv1.2 ($K_d$ = 520 ± 1 pM), 9-fold selective over Kv1.1 (10 ± 1 nM), and >1000-fold selective over Kv1.6 and Kv3.2 ($K_d$ > 100 nM). Luteolin, a nutriceutical sold for autoimmune diseases (http://www.lutimax.com) on the basis of its being a Kv1.3 inhibitor (Lahey and Rajadhyaksha, 2004), blocked Kv1.3 weakly ($K_d$ = 65 ± 5 μM) and exhibited no selectivity over Kv1.1 ($K_d$ = 77 ± 5 μM), Kv1.2 ($K_d$ = 63 ± 4 μM), or Kv1.5 ($K_d$ = 41 ± 3 μM). The exquisite specificity of ShK(L5) for Kv1.3, together with its picomolar affinity for the channel, makes it a potentially attractive immunosuppressant.

ShK(L5) Preferentially and Persistently Suppresses Human $T_{EM}$ Cell Proliferation. To assess the in vitro immunosuppressive activity of ShK(L5), we compared its ability to suppress anti-CD3 antibody-stimulated proliferation of human $T_{EM}$ cell lines versus human PBMCs that contain a mixture of naive and $T_{CM}$ cells. Flow cytometry confirmed the cell surface phenotypes of the two populations studied. The $T_{EM}$ lines were >90% $CCR7^-CD45RA^-$ (Fig. 2A), whereas PBMCs contained 65% $CCR7^+CD45RA^+$ (naive) and 18% $CCR7^+CD45RA^-$ ($T_{CM}$) cells (Fig. 2B). Figure 2C shows that ShK(L5) and ShK were 60-fold more effective in suppressing the proliferation of $T_{EM}$ cells ($IC_{50}$ = ~80 pM) compared with PBMCs ($IC_{50}$ = 5 nM, $p < 0.05$). The lower sensitivity of PBMCs might be explained by a rapid up-regulation of KCa3.1 channels in naive and $T_{CM}$ cells upon stimulation as has been reported previously (Ghanshani et al., 2000; Wulff et al., 2003). In keeping with this interpretation, PBMCs activated for 48 h to up-regulate KCa3.1 expression, then rested for 12 h and re-activated with anti-CD3 antibody, were completely resistant to ShK(L5) block (Fig. 2D, top arrow). PBMCs that had been suppressed by ShK(L5) during the first round of stimulation exhibited identical resistance to ShK(L5) when the cells were washed, rested, and re-challenged with anti-CD3 antibody. These results corroborate an earlier report showing that naive and $T_{CM}$ cells escape Kv1.3 inhibitors by up-regulating KCa3.1 channels (Wulff et al., 2003). Thus, ShK(L5) preferentially and persistently suppresses the proliferation of $T_{EM}$ cells.

ShK(L5) Inhibits Proliferation of and IL2 Production by Rat $T_{EM}$ Cells; Exogenous IL2 Partially Overrides Suppression. As a preamble to evaluating therapeutic effectiveness of ShK(L5), we examined its ability to suppress proliferation of a memory T cell line, PAS, that causes an MS-like disease in rats (Beraud et al., 1993). As a control, we used rat splenic T cells. To confirm the differentiation status of the two cell populations, we assessed the

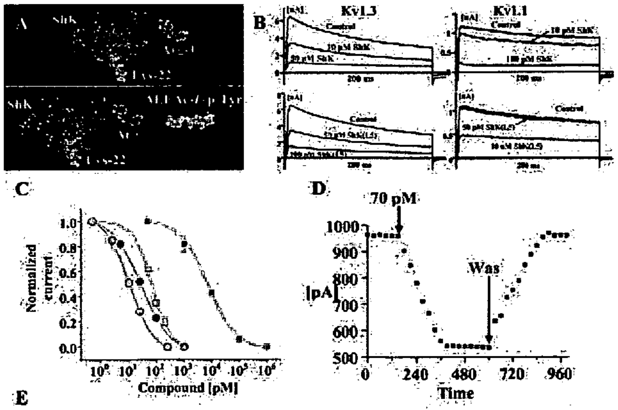

E

| Compound | Residue attached at position -2 | Net charge at position -2 | $K_d$ on Kv1.3 [pM] | $K_d$ on Kv1.1 [pM] | Ratio of $K_d$s |
|---|---|---|---|---|---|
| ShK | None | None | 10 ± 1 | 28 ± 6 | 2.8 |
| ShK(L5) | L-p-Tyr | -2 | 69 ± 5 | 7,400 ± 900 | 104.2 |
| ShK(D5) | D-p-Tyr | -2 | 1,100 ± 150 | 39,000 ± 650 | 35.4 |
| ShK(L6) | L-p-Tyr monomethyl | -1 | 10 ± 1 | 112 ± 9 | 11.2 |
| ShK(L7) | L-p-Tyr dimethyl | 0 | 24 ± 2 | 175 ± 30 | 7.3 |
| ShK(L4) | L-Tyr | 0 | 47 ± 6 | 159 ± 5 | 3.4 |
| ShK(L1) | L-Pmp | -2 | 293 ± 45 | 1,000 ± 100 | 3.4 |
| ShK(D1) | D-Pmp | -2 | 96 ± 12 | 1,400 ± 80 | 14.6 |
| ShK(D2) | D-Pmp monoethyl | -1 | 311 ± 16 | 1,100 ± 100 | 3.5 |
| ShK(L3) | L-Pmp diethyl | 0 | 71 ± 6 | 1,100 ± 200 | 15.5 |
| ShK(D3) | D-Pmp diethyl | 0 | 70 ± 9 | 166 ± 13 | 2.4 |
| ShK(L9) | L-p-COOH-Phe | -1 | 94 ± 7 | 319 ± 36 | 3.4 |
| ShK-L8 | L-p-amino-Phe | +1 | 65 ± 4 | 142 ± 13 | 2.2 |
| ShK-F6CA | F6CA | -1 | 48 ± 4 | 4,000 ± 300 | 83 |
| ShK-Dap[22] | None | None | 52 ± 3 | 1,800 ± 577 | 35 |

Fig. 1. Generation of a selective Kv1.3 blocker. A, molecular model of ShK based on the published NMR structure. The $Lys^{22}$, critical for channel blockade, is highlighted in orange. L-pTyr was attached to the α-amino group of $Arg^1$ of ShK (highlighted in cyan) through an Aeea linker (right). The structures of the linker and L-pTyr were modeled with AM1 in Hyperchem. B, effect of ShK (top) and ShK(L5) (bottom) on Kv1.3 and Kv1.1 currents in stably transfected cells. C, dose-dependent inhibition of Kv1.3 (open symbols) and Kv1.1 (closed symbols) by ShK (blue) and ShK(L5) (red). $K_d$ values on Kv1.3 = 10 ± 1 pM (ShK) and 69 ± 5 pM (ShK(L5)); $K_d$ values on Kv1.1 = 28 ± 6 pM (ShK) and 7.4 ± 0.8 nM (ShK(L5)). D, time course of wash-in and wash-out of ShK(L5) on Kv1.3. Cells were held at a holding potential of −80 mV and depolarized for 200 ms to 40 mV every 30 s. E, $K_d$ values shown for inhibition of Kv1.3 and Kv1.1 by ShK analogs. $K_d$ values for ShK-F6CA and ShK-$Dap^{22}$ are from published sources (Kalman et al., 1998; Beeton et al., 2003; Chandy et al., 2004).

expression of CD45RC, a marker of naive T cells (Bunce and Bell, 1997). Rat splenic T cells were 76% CD45RC$^+$ (i.e., mainly naive cells), whereas PAS cells were CD45RC$^-$, suggesting that they are memory cells (Fig. 3A). To determine whether PAS cells are in the $T_{EM}$ or $T_{CM}$ state, we examined Kv1.3 expression before and 48 h after activation. $T_{EM}$ but not $T_{CM}$ cells are expected to significantly up-regulate Kv1.3 levels upon stimulation (Beeton et al., 2001b, 2003). Patch-clamp experiments revealed a striking increase in Kv1.3 current amplitude after MBP-stimulation of PAS cells consistent with their being $T_{EM}$ cells (Fig. 3B). As an independent measure of the number of Kv1.3 channels on PAS cells, we used ShK-F6CA, a fluorescently labeled ShK analog that binds specifically to Kv1.3 (Beeton et al., 2003). The intensity of ShK-F6CA staining determined by flow cytometry reflects the number of Kv1.3 tetramers expressed on the cell surface (Beeton et al., 2003). ShK-F6CA (10 nM) staining intensity increased with MBP-activation of PAS cells, and an excess of unlabeled ShK(L5) (100 nM) competitively inhibited ShK-F6CA staining (Fig. 3C). As a final test, we performed confocal microscopy on quiescent and MBP-stimulated PAS cells that had been fixed and stained with a Kv1.3-specific antibody. In keeping with data in Fig. 3, B and C, resting PAS T cells had a Kv1.3 staining intensity of 4.4 ± 0.6, and this value increased to 10.6 ± 2.3 ($p < 0.005$) after antigen-induced activation (Fig. 3D), showing augmentation in Kv1.3 protein expression after activation. Thus, MBP-activated PAS cells are CD45RC$^-$ Kv1.3$^{high}$ $T_{EM}$ cells, whereas rat splenic T cells used in our experiments are predominantly in the naive state.

MBP-triggered proliferation of PAS cells was suppressed ~1000-fold more effectively by ShK(L5) and ShK ($IC_{50}$ = ~80 pM) than mitogen-induced proliferation of rat splenic T cells (Fig. 3E, $IC_{50}$ ≈100 nM; $p < 0.05$). These results corroborate the findings with human T cells (Fig. 2). ShK(L5) inhibited MBP-induced IL2 production by PAS cells (Fig. 3F), and exogenous IL2 partially overrode ShK(L5) suppression of PAS cell proliferation (Fig. 3G). Earlier studies reported similar findings with less specific Kv1.3 inhibitors on human, rat and mini-pig T cells (Chandy et al., 1984; Koo et al., 1997; Beeton et al., 2001a). In summary, ShK(L5) is a powerful and selective inhibitor of human and rat $T_{EM}$ cells and may therefore have therapeutic use in autoimmune diseases by preferentially targeting $T_{EM}$ cells that contribute to the pathogenesis of these disorders (Chandy et al., 2004).

ShK(L5) Plasma Values after Subcutaneous Administration. Before embarking on in vivo studies in a rat EAE model, we used a patch-clamp bioassay to ascertain whether circulating levels of ShK(L5) after subcutaneous injection were sufficient to inhibit $T_{EM}$ cells. Serum samples from ShK(L5)-treated and control rats were tested for blocking activity on Kv1.3 channels. Control serum did not exhibit detectable blocking activity, indicating an absence of endogenous channel blockers. To standardize the assay, known amounts of ShK(L5) were added to rat serum, and these samples were tested on Kv1.3 channels. The spiked serum samples blocked Kv1.3 currents in a dose-dependent fashion ($K_d$, 77 ± 9 pM) that was indistinguishable from the effect of ShK(L5) effect in the absence of serum (Fig. 4A). Levels of TABLE 1
Selectivity of ShK(L5)

| Channels | $K_d$ of ShK(L5) |
|---|---|
| | *pM* |
| Kv1.1 | 7000 ± 1000 |
| Kv1.2 | 48,000 ± 7000 |
| Kv1.3 (cloned) | 69 ± 5 |
| Kv1.3 (native) | 76 ± 8 |
| Kv1.4 | 137,000 ± 3000 |
| Kv1.5 | 100,000 (N.E.) |
| Kv1.6 | 18,000 ± 3000 |
| Kv1.7 | 100,000 (N.E.) |
| Kv2.1 | 100,000 (N.E.) |
| Kv3.1 | 100,000 (N.E.) |
| Kv3.2 | 20,000 ± 2000 |
| Kir2.1 | 100,000 (N.E.) |
| Kv11.1 (HERG) | 100,000 (N.E.) |
| $K_{Ca}1.1$ | 100,000 (N.E.) |
| $K_{Ca}2.1$ | 100,000 (N.E.) |
| $K_{Ca}2.3$ | 100,000 (N.E.) |
| $K_{Ca}3.1$ | 115,000 ± 5000 |
| Nav1.2 | 100,000 (N.E.) |
| Nav1.4 | 100,000 (N.E.) |
| Swelling-activated T cell Cl$^-$ channel | 100,000 (N.E.) |
| Cav1.2 | 100,000 (N.E.) |

N.E., no effect.

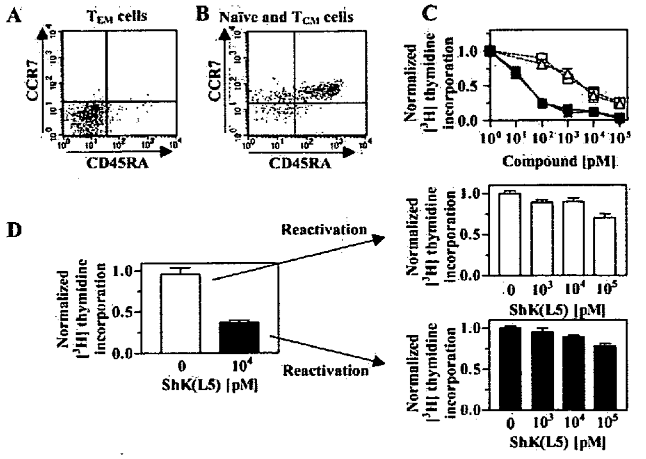

Fig. 2. ShK(L5) preferentially suppresses the proliferation of human $T_{EM}$ cells. Human PBMCs (A) and a human $T_{EM}$ line (B) were stained with antibodies against CD3, CD45RA, and CCR7. Staining intensities of CD45RA and CCR7 were determined by flow cytometry in the CD3$^+$-gated population. C, dose-dependent inhibition by ShK (blue) and ShK(L5) (red) of [$^3$H] thymidine incorporation by PBMCs (open symbols, a mixture of naive/$T_{CM}$ cells) and $T_{EM}$ cells (closed symbols) stimulated for 48 h with anti-CD3 antibody. D, preactivated human PBMCs (naive/$T_{CM}$ cells) that up-regulate KCa3.1 expression (Ghanshani et al., 2000) become resistant to ShK(L5) inhibition when reactivated with anti-CD3 antibody. These cells have previously been shown to become sensitive to the $K_{Ca}3.1$-specific inhibitor TRAM-34 (Ghanshani et al., 2000).

ShK(L5) in treated animals were determined by comparison with the standard curve. ShK(L5) was detectable in serum 5 min after a single subcutaneous injection of 200 μg/kg (Fig. 4B). Peak levels (12 nM) were reached in 30 min and the level then fell to a baseline of approximately 300 pM over 420 min (Fig. 4B). The disappearance of ShK(L5) from the blood could be fit by a single exponential (Fig. 4C). The circulating half-life was estimated to be ~50 min.

Because the peak serum level after 200 μg/kg (12 nM) significantly exceeds the requirement for selective blockade of Kv1.3 channels and $T_{EM}$ cell function, we tested lower doses. After a single injection of 10 μg/kg, the peak serum concentration of ShK(L5) reached ≈500 pM within 30 min (data not shown), a concentration sufficient to block >90% Kv1.3 but not affect Kv1.1. Repeated daily administration of this dose (10 μg/kg/day) resulted in steady-state levels of ~300 pM (measured 24 h after injection; Fig. 4D), which is sufficient to cause 60 to 70% suppression of $T_{EM}$ cells with little effect on naive/$T_{CM}$ cells. The "steady-state" level is unexpected given the estimated circulating half-life of ~50 min and indicates that ShK(L5) "accumulates" on repeated administration. To determine whether the "depot" was in the skin or elsewhere in the body, we measured blood levels of ShK(L5) 10 h after rats received single intravenous or subcutaneous injections of 10 μg/kg ShK(L5). The peptide disappeared with the same time course after administration by either route (Fig. 4E), indicating that the skin is not responsible for the steady-state level of 300 pM ShK(L5) reached after a single 10 μg/kg daily injection (Fig. 4D), and the depot(s) resides elsewhere.

Our success in achieving a steady-state level of 300 pM ShK(L5) after daily single injections of 10 μg/kg/day suggests that the peptide may be stable in vivo. To examine its stability, we incubated ShK(L5) in rat plasma or in PBS containing 2% rat plasma at 37°C for varying durations and then measured Kv1.3 blocking activity. In both sets of spiked samples (plasma and PBS) we observed a 50% reduction in Kv1.3-blocking activity in approximately 5 h, presumably due to peptide binding to the plastic surface of the tube, and the level then remained steady for the next 2-days (Fig. 4F). As an added test of stability, we compared the Kv1.3- versus Kv1.1-blocking activities of sera from ShK(L5)-treated rats. If ShK(L5) is modified in vivo, either by dephosphorylation of *p*Tyr or cleavage of the Aeea-*p*Tyr side chain, it would yield ShK(L4) and ShK, respectively, neither of which is selective for Kv1.3 over Kv1.1 (Fig. 1E). Serum samples from ShK(L5)-treated animals exhibited the same selectivity for Kv1.3 over Kv1.1 as ShK(L5), indicating that the peptide does not undergo the modifications stated above. Taken together, these results indicate that ShK(L5) is remarkably stable in plasma and attains pharmacologically relevant serum concentrations after single daily subcutaneous injections of 10 μg/kg.

Toxicity Studies. We conducted several in vitro and in vivo tests to determine whether ShK(L5) exhibits any toxicity (Table 2). Human and rat lymphoid cells incubated for 48 h with a concentration (100 nM) of ShK(L5) >1200 times greater than the Kv1.3 half-blocking dose or the $IC_{50}$ for $T_{EM}$ suppression (70–80 pM) exhibited minimal cytotoxicity. The same high concentration of ShK(L5) was negative in the Ames test on tester strain TA97A, suggesting that it is not a mutagen. Both in vitro tests failed to detect any significant toxicity.

Drug-induced blockade of Kv11.1 (HERG) channels has contributed to major cardiac toxicity and the withdrawal of several medications from the market. ShK(L5) has no effect on Kv11.1 channels at 100 nM (>1430-fold the $K_d$ for Kv1.3), and our chosen therapeutic regimen (10 μg/kg/day, 300 pM steady-state circulating level) should therefore not cause cardiotoxicity. As a further test, we performed heart rate variability analysis in conscious rats administered vehicle (PBS + 2% rat serum) on day 1, followed by 10 μg/kg/day ShK(L5) on day 2. ShK(L5) had no effect on heart rate or the standard

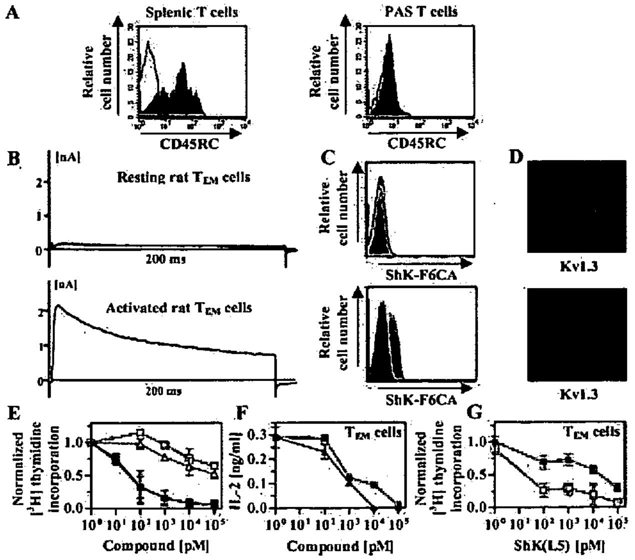

Fig. 3. ShK(L5) preferentially suppresses the proliferation of rat $T_{EM}$ cells. A, CD45RC staining of rat splenic T cells (left) and PAS T cells (right) detected by flow cytometry. B, Kv1.3 currents exhibited by quiescent (top) and myelin antigen-activated (bottom) PAS T cells. C, flow cytometry profiles of ShK-F6CA-staining in quiescent (top) and myelin antigen-activated (bottom) PAS T cells. Unstained cells (black lines) and cells stained with ShK-F6CA (green filled). Competition of ShK-F6CA staining by unlabeled ShK(L5) is red-filled. D, confocal images of Kv1.3 immunostaining in quiescent (top) and myelin antigen-activated (bottom) PAS T cells. Statistical analysis was carried out using the Mann-Whitney *U* test. E, dose-dependent inhibition by ShK (blue) and ShK(L5) (red) of [$^3$H]thymidine incorporation by rat naive/$T_{CM}$ (open symbols) and $T_{EM}$ (closed symbols) cells activated with Con A (1 μg/ml). F, dose-dependent inhibition by ShK (blue) and ShK(L5) (red) of IL2 secretion by PAS T cells 7 h after stimulation with MBP. G, ShK(L5)-induced inhibition of myelin-antigen triggered [$^3$H]thymidine incorporation by PAS T cells (open symbols) is reversed by the addition of 20 units/ml IL2 (closed symbols).

HRV (heart rate variability) parameters in either the time or the frequency domain (Task Force of the European Society of Cardiology and the North American Society of Pacing Electrophysiology, 1996).

Encouraged by the acute toxicity experiments, we performed a subchronic toxicity study in which rats were administered daily subcutaneous injections of 10 μg/kg ShK(L5) or vehicle for 2 weeks ($n$ = 6 in each group). ShK(L5)-treated animals gained weight to the same degree as rats receiving vehicle (Table 2). Hematological and blood chemistry analysis showed no difference between ShK(L5)- and vehicle-treated rats, and flow cytometric analysis revealed no differences in the proportions of thymocyte or lymphocyte subsets (Table 2). Together, these studies suggest that ShK(L5) is safe.

To determine the therapeutic safety index, we administered a 60-fold higher dose (600 μg/kg/day) of ShK(L5) to healthy rats for 5 days and observed no clinical signs of toxicity, and no toxicity was seen when healthy rats received a single injection of 1000 μg/kg ShK(L5). The situation is less sanguine when the blood-brain barrier is compromised, as happens in EAE and MS. Rats with EAE that received ShK(L5) 10 μg/kg/day for 10 days showed no signs of toxicity. In contrast, 40% of rats (5 of 12) administered 600 μg/kg/day for 5 days died on the fifth day when they developed clinical signs of EAE (extrapolated $LD_{50}$ = 750 μg/kg/day). Because the peak concentration of ShK(L5) in the serum (12 nM) after administration of a single injection of 200 μg/kg is sufficient to block >50% of Kv1.1 channels, toxicity observed in EAE rats administered 600 μg/kg/day ShK(L5) is probably caused by the ingress into the brain of sufficient amounts of ShK(L5) to block Kv1.1. Thus, the effective therapeutic safety index of ShK(L5) is well in excess of 100 in situations in which the blood-brain barrier is not compromised (as seen in autoimmune diseases that do NOT affect the central nervous system), whereas the therapeutic safety index is 75 when the blood-brain barrier is breached.

ShK(L5) Prevents and Treats Acute Adoptive EAE and Prevents DTH in Lewis Rats. ShK(L5) was evaluated for immunosuppressive activity in vivo in two animal models. We tested its ability to prevent and treat acute EAE induced by the transfer of MBP-activated PAS $T_{EM}$ cells into Lewis rats (Beeton et al., 2001a,b; Beraud et al., 1993), as well as to suppress the DTH reaction mediated by $T_{EM}$ cells (Soler et al., 2003). PAS cells were activated with MBP for 48 h in vitro and then adoptively transferred (6–8 × $10^6$ viable cells) into Lewis rats. For the prevention trial, rats then received subcutaneous injections of saline (control rats) or ShK(L5) (10 μg/kg/day) for 5 days. In the first prevention trial, control rats developed mild EAE (mean maximum clinical score 2.0 ± 1.2) with an average onset of 5.6 ± 0.6 days (not shown). ShK(L5) reduced disease severity (mean maximum clinical score, 0.7 ± 0.6, $p < 0.05$). In the second prevention trial, control rats developed more severe EAE (mean maximum clinical score 3.2 ± 0.4) with a mean onset of 4.8 ± 0.4 days (Fig. 5A). ShK(L5) significantly reduced disease severity (mean maximum clinical score 0.6 ± 0.4, $p < 0.007$) but did not significantly delay disease onset (5.5 ± 0.7 days; $p$ = 0.07). No signs of toxicity were noted in these studies.

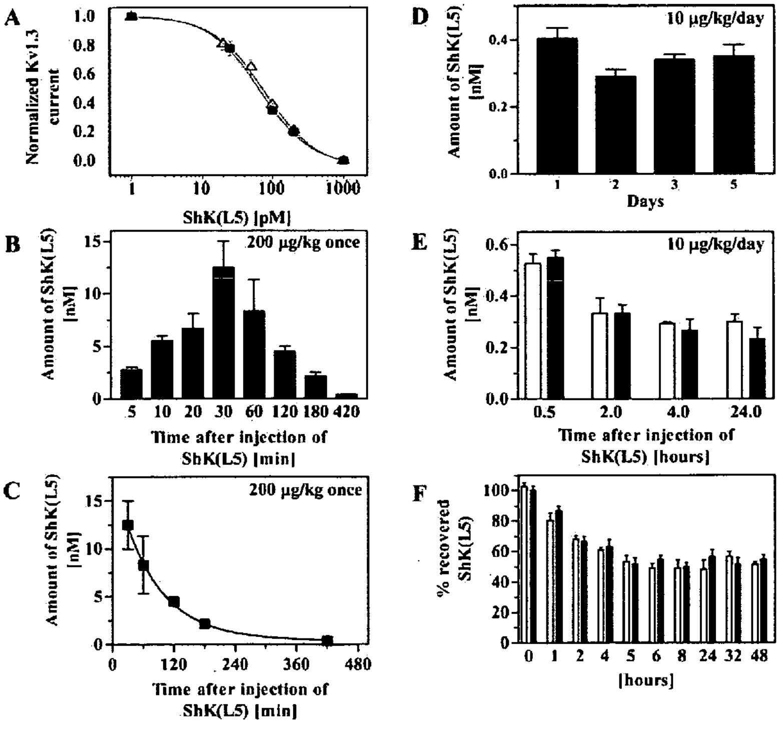

Fig. 4. Circulating half-life and stability of ShK(L5). A, known amounts of ShK(L5) were added to rat serum (△) or to PBS (■) and blocking activity was determined on Kv1.3 channels stably expressed in L929 cells. B, a single dose of 200 μg/kg of ShK(L5) was injected subcutaneously into four rats. Blood was drawn at the indicated times and serum was tested by patch-clamp to determine the amount of ShK(L5). C, data fit to a single exponential decay. Half-life ≈ 50 min. D, five Lewis rats received single daily subcutaneous injections of 10 μg/kg/day ShK(L5) for 5 days. Blood was drawn each morning (24 h after the previous injection) and tested for blocking activity on Kv1.3 channels by patch-clamp. E, rats received a single dose of 10 μg/kg ShK(L5) either subcutaneously (open bars; $n$ = 4) or intravenously (closed bars; $n$ = 4). Blood was drawn at the indicated times. Serum was tested by patch-clamp to determine the amount of ShK(L5) in blood. F, a half-blocking dose of ShK(L5) was added to rat plasma (□) or to PBS containing 2% rat plasma (■) and incubated at 37°C for varying duration. Aliquots were taken at the indicated times and blocking activity determined on Kv1.3 channels.

In the treatment trial (Fig. 5B) rats were injected with MBP-activated PAS cells, administered saline or 10 μg/kg/day ShK(L5) when they initially developed signs of EAE (limp tail, hunched posture, and loss of 6% or more of their weight over 24 h), and therapy was continued for 3 days. Clinical signs of EAE peaked on day 6 in the control group (score = 3.9 ± 0.7) and on day 7 in the treated group (score = 1.9 ± 0.9; $p < 0.05$).

As an independent assessment of the immunosuppressive activity of ShK(L5) in vivo, we also examined its effectiveness in inhibiting the DTH reaction that is mediated predominantly by skin-homing $T_{EM}$ cells (Soler et al., 2003). Lewis rats immunized with ovalbumin and adjuvant were challenged 7 days later with ovalbumin in one ear and saline in the other ear. Rats then received injections of saline (control rats) or ShK(L5) (10 μg/kg/day), and ear thickness was measured as an indication of DTH. All control rats developed ear swelling 24 and 48 h after ovalbumin challenge, whereas the DTH reaction was substantially milder in ShK(L5)-treated animals (Fig. 5C). Thus, ShK(L5) inhibits the $T_{EM}$-mediated DTH response and prevents and ameliorates severe adoptive EAE induced by myelin-activated $T_{EM}$ cells.

Discussion

We have developed a highly specific Kv1.3 inhibitor by attaching the negatively charged amino acid L-*p*Tyr to the N

TABLE 2

Toxicity study of ShK(L5)

Data are expressed as mean ± S.D.

| In vitro tests | | 100 nM ShK(L5) |
|---|---|---|
| Cytotoxicity (% dead cells) | | |
| Human PBMCs | | 7.5 ± 4.3 |
| PAS T cells | | 8.1 ± 0.8 |
| Jurkat cells | | 5.5 ± 3.3 |
| Burkitt lymphoma | | 3.1 ± 0.9 |
| RPMI 8226 myeloma | | 6.5 ± 2.1 |
| Ames test | | Negative |
| **Acute in vivo tests** | **Saline** | **ShK(L5) 10 μg/kg** |
| Electrocardiogram[a] | | |
| Heart rate | 302 ± 13 | 311 ± 20 |
| SDNN | 13.3 ± 3.0 | 17.8 ± 4.4 |
| CV% | 6.7 ± 1.4 | 9.2 ± 2.2 |
| $SDANN_{5\ min}$ | 5.0 ± 2.0 | 6.9 ± 2.3 |
| rMSSD | 6.8 ± 2.2 | 9.8 ± 3.5 |
| HF (n.u.) | 71 ± 21 | 79 ± 37 |
| HF (%) | 50 ± 8 | 53 ± 10 |
| LF (n.u.) | 68 ± 4 | 64 ± 10 |
| LF (%) | 50 ± 8 | 47 ± 10 |
| LF/HF | 1.1 ± 0.4 | 1.3 ± 0.7 |
| **Subchronic in vivo tests** | **Saline** | **ShK(L5) 10 μg/kg/day for 2 weeks** |
| Weight gain (%) | 7.2 ± 1.8 | 6.2 ± 1.7 |
| Complete blood count | | |
| Hematocrit (%) | 40.3 ± 1.4 | 39.0 ± 4.9 |
| Hemoglobin (g/dl) | 15.3 ± 0.5 | 15.0 ± 1.5 |
| MCV (fl) | 48.5 ± 0.2 | 48.3 ± 0.3 |
| MCH (pg) | 18.5 ± 0.8 | 18.5 ± 0.6 |
| MCHC (g/dl) | 38.0 ± 1.8 | 38.4 ± 1.3 |
| Total white cells ($\times 10^3/mm^3$) | 7.1 ± 2.1 | 7.1 ± 2.5 |
| Total red cells ($\times 10^6/mm^3$) | 8.3 ± 0.3 | 8.1 ± 1.0 |
| Total platelets ($\times 10^3/mm^3$) | 656 ± 214 | 606 ± 106 |
| Blood chemistry | | |
| Alkaline phosphatase (U/L) | 170 ± 26 | 150 ± 18 |
| Glucose (mg/dl) | 139 ± 21 | 150 ± 18 |
| Blood urea nitrogen (mg/dl) | 17.1 ± 2.6 | 15.0 ± 1.7 |
| Creatinine (mg/dl) | 0.6 ± 0 | 0.6 ± 0.1 |
| Albumin (g/dl) | 5.0 ± 0.3 | 4.5 ± 0.4 |
| Thymic cell populations (%) | | |
| $CD4^-CD8^-$ | 3.6 ± 1.1 | 4.3 ± 0.7 |
| $CD4^+CD8^+$ | 77.8 ± 6.1 | 76.8 ± 4.1 |
| $CD4^+CD8^-$ | 8.5 ± 1.7 | 11.2 ± 2.0 |
| $CD4^-CD8^+$ | 10.0 ± 3.3 | 7.6 ± 1.3 |
| $CD3^+$ | 89.5 ± 1.6 | 93.2 ± 3.5 |
| Splenic populations (%) | | |
| $CD3^+$ | 72.4 ± 4.4 | 65.4 ± 0.1 |
| $CD3^+CD45RC^+$ | 35.6 ± 2.6 | 39.8 ± 1.1 |
| $CD3^+CD45RC^-$ | 23.6 ± 2.3 | 26.5 ± 1.3 |
| $CD3^+CD4^+$ | 62.7 ± 0.1 | 66.6 ± 1.2 |
| $CD3^+CD8^+$ | 26.9 ± 0.1 | 25.0 ± 0.2 |
| $IgM^+$ | 38.8 ± 1.5 | 33.3 ± 0.3 |

[a] Tested with $t$ tests, $P < 0.05$ on all parameters.

SDNN, standard deviation of all normal-to-normal RR intervals; CV%, 100 × SDNN/average RR interval; $SDANN_{5\ min}$, standard deviation of the mean of normal RR intervals for each 5-min period; rMSSD, root-mean-square of successive difference; HF (n.u.), high frequency (0.75–2.5 Hz) power in normalized unit; LF (n.u.), low frequency (0.2–0.75 Hz) power in normalized unit; MCV, mean corpuscular volume; MCH, mean corpuscular hemoglobin; MCHC, mean corpuscular hemoglobin concentration.

terminus of ShK via a 20-Å hydrophilic linker. ShK(L5) blocks Kv1.3 with a $K_d$ of 69 pM and exhibits selectivity for Kv1.3 of 100-fold over Kv1.1, 260-fold over Kv1.6, 280-fold over Kv3.2, 680-fold over Kv1.2, and >1000-fold over all other channels tested. Other known blockers of Kv1.3 are significantly less selective than ShK(L5). Margatoxin, a peptide from *Centruroides margaritatus* scorpion venom, suppresses DTH in mini-pigs (Koo et al., 1997) but exhibits only 5-fold selectivity for Kv1.3 ($K_d$, 110 pM) over Kv1.2 ($K_d$, 520 pM) and 9-fold selectivity over Kv1.1 ($K_d$, 10 nM). Kaliotoxin from the scorpion *Androctonus mauritanicus* suppresses DTH in rats and ameliorates EAE (Beeton et al., 2001a) and inflammatory bone resorption in experimental periodontal disease (Valverde et al., 2004), but it is less potent (Kv1.3 $K_d$, 650 pM) and less selective (Grissmer et al., 1994) than ShK(L5). The first small-molecule Kv1.3 blockers with nanomolar affinity that were discovered—iminodihydroquinolines

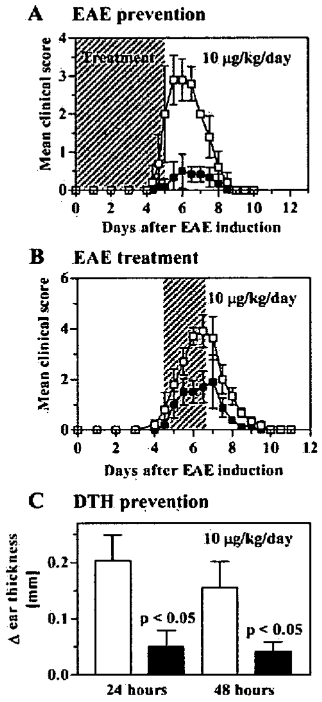

Fig. 5. ShK-L5 prevents DTH and acute adoptive EAE in Lewis rats. A, prevention of EAE. PAS T cells were activated in vitro, washed, and injected intraperitoneally on day 0. Clinical scoring of EAE: 0 = no clinical signs, 0.5 = distal limps tail, 1 = limp tail, 2 = mild paraparesis or ataxia, 3 = moderate paraparesis, 4 = complete hind limb paralysis, 5 = 4 + incontinence, 6 = death. Rats ($n$ = 6/group) were injected subcutaneously with vehicle (□; $n$ = 6) or ShK(L5) (■; $n$ = 6; 10 µg/kg/day) from day 0 to day 5. B, treatment of EAE. PAS T cells were activated in vitro, washed, and injected intraperitoneally on day 0. Treatment with ShK(L5) at 10 µg/kg/day was started when rats developed clinical signs of EAE and was continued for 3 days. C, DTH reaction was elicited against ovalbumin and rats ($n$ = 6/group) were treated with ShK(L5) 10 µg/kg/day for 2 days, after which ear swelling was measured. Statistical analysis was carried out using the Mann-Whitney $U$ test.

WIN-17317 and CP-339818 and the benzhydryl piperidine UK-78282—also block sodium channels (Wanner et al., 1999) and the neuronal Kv1.4 channel (Hanson et al., 1999). The small-molecule Kv1.3 inhibitors developed by Merck—correolide (Felix et al., 1999; Hanner et al., 1999; Koo et al., 1999; Bao et al., 2005), cyclohexyl-subsituted benzamides (Schmalhofer et al., 2002) and candelalides A-C (Singh et al., 2001)—are poorly selective for Kv1.3. Psora-4, the most potent small-molecule Kv1.3 blocker ($K_d$, 3 nM) is only 16- to 20-fold selective for Kv1.3 over Kv1.1 and Kv1.2 and 2.5-fold selective over the cardiac Kv1.5 channel (Vennekamp et al., 2004). Luteolin, a flavonoid that ameliorates EAE in rats (Hendriks et al., 2004), is sold as a nutriceutical (http://www.lutimax.com; http://www.synorx.com), ostensibly because of its ability to block Kv1.3 channels (Lahey and Rajadhyaksha, 2004). However, luteolin is a weak Kv1.3 inhibitor ($K_d$, 65 µM) and it is not selective for Kv1.3 over Kv1.1, Kv1.2, or Kv1.5. Other known Kv1.3 small-molecule blockers—sulfamidebenzamidoindanes (Castle et al., 2000), dichlorophenylpyrazolopyrimidines (Atwal et al., 2001), furoquinoline Ibu-8 (Butenschon et al., 2001), tetraphenylporphyrins (Gradl et al., 2003), 3-alkyl- and 3-aryl-7H-furo[3,2-g]chromen-7-ones (Wernekenschnieder et al., 2004), and khellinone and chalcone derivatives (Baell et al., 2004), charybdotoxin, noxiustoxin, (Grissmer et al., 1994), agitoxin-2 (Garcia et al., 1994), BgK (Cotton et al., 1997), *Pandinius imperator* toxin1 (Peter et al., 2001), HsTx1—are neither as potent nor as selective as ShK(L5). Because of their lack of Kv1.3 selectivity, these blockers could potentially be neurotoxic if they entered the central nervous system at concentrations sufficient to block neuronal channels. The only Kv1.3 inhibitor with potency and Kv1.3-specificity comparable with ShK(L5) is the recently described synthetic analog (OSK1-Lys[16]Asp[20]) of the OSK1 toxin from scorpion *Orthochirus scrobiculosus* (Mouhat et al., 2005), but its activity as an immunomodulator remains undetermined.

The exquisite Kv1.3-specificity of ShK(L5) makes it an attractive drug prospect. ShK(L5) is remarkably stable in plasma and it reached steady-state blood levels of ~300 pM after repeated single daily subcutaneous injections of 10 µg/kg. This blood concentration of ShK(L5) is sufficient to block >90% of Kv1.3 channels without affecting other ion channels and to cause 60 to 70% suppression of $T_{EM}$ cells while sparing naive/$T_{CM}$ cells. A concentration of ShK(L5) greater than 1200 times its pharmacological dose was not cytotoxic or mutagenic in vitro. ShK(L5) did not block the cardiac Kv11.1 (HERG) $K^+$ channel responsible for drug-induced long QT syndrome (Recanatini et al., 2005), and in vivo administration of ShK(L5) at pharmacological concentrations (10 µg/kg/day) did not alter cardiac function in healthy rats based on continuous EKG monitoring. Repeated in vivo administration of 10 µg/kg/day ShK(L5) for 2 weeks did not change clinical chemistry or hematological profiles. Healthy animals administered a single 1000 µg/kg/day ShK(L5) injection (100 times the pharmacological dose) or repeated injections of 600 µg/kg/day for 5 days (60 times the pharmacological dose) did not exhibit any overt signs of toxicity. These results indicate that pharmacologically relevant blood levels can be attained after single daily subcutaneous injections of ShK(L5), and the effective therapeutic safety index in healthy rats exceeds 100.

ShK(L5) may have use as a therapeutic in autoimmune diseases by preferentially targeting continuously activated autoreactive $T_{EM}$ cells that have been implicated in MS, type-1 diabetes mellitus, rheumatoid arthritis, and psoriasis (Ezawa et al., 1997; Lovett-Racke et al., 1998; Scholz et al., 1998; Friedrich et al., 2000; Markovic-Plese et al., 2001; Viglietta et al., 2002; Soler et al., 2003; Wulff et al., 2003). ShK(L5) suppressed the proliferation of human and rat $T_{EM}$ cells ($IC_{50}$ = ~80 pM in both cases) and inhibited IL2 production at picomolar concentrations (Figs. 2 and 3). Exogenous IL2 partially overrode this block. Human naive/$T_{CM}$ cells were initially 60-fold less sensitive to ShK(L5) than human $T_{EM}$ cells and became completely resistant to the blocker during activation (Fig. 2), presumably by up-regulating $K_{Ca}3.1$ (Ghanshani et al., 2000; Wulff et al., 2003). Rat naive/$T_{CM}$ cells were 1000-fold less sensitive to ShK(L5) than $T_{EM}$ cells. This species variation in ShK(L5)-sensitivity of naive/$T_{CM}$ cells compared with $T_{EM}$ cells—60-fold lower in humans and 1000-fold lower in rats—can be explained by differences in $K^+$ channel expression between human and rat naive/$T_{CM}$ cells. Quiescent human naive/$T_{CM}$ cells express more Kv1.3 channels per cell (250–400) than $K_{Ca}3.1$ channels (10–20) and are therefore more potently inhibited by Kv1.3 blockers than $K_{Ca}3.1$ blockers (Ghanshani et al., 2000; Wulff et al., 2003). Quiescent rat naive/$T_{CM}$ cells, in contrast, express more $K_{Ca}3.1$ channels per cell (10–20) than Kv1.3 channels (1–10) and are more sensitive to $K_{Ca}3.1$ than Kv1.3 blockers (Beeton et al., 2001b). The rat/human difference in channel expression may underlie the differential sensitivity of rat naive/$T_{CM}$ cells ($IC_{50}$ = 100 nM) and human naive/$T_{CM}$ cells ($IC_{50}$ = 5 nM) to ShK(L5). In summary, ShK(L5) preferentially suppresses $T_{EM}$ cells, whereas naive/$T_{CM}$ cells are less sensitive to the blocker to begin with and then rapidly escape suppression by up-regulating KCa3.1 channels (Ghanshani et al., 2000; Beeton et al., 2001b; Wulff et al., 2003).

Human class-switched memory B cells (e.g., $CD27^+IgG^+IgD^-$) are implicated in the pathogenicity of autoimmune diseases (Iglesias et al., 2001; O'Connor et al., 2001; Corcione et al., 2004). Kv1.3 blockers preferentially suppress the proliferation of late memory B cells whereas naive and early memory B cells ($CD27^+IgD^+$) are significantly less sensitive (Wulff et al., 2004). ShK(L5) could therefore shut down the function of $T_{EM}$ and class-switched memory B cells that contribute to the development of autoimmune disorders. Of concern is the important role of class-switched memory B cells in humoral immunity (production of IgG antibodies) and the diminished capacity to mount viable immune responses to bacterial challenges that might ensue as a result of channel-based suppression of these cells. It is fortunate that human class-switched memory B cells are less sensitive to block by ShK ($IC_{50}$ = 1–4 nM) than human $T_{EM}$ cells ($IC_{50}$ = 80–400 pM), because they express higher numbers of Kv1.3 channels at rest (~2000/cell) than $T_{EM}$ cells (250–400/cell) (Wulff et al., 2004). It might therefore be possible to titrate the dose of Kv1.3 blockers to preferentially suppress one or both groups of memory cells during therapy of autoimmune disease.

We evaluated ShK(L5) in two rat models of $T_{EM}$ cell-induced disease, EAE induced by adoptive transfer of myelin-specific $T_{EM}$ cells (Beeton et al., 2001b) and DTH caused by skin-homing T cells (Soler et al., 2003). ShK(L5) prevented EAE if administered as a single daily injection (10 μg/kg/day) from the time of adoptive cell transfer, and it significantly reduced disease severity when therapy was initiated at the onset of symptoms. No toxicity was observed in treated EAE rats, suggesting that the blood and tissue concentrations of ShK(L5) achieved with this treatment regimen are not sufficient to block neuronal channels, including heteromultimeric $K_V$ channels containing Kv1.3 subunits (Koch et al., 1997). ShK(L5) was also effective in suppressing DTH. These proof-of-concept studies demonstrate the therapeutic effectiveness of ShK(L5) in ameliorating $T_{EM}$-mediated diseases in rat models. We determined the therapeutic safety index of ShK(L5) in EAE rats (when the blood-brain barrier is likely to be compromised) by administering daily injections of a dose (600 μg/kg/day) 60-fold higher than the therapeutically effective dose. Forty percent of rats with EAE that received this dose died on the fifth day (extrapolated $LD_{50}$ = 750 μg/kg/day for 5 days), which corresponds to a therapeutic safety index of approximately 75.

In conclusion, ShK(L5) is a more selective Kv1.3 blocker than any other known inhibitor, and it might prove beneficial in autoimmune diseases by targeting both $T_{EM}$ cells and class-switched memory B cells. Its picomolar affinity for Kv1.3 and remarkable plasma stability coupled with its high therapeutic safety index in healthy rats (>100) as well as in EAE rats (~75) bodes well for its potential use as a therapeutic immunomodulator. Single daily subcutaneous injections of ShK(L5) are effective in ameliorating EAE and preventing DTH, indicating that this route of peptide delivery would be feasible for therapy.

Acknowledgments

We thank Paul Munch, Suresh Raman, and Daniel Homerick for excellent technical assistance.

References

Atwal KS, Vaccaro W. Lloyd J, Finlay H, Yan L. and Bhandaru RS (2001) inventors, Bristol-Myers Squibb, assignee. Heterocyclic dihydropyrimidines as potassium channel inhibitors. World patent WO0140231. 2001 Jun 7.

Baell JB, Gable RW, Harvey AJ, Toovey N, Herzog T, Hansel W, and Wulff H (2004) Khellinone derivatives as blockers of the voltage-gated potassium channel Kv1.3: synthesis and immunosuppressive activity. *J Med Chem* 47:2326–2336.

Bagdány M, Batista CVF, Valdez-Cruz NA, Somodi S. Rodriguez de la Vega RC, Licea AF. Gáspár R, Possani LD, and Panyi G (2005) Anuroctoxin, a new scorpion toxin of the α-KTx 6 subfamily, is highly selective for Kv1.3 over IKCa1 ion channels of human T lymphocytes. *Mol Pharmacol* 67:1–11.

Bao J, Miao S, Kayser F, Kotliar AJ, Baker RK, Doss GA, Felix JP, Bugianesi RM, Slaughter RS, and Kaczorowski GJ (2005) Potent Kv1.3 inhibitors from correolide–modification of the C18 position. *Bioorg Med Chem Lett* 15:447–451.

Bardien-Kruger S. Wulff H, Arieff Z, Brink P, Chandy KG, and Corfield V (2002) Characterisation of the human voltage-gated potassium channel gene, KCNA7, a candidate gene for inherited cardiac disorders and its exclusion as cause of progressive familial heart block I (PFHBI). *Eur J Hum Genet* 10:36–43.

Beeton C, Barbaria J, Giraud P. Devaux J, Benoliel A, Gola M, Sabatier J, Bernard D, Crest M., and Beraud E (2001a) Selective blocking of voltage-gated $K^+$ channels improves experimental autoimmune encephalomyelitis and inhibits T cell activation. *J Immunol* 166:936–944.

Beeton C, Wulff H. Barbaria J, Clot-Faybesse O, Pennington M, Bernard D, Cahalan M, Chandy K. and Beraud E (2001b) Selective blockade of T lymphocyte $K^+$ channels ameliorates experimental autoimmune encephalomyelitis, a model for multiple sclerosis. *Proc Natl Acad Sci USA* 98:13942–13947.

Beeton C, Wulff H, Singh S, Botsko S, Crossley G. Gutman GA. Cahalan MD, Pennington MW, and Chandy KG (2003) A novel fluorescent toxin to detect and investigate Kv1.3 channel up-regulation in chronically activated T lymphocytes. *J Biol Chem* 278:9928–9937.

Beraud E, Balzano C, Zamora AJ, Varriale S, Bernard D, and Ben-Nun A (1993) Pathogenic and non-pathogenic T lymphocytes specific for the encephalitogenic epitope of myelin basic protein: functional characteristics and vaccination properties. *J Neuroimmunol* 47:41–53.

Bunce C and Bell EB (1997) CD45RC isoforms define two types of CD4 memory T cells, one of which depends on persisting antigen. *J Exp Med* 185:767–776.

Butenschon I, Moller K, and Hansel W (2001) Angular methoxy-substituted furo- and pyranoquinolinones as blockers of the voltage-gated potassium channel Kv1.3. *J Med Chem* 44:1249–1256.

Castle NA, Hollinshead SP, Hughes PF, Mendoza GS. Searafin J, Wilson JW, Amato

GS, Beaudoin S, Gross M, and McNaughton-Smith G (2000) inventors. ICAgen and Eli Lilly & Company, assignee. Potassium channel inhibitors. U.S. patent 6,083,986. 2000 Jul 4.

Chandy KG, DeCoursey TE, Cahalan MD, McLaughlin C, and Gupta S (1984) Voltage-gated potassium channels are required for human T lymphocyte activation. *J Exp Med* 160:369–385.

Chandy KG, Wulff H, Beeton C, Pennington M, Gutman GA, and Cahalan MD (2004) $K^+$ channels as targets for specific immunomodulation. *Trends Pharmacol Sci* 25:280–289.

Corcione A, Casazza S, Ferretti E, Giunti D, Zappia E, Pistorio A, Gambini C, Mancardi GL, Uccelli A, and Pistoria V (2004) Recapitulation of B cell differentiation in the central nervous system of patients with multiple sclerosis. *Proc Natl Acad Sci USA* 101:11064–11069.

Cotton J, Crest M, Bouet F, Alessandri N, Gola M, Forest E, Karlsson E, Castaneda O, Harvey AL, Vita C, et al. (1997) A potassium-channel toxin from the sea anemone *Bunodosoma granulifera*, an inhibitor for Kv1 channels. Revision of the amino acid sequence, disulfide-bridge assignment, chemical synthesis, and biological activity. *Eur J Biochem* 244:192–202.

Deibler GE, Martenson RE, and Kies MW (1972) Large scale preparation of myelin basic protein from central nervous tissue of several mammalian species. *Prep Biochem* 2:139–165.

Ezawa K, Yamamura M, Matsui H, Ota Z, and Makino H (1997) Comparative analysis of CD45RA- and CD45RO-positive $CD4^+$ T cells in peripheral blood, synovial fluid and synovial tissue in patients with rheumatoid arthritis and osteoarthritis. *Acta Med Okayama* 51:25–31.

Felix JP, Bugianesi RM, Schmalhofer WA, Borris R, Goetz MA, Hensens OD, Bao JM, Kayser F, Parsons WH, Rupprecht K, et al. (1999) Identification and biochemical characterization of a novel nortriterpene inhibitor of the human lymphocyte voltage-gated potassium channel, Kv1.3. *Biochemistry* 38:4922–4930.

Friedrich M, Krammig S, Henze M, Docke WD, Sterry W, and Asadullah K (2000) Flow cytometric characterization of lesional T cells in psoriasis: intracellular cytokine and surface antigen expression indicates an activated, memory/effector type 1 immunophenotype. *Arch Dermatol Res* 292:519–521.

Fujiwara Y, Akaji K, and Kiso Y (1994) Racemization-free synthesis of C-terminal cysteine-peptide using 2-chlorotrityl resin. *Chem Pharm Bull (Tokyo)* 42:724–726.

Garcia ML, Garcia-Calvo M, Hidalgo P, Lee A, and MacKinnon R (1994) Purification and characterization of the three inhibitors of voltage-dependent $K^+$ channels from *Leiurus quinquestriatus* var. *hebraeus* venom. *Biochemistry* 33:6834–6839.

Ghanshani S, Wulff H, Miller MJ, Rohm H, Neben A, Gutman GA, Cahalan MD, and Chandy KG (2000) Up-regulation of the IKCa1 potassium channel during T-cell activation: molecular mechanism and functional consequences. *J Biol Chem* 275: 37137–37149.

Gradl SN, Felix JP, Isacoff EY, Garcia ML, and Trauner D (2003) Protein surface recognition by rational design: nanomolar ligands for potassium channels. *J Am Chem Soc* 125:12668–12669.

Grissmer S, Nguyen AN, Aiyar J, Hanson DC, Mather RJ, Gutman GA, Karmilowicz MJ, Auperin DD, and Chandy KG (1994) Pharmacological characterization of five cloned voltage-gated $K^+$ channels, types Kv1.1, 1.2, 1.3, 1.5, and 3.1, stably expressed in mammalian cell lines. *Mol Pharmacol* 45:1227–1234.

Gutman GA, Chandy KG, Adelman JP, Aiyar J, Bayliss DA, Clapham DE, Covarrinbias M, Desir GV, Furuichi K, Ganetzky B, et al. (2003) International Union of Pharmacology. XLI. compendium of voltage-gated ion channels: potassium channels. *Pharmacol Rev* 55:583–586.

Hammerschmidt F and Haubauer M (2000) Transformation of arylmethylamines into alpha-aminophosphonic acids via metalated phosphoramidates: rearrangements of partly configurationally stable N-phosphorylated alpha-aminocarbanions. *J Org Chem* 65:6121–6131.

Hanner M, Schmalhofer WA, Green B, Bordallo C, Liu J, Slaughter RS, Kaczorowski GJ, and Garcia ML (1999) Binding of correolide to Kv1 family potassium channels. *J Biol Chem* 274:25237–25244.

Hanson DC, Nguyen A, Mather RJ, Rauer H, Koch K, Burgess LE, Rizzi JP, Donovan CB, Bruns MJ, Canniff PC, et al. (1999) UK-78,282, a novel piperidine compound that potently blocks the Kv1.3 voltage-gated potassium channel and inhibits human T cell activation. *Br J Pharmacol* 126:1707–1716.

Hendriks JJA, Alblas J, van der Pol SMA, van Tol EAF, Dijkstra CD, and de Vries HE (2004) Flavonoids influence monocytic GTPase activity and are protective in experimental allergic encephalitis. *J Exp Med* 200:1667–1672.

Iglesias A, Bauer J, Litzenburger T, Schubart A, and Linington C (2001) T- and B-cell responses to myelin oligodendrocyte glycoprotein in experimental autoimmune encephalomyelitis and multiple sclerosis. *Glia* 36:220–234.

Kalman K, Pennington MW, Lanigan MD, Nguyen A, Rauer H, Mahnir V, Paschetto K, Kem WR, Grissmer S, Gutman GA, et al. (1998) ShK-Dap[22], a potent Kv1.3-specific immunosuppressive polypeptide. *J Biol Chem* 273:32697–32707.

King DS, Fields CG, and Fields GB (1990) A cleavage method which minimizes side reactions following Fmoc solid phase peptide synthesis. *Int J Pept Protein Res* 36:255–266.

Koch RO, Wanner SG, Koschak A, Hanner M, Schwarzer C, Kaczorowski GJ, Slaughter RS, Garcia ML, and Knaus HG (1997) Complex subunit assembly of neuronal voltage-gated $K^+$ channels. Basis for high-affinity toxin interactions and pharmacology. *J Biol Chem* 272:27577–27581.

Kolski-Andreaco A, Tomita H, Shakkottai VG, Gutman GA, Cahalan MD, Gargus JJ, and Chandy KG (2004) SK3-1C, a dominant-negative suppressor of $SK_{Ca}$ and $IK_{Ca}$ channels. *J Biol Chem* 279:6893–6904.

Koo GC, Blake JT, Shah K, Staruch MJ, Dumont F, Wunderler D, Sanchez M, McManus OB, Sirotina-Meisher A, Fischer P, et al. (1999) Correolide and derivatives are novel immunosuppressants blocking the lymphocyte Kv1.3 potassium channels. *Cell Immunol* 197:99–107.

Koo GC, Blake JT, Talento A, Nguyen M, Lin S, Sirotina A, Shah K, Mulvany K, Hora D Jr, Cunningham P, et al. (1997) Blockade of the voltage-gated potassium channel Kv1.3 inhibits immune responses in vivo. *J Immunol* 158:5120–5128.

Koschak A, Bugianesi RM, Mitterdorfer J, Kaczorowski GJ, Garcia ML, and Knaus HG (1998). Subunit composition of brain voltage-gated potassium channels determined by hongotoxin-1, a novel peptide derived from *Centruroides limbatus* venom. *J Biol Chem.* 273:2639–2644.

Lahey T and Rajadhyaksha VJ (2004) 3-Deoxyflavonoid inhibition of T-lymphocyte activation and therapeutic use, pp 19, US patent 2004102386.

Lin CS, Boltz RC, Blake JT, Nguyen M, Talento A, Fischer PA, Springer MS, Sigal NH, Slaughter RS, Garcia ML, et al. (1993) Voltage-gated potassium channels regulate calcium-dependent pathways involved in human T lymphocyte activation. *J Exp Med* 177:637–645.

Lovett-Racke AE, Trotter JL, Lauber J, Perrin PJ, June CH, and Racke MK (1998) Decreased dependence of myelin basic protein-reactive T cells on CD28-mediated costimulation in multiple sclerosis patients: a marker of activated/memory T cells. *J Clin Investig* 101:725–730.

Markovic-Plese S, Cortese I, Wandinger KP, McFarland HF, and Martin R (2001) $CD4^+CD28^-$ costimulation-independent T cells in multiple sclerosis. *J Clin Investig* 108:1185–1194.

Middleton RE, Sanchez M, Linde AR, Bugianesi RM, Dai G, Felix JP, Koprak SL, Staruch MJ, Bruguera M, Cox R, et al. (2003) Substitution of a single residue in Stichodactyla helianthus peptide, ShK-Dap[22], reveals a novel pharmacological profile. *Biochemistry* 42:13698–13707.

Mouhat S, Visan V, Ananthakrishnan S, Wulff H, Andreotti N, Grissmer S, Darbon H, De Waard M, and Sabatier JM (2005) $K^+$ channel types targeted by synthetic OSK1, a toxin from *Orthochirus scrobiculosus* scorpion venom. *Biochem J* 385:95–104.

Nicolas E, Vilaseca M, and Giralt E (1995) A study of the use of $NH_4I$ for the reduction of methionine sulphoxide in peptides containing cysteine and cystine. *Tetrahedron* 51:5701–5710.

O'Connor K, Bar-Or A, and Hafler DA (2001) The neuroimmunology of multiple sclerosis: possible roles of T and B lymphocytes in immunopathogenesis. *J Clin Immunol* 21:81–92.

Pennington M, Byrnes M, Zaydenberg I, Khaytin I, de Chastonay J, Krafte D, Hill R, Mahnir V, Volberg W, Gorczyca W, et al. (1995) Chemical synthesis and characterization of ShK toxin: a potent potassium channel inhibitor from a sea anemone. *Int J Pept Protein Res* 346:354–358.

Pennington M, Mahnir V, Khaytin I, Zaydenberg I, Byrnes M, and Kem W (1996a) An essential binding surface for ShK toxin interaction with rat brain potassium channels. *Biochemistry* 35:16407–16411.

Pennington M, Mahnir V, Krafte D, Zaydenberg I, Byrnes M, Khaytin I, Crowley K, and Kem W (1996b) Identification of three separate binding sites on ShK toxin, a potent inhibitor of voltage-dependent potassium channels in human T-lymphocytes and rat brain. *Biochem Biophys Res Commun* 219:696–701.

Peter MJ, Varga Z, Hajdu P, Gaspar RJ, Damjanovich S, Horjales E, Possani LD, and Panyi G (2001) Effects of toxins Pi2 and Pi3 on human T lymphocyte Kv1.3 channels: the role of Glu7 and Lys24. *J Membr Biol* 179:13–25.

Recanatini M, Poluzzi E, Masetti M, Cavalli A, and De Ponti F (2005) QT prolongation through hERG $K^+$ channel blockade: current knowledge and strategies for the early prediction during drug development. *Med Res Rev* 25:133–166.

Regaya I, Beeton C, Ferrat G, Andreotti N, Darbon H, De Waard M, and Sabatier JM (2004) Evidence for domain-specific recognition of SK and Kv channels by MTX and HsTX1 scorpion toxins. *J Biol Chem* 279:55690–55696.

Sallusto F, Lenig D, Forster R, Lipp M, and Lanzavecchia A (1999) Two subsets of memory T lymphocytes with distinct homing potentials and effector functions. *Nature (Lond)* 401:708–712.

Schmalhofer WA, Bao J, McManus OB, Green B, Matyskiela M, Wunderler D, Bugianesi RM, Felix JP, Hanner M, Linde-Arias AR, et al. (2002) Identification of a new class of inhibitors of the voltage-gated potassium channel, Kv1.3, with immunosuppressant properties. *Biochemistry* 41:7781–7794.

Scholz C, Patton KT, Anderson DE, Freeman GJ, and Hafler DA (1998) Expansion of autoreactive T cells in multiple sclerosis is independent of exogenous B7 costimulation. *J Immunol* 160:1532–1538.

Singh S, Zink DL, Dombrowski AW, Dezeny G, Bills GF, Felix J, Slaughter RS, and Goetz MA (2001) Candelalides A-C: novel diterpenoid pyrones from fermentations of *Sesquicillium candelabrum* as blockers of the voltage-gated potassium channel Kv1.3. *Org Lett* 3:247–250.

Soler D, Humphreys TL, Spinola SM, and Campbell JJ (2003) CCR4 versus CCR10 in human cutaneous TH lymphocyte trafficking. *Blood* 101:1677–1682.

Task Force of the European Society of Cardiology the North American Society of Pacing Electrophysiology (1996) Heart Rate variability: standards of measurement, physiological interpretation and clinical use. *Circulation* 93:1043–1065.

Tian Z, Gu C, Roeske RW, Zhou M, and Van Etten RL (1993) Synthesis of phosphotyrosine-containing peptides by solid-phase method. *Int J Peptide Protein Res* 42:155–158.

Valverde P, Kawai T, and Taubman M (2004) Selective blockade of voltage-gated potassium channels reduces inflammatory bone resorption in experimental periodontal disease. *J Bone Miner Res* 19:155–164.

Vennekamp J, Wulff H, Beeton C, Calabresi PA, Grissmer S, Hansel W, and Chandy KG (2004) Kv1.3 blocking 5-phenylalkoxypsoralens: a new class of immunomodulators. *Mol Pharmacol* 65:1364–1374.

Viglietta V, Kent SC, Orban T, and Hafler DA (2002) GAD65-reactive T cells are activated in patients with autoimmune type 1a diabetes. *J Clin Investig* 109:895–903.

Wanner SG, Glossmann H, Knaus HG, Baker R, Parsons W, Rupprecht KM, Brochu R, Cohen CJ, Schmalhofer W, Smith M, et al. (1999) WIN 17317-3, a new high-affinity probe for voltage-gated sodium channels. *Biochemistry* 38:11137–11146.

Wernekenschnieder A, Korner P, and Hansel W (2004) 3-Alkyl- and 3-aryl-7H-furo[3,2-*g*]chromen-7-ones as blockers of the voltage-gated potassium channel Kv1.3. *Pharmazie* 59:319–320.

Wulff H, Calabresi P, Allie R, Yun S, Pennington MW, Beeton C, and Chandy KG (2003) The voltage-gated Kv1.3 $K^+$ channel in effector memory T cells as new target for MS. *J Clin Investig* 111:1703–1713.
Wulff H, Knaus H, Pennington M, and Chandy KG (2004) $K^+$ channel expression during B cell differentiation: implications for immunomodulation and autoimmunity. *J Immunol* 173:776–786.
Wulff H, Miller MJ, Haensel W, Grissmer S, Cahalan MD, and Chandy KG (2000) Design of a potent and selective inhibitor of the intermediate-comductance $Ca^{2+}$-activated $K^+$ channel, IKCa1: a potential immunosuppressant. *Proc Natl Acad Sci USA* 97:8151–8156.
Zhou W, Cayabyab FS, Pennefather PS, Schlichter LC, and DeCoursey TE (1998) HERG-like $K^+$ channels in microglia. *J Gen Physiol* 111:781–794.

Address correspondence to: Reprint requests to: K. George Chandy, M.D., Ph.D., Department of Physiology and Biophysics, Medical School, 291 Irvine Hall, University of California, Irvine, Irvine, CA 92697-4561. Tel: 949-824-7435, Fax: 949-824-3143, email: gchandy@uci.edu

What is claimed is:

1. A composition of matter comprising ShK toxin attached to a chemical entity that has an anionic charge, said chemical entity comprising an entity selected from AEEAc-p-Phosphono(difluoro-methyl)-Phenylalanine (Pfp) and AEEAc-p-Phosphono-methylketo-Phenylalanine (Pkp), wherein said chemical entity is attached to the N-terminal residue of ShK.

2. A composition according to claim 1 wherein the ShK toxin is obtained from a natural source.

3. A composition according to claim 1 wherein the ShK toxin is synthetic.

4. A composition according to claim 1 wherein the chemical entity includes a fluorophore tag.

5. A composition according to claim 1 wherein the ShK is modified by substitution of the Met residue at position 21.

6. A composition according to claim 1 wherein the Met residue at position 21 is replaced by a Nle residue.

7. A composition according to claim 1 wherein the ShK is modified by substitution of the C-terminal acid function with an amide.

8. A composition according to claim 1 wherein said ShK has the amino acid sequence: Arg-Ser-Cys-Ile-Asp-Thr-Ile-Pro-Lys-Ser-Arg-Cys-Thr-Ala-Phe-Gln-Cys-Lys-H is-Ser-Met-Lys-Tyr-Arg-Leu-Ser-Phe-Cys-Arg-Lys-Thr-Cys-Gly-Thr-Cys (SEQ ID NO:1).

9. A composition according to claim 1 having the sequence Phosphono(difluoro-methyl)-Phenylalanine-AEEAc-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys (SEQ ID NO: 5 to be-added).

10. A composition according to claim 1 having the sequence Phosphono(difluoro-methyl)-Phenylalanine-AEEAc-Arg-Ser-Cys-Ile-Asp-Thr-Ile-Pro-Lys-Ser-Arg-Cys-Thr-Ala-Phe-Gln-Cys-Lys-His-Ser-Nle-Lys-Tyr-Arg-Leu-Ser-Phe-Cys-Arg-Lys-Thr-Cys-Gly-Thr-Cys-amide (SEQ ID NO: 6).

11. A composition according to claim 1 having the sequence: Phosphono-methylketo-Phenylalanine-AEEAc-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys (SEQ ID NO: 7).

12. A composition according to claim 1 having the sequence: Phosphono-methylketo-Phenylalanine-AEEAc-Arg-Ser-Cys-Ile-Asp-Thr-Ile-Pro-Lys-Ser-Arg-Cys-Thr-Ala-Phe-Gln-Cys-Lys-His-Ser-Nle-Lys-Tyr-Arg-Leu-Ser-Phe-Cys-Arg-Lys-Tlu-Cys-Gly-Thr-Cys-amide (SEQ ID NO: 8).

13. A method for causing inhibition of Kv1.3 potassium channels in a human or animal subject, said method comprising administering to the subject a composition according to claim 1, in a form and amount that is effective to inhibit Kv1.3 potassium channels.

14. A method according to claim 13 wherein the method is carried out to treat an autoimmune disorder.

15. A method according to claim 14 wherein the autoimmune disorder is selected from the group consisting of: Multiple sclerosis, Myasthenia gravis, Autoimmune neuropathies, Guillain-Barre Syndrome, Autoimmune uveitis, Crohn's Disease, Ulcerative colitis, Primary biliary cirrhosis, Autoimmune hepatitis, Autoimmunethrombocytopenia, Type 1 diabetes mellitus, Addison's Disease, Grave's Disease, Hashimoto's thyroiditis, Autoimmune oophoritis, Autoimmune orchitis, Behcet's disease, Rheumatoid arthritis, Bone resorption associated with periodontal disease, Systemic lupus erythematosus, Scleroderma, Polymyositis, dermatomyositis, Pemphigus vulgaris, Spondyloarthropathies, Ankylosing spondylitis, and Sjogren's syndrome.

16. A method according to claim 13 wherein the method is carried out to prevent or treat graft vs. host disease.

17. A method according to claim 13 wherein the method is carried out to prevent or treat rejection of a transplanted tissue or organ.

18. A method according to claim 13 wherein the method is carried out to prevent or treat metabolic syndrome.

19. A method according to claim 13 wherein the method is carried out to treat or prevent Type 2 diabetes.

20. A method according to claim 13 wherein the method is carried out to treat or prevent obesity.

* * * * *

SEQUENCE LISTING

```
<160> NUMBER OF SEQ ID NOS: 8

<210> SEQ ID NO 1
<211> LENGTH: 35
<212> TYPE: PRT
<213> ORGANISM: Stichodactyla helianthus

<400> SEQUENCE: 1

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35


<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: p-phospho-Tyr
<220> FEATURE:
<221> NAME/KEY: MOD_RES
<222> LOCATION: (2)..(2)
<223> OTHER INFORMATION: AEEAc

<400> SEQUENCE: 2

Tyr Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
        35


<210> SEQ ID NO 3
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: p-phospho-Tyr
<220> FEATURE:
<221> NAME/KEY: MOD_RES
<222> LOCATION: (2)..(2)
<223> OTHER INFORMATION: AEEAc
<220> FEATURE:
<221> NAME/KEY: misc_feature
<222> LOCATION: (37)..(37)
<223> OTHER INFORMATION: C-term amidated

<400> SEQUENCE: 3

Tyr Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
        35
```

```
<210> SEQ ID NO 4
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: AEEAc
<220> FEATURE:
<221> NAME/KEY: misc_feature
<222> LOCATION: (37)..(37)
<223> OTHER INFORMATION: C-term amidated

<400> SEQUENCE: 4

Tyr Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
        35


<210> SEQ ID NO 5
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phosphono(difluoro-methyl)-Phe
<220> FEATURE:
<221> NAME/KEY: MOD_RES
<222> LOCATION: (2)..(2)
<223> OTHER INFORMATION: AEEAc

<400> SEQUENCE: 5

Phe Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
        35


<210> SEQ ID NO 6
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phosphono(difluoro-methyl)-Phe
<220> FEATURE:
<221> NAME/KEY: MOD_RES
<222> LOCATION: (2)..(2)
<223> OTHER INFORMATION: AEEAc
<220> FEATURE:
<221> NAME/KEY: MOD_RES
<222> LOCATION: (23)..(23)
<223> OTHER INFORMATION: Nle
<220> FEATURE:
<221> NAME/KEY: misc_feature
<222> LOCATION: (37)..(37)
```

-continued

<223> OTHER INFORMATION: C-term amidated

<400> SEQUENCE: 6

Phe Xaa Arg Ser Cys Ile Asp Thr Ile Pro Lys Ser Arg Cys Thr Ala
1               5                   10                  15

Phe Gln Cys Lys His Ser Xaa Lys Tyr Arg Leu Ser Phe Cys Arg Lys
            20                  25                  30

Thr Cys Gly Thr Cys
        35

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phosphono-methylketo-Phe
<220> FEATURE:
<221> NAME/KEY: MOD_RES
<222> LOCATION: (2)..(2)
<223> OTHER INFORMATION: AEEAc

<400> SEQUENCE: 7

Phe Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
        35

<210> SEQ ID NO 8
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phosphono-methylketo-Phe
<220> FEATURE:
<221> NAME/KEY: MOD_RES
<222> LOCATION: (2)..(2)
<223> OTHER INFORMATION: AEEAc
<220> FEATURE:
<221> NAME/KEY: MOD_RES
<222> LOCATION: (23)..(23)
<223> OTHER INFORMATION: Nle
<220> FEATURE:
<221> NAME/KEY: misc_feature
<222> LOCATION: (37)..(37)
<223> OTHER INFORMATION: C-term amidated

<400> SEQUENCE: 8

Phe Xaa Arg Ser Cys Ile Asp Thr Ile Pro Lys Ser Arg Cys Thr Ala
1               5                   10                  15

Phe Gln Cys Lys His Ser Xaa Lys Tyr Arg Leu Ser Phe Cys Arg Lys
            20                  25                  30

Thr Cys Gly Thr Cys
        35